US012620489B2

(12) United States Patent
Ziegler et al.

(10) Patent No.: US 12,620,489 B2
(45) Date of Patent: May 5, 2026

(54) METHOD FOR DETERMINING THE RISK TO DEVELOP TYPE 1 DIABETES

(71) Applicants: HELMHOLTZ ZENTRUM MÜNCHEN-DEUTSCHES FORSCHUNGSZENTRUM FÜR GESUNDHEIT UND UMWELT (GMBH), Neuherberg (DE); TECHNISCHE UNIVERSITÄT DRESDEN, Dresden (DE)

(72) Inventors: Anette-G. Ziegler, Munich (DE); Ezio Bonifacio, Munich (DE); Christiane Winkler, Munich (DE); Jan Krumsiek, Munich (DE); Fabian Theis, Garching (DE); Peter Achenbach, Munich (DE)

(73) Assignees: Helmholtz Zentrum München Deutsches Forschungszentrum für Gesundheit und Umwelt (GmbH), Neuherberg (DE); Technische Universität Dresden, Dresden (DE)

( * ) Notice: Subject to any disclaimer, the term of this patent is extended or adjusted under 35 U.S.C. 154(b) by 1466 days.

(21) Appl. No.: 16/626,200

(22) PCT Filed: Jun. 27, 2018

(86) PCT No.: PCT/EP2018/067240
§ 371 (c)(1),
(2) Date: Dec. 23, 2019

(87) PCT Pub. No.: WO2019/002364
PCT Pub. Date: Jan. 3, 2019

(65) Prior Publication Data
US 2020/0126671 A1      Apr. 23, 2020

(30) Foreign Application Priority Data

Jun. 28, 2017    (EP) ..................................... 17178396
Jul. 13, 2017    (LU) ........................................ 100334

(51) Int. Cl.
| | |
|---|---|
| *G16H 50/30* | (2018.01) |
| *A61K 38/28* | (2006.01) |
| *C12Q 1/6883* | (2018.01) |
| *G01N 33/49* | (2006.01) |
| *G16B 20/20* | (2019.01) |
| *G16H 20/10* | (2018.01) |
| *A61K 35/12* | (2015.01) |

(52) U.S. Cl.
CPC ........... *G16H 50/30* (2018.01); *C12Q 1/6883* (2013.01); *G01N 33/49* (2013.01); *G16B 20/20* (2019.02); *G16H 20/10* (2018.01); *A61K 2035/122* (2013.01); *A61K 38/28* (2013.01); *C12Q 2600/118* (2013.01); *C12Q 2600/156* (2013.01); *C12Q 2600/172* (2013.01); *G01N 2800/042* (2013.01); *G01N 2800/50* (2013.01)

(58) Field of Classification Search
None
See application file for complete search history.

(56) References Cited

U.S. PATENT DOCUMENTS

2012/0309639 A1    12/2012  Hakonarson et al.

FOREIGN PATENT DOCUMENTS

| | | |
|---|---|---|
| CN | 102791282 A | 11/2012 |
| CN | 103372214 A | 10/2013 |
| CN | 103889443 A | 6/2014 |
| CN | 104395479 A | 3/2015 |
| KR | 2016 0143008 A | 12/2016 |
| WO | WO-2005014634 A1 | 2/2005 |
| WO | WO-2011015984 A1 | 2/2011 |
| WO | WO 2011/044458 A1 | 4/2011 |
| WO | WO-2012174480 A2 | 12/2012 |
| WO | WO-2013110245 A1 | 8/2013 |
| WO | WO-2013163887 A1 | 11/2013 |
| WO | WO-2015128617 A1 | 9/2015 |
| WO | WO-2019002364 A1 | 1/2019 |

OTHER PUBLICATIONS

Pociot, F., Akolkar, B., Concannon, P., Erlich, H.A., Julier, C., Morahan, G., Nierras, C.R., Todd, J.A., Rich, S.S. and Nerup, J., 2010. Genetics of type 1 diabetes: what's next?. Diabetes, 59(7), p. 1561. (Year: 2010).*
Oram et al., 2016. A type 1 diabetes genetic risk score can aid discrimination between type 1 and type 2 diabetes in young adults. Diabetes care, 39(3), pp. 337-344 (8 pages), plus 3 pages supplemental material, total 11 pages, (online Nov. 2015)). (Year: 2016).*
Näntö-Salonen et al., 2008. Nasal insulin to prevent type 1 diabetes in children with HLA genotypes and autoantibodies conferring increased risk of disease: a double-blind, randomised controlled trial. The Lancet, 372(9651), pp. 1746-1755. (Year: 2008).*
Skyler, J.S., Krischer, J.P., Wolfsdorf, J. and Cowie, C., 2005. Effects of oral insulin in relatives of patients with type 1 diabetes: The Diabetes Prevention Trial—Type 1. Diabetes care, 28(5), p. 1068-1076. (Year: 2005).*

(Continued)

*Primary Examiner* — G. Steven Vanni
*Assistant Examiner* — Meredith Abbott Vassell

(57) ABSTRACT

The present invention relates to a method of determining whether a subject is at risk of developing type 1 diabetes by determining the genetic risk score (GRS) of a subject. The present invention also comprises a pharmaceutical composition comprising insulin and a pharmaceutical acceptable carrier for use in a method for preventing type 1 diabetes in a subject having a genetic risk score as determined by the method mentioned above. Further, it encompasses a kit for use in a method of determining whether a subject is at risk of developing type 1 diabetes by determining the genetic risk score of a subject and a type 1 diabetes antigen for use in a method of immunizing a subject against type 1 diabetes having a genetic risk score as determined by the method mentioned above.

7 Claims, 32 Drawing Sheets

Specification includes a Sequence Listing.

(56) References Cited

OTHER PUBLICATIONS

Skyler et al., (Diabetes Prevention Trial—Type 1 Diabetes Study Group), 2002. Effects of insulin in relatives of patients with type 1 diabetes mellitus. New England Journal of Medicine, 346(22), pp. 1685-1691. (Year: 2002).*

Bonifacio et al., 2015. Effects of high-dose oral insulin on immune responses in children at high risk for type 1 diabetes: the Pre-POINT randomized clinical trial. Jama, 313(15), pp. 1541-1549. (Year: 2015).*

Ziegler, A.G., Danne, T., Daniel, C. and Bonifacio, E., 2021. 100 years of insulin: lifesaver, immune target, and potential remedy for prevention. Med, 2(10), pp. 1120-1137. (Year: 2021).*

Assfalg, R., Knoop, J., Hoffman, K.L., Pfirrmann, M., Zapardiel-Gonzalo, J.M., Hofelich, A., Eugster, A., Weigelt, M., Matzke, C., Reinhardt, J. and Fuchs, Y., 2021. Oral insulin immunotherapy in children at risk for type 1 diabetes in a randomised controlled trial. Diabetologia, 64, pp. 1079-1092. (Year: 2021).*

Larsson, H.E. and Lernmark, Å., 2011. Vaccination against type 1 diabetes. Journal of internal medicine, 269(6), pp. 626-635. (Year: 2011).*

Brorsson et al., "Genetic Risk Score Modelling for Disease Progression in New-Onset Type I Diabetes Patients: Increased Genetic Load of Islet-Expressed and Cytokine-Regulated Candidate Genes Predicts Poorer Glycemic Control," Journal of Diabetes Research, vol. 2016, Article ID 9570424, 8 pages (2015).

Oram et al., "A Type 1 Diabetes Genetic Risk Score Can Aid Discrimination Between Type 1 and Type 2 Diabetes in Young Adults," Diabetes Care 39:337-344 (2016).

Toern et al., "Role of Type 1 Diabetes-Associated SNPs on Risk of Autoantibody Positivity in the TEDDY Study," Diabetes 64:1818-1829 (2015).

Watkins et al., "Established and emerging biomarkers for the prediction of type 110-121 diabetes: a systematic review," Translational Research 164(2):110-121 (2014).

Winkler et al., "Feature ranking of type 1 diabetes susceptibility genes improves prediction of type 1 diabetes," Diabetologia 57:2521-2529 (2014).

Ziegler et al., "Primary prevention of beta-cell autoimmunity and type 1 diabetes—The Global PlaHorm for the Prevention of Autoimmune Diabetes (GPPAD) perspectives," Molecular Metabolism 5:255-262 (2016).

Author Unknown, Wellcome Trust Case Control Consortium, "Genome-wide association study of 14,000 cases of seven common diseases and 3,000 shared controls," Nature. Jun. 7, 2007; 447(7145):661-78.

Barrett, et al., "Genome-wide association study and meta-analysis find that over 40 loci affect risk of type 1 diabetes," Nat Genet. Jun. 2009; 41(6):703-7. Epub May 10, 2009.

Blanche, et al., "Estimating and comparing time-dependent areas under receiver operating characteristic curves for censored event times with competing risks," Stat Med. Dec. 30, 2013; 32(30):5381-97. Epub Sep. 12, 2013.

Bonifacio, et al., "Harmonization of glutamic acid decarboxylase and islet antigen-2 autoantibody assays for national institute of diabetes and digestive and kidney diseases consortia," J Clin Endocrinol Metab. Jul. 2010; 95(7):3360-7. Epub May 5, 2010.

Bonifacio, et al., "Predicting type 1 diabetes using biomarkers," Diabetes Care. Jun. 2015; 38(6):989-96.

Clayton, D.G., "Prediction and interaction in complex disease genetics: experience in type 1 diabetes," PLoS Genet. Jul. 2009; 5(7):e1000540, 6 pages. Epub Jul. 3, 2009.

Du Toit, et al., "Randomized trial of peanut consumption in infants at risk for peanut allergy," N Engl J Med. Feb. 26, 2015; 372(9):803-13. Epub Feb. 23, 2015. Erratum in: N Engl J Med. Jul. 28, 2016; 375(4):398.

Groskreutz, et al.,. "Genetically engineered proinsulin constitutively processed and secreted as mature, active insulin," J Biol Chem. Feb. 25, 1994; 269(8):6241-5.

Guinney, et al., "Prediction of overall survival for patients with metastatic castration-resistant prostate cancer: development of a prognostic model through a crowdsourced challenge with open clinical trial data," Lancet Oncol. Jan. 2017; 18(1):132-142. Epub Nov. 16, 2016.

International Preliminary Report on Patentability issued Dec. 31, 2019, for PCT/EP2018/067240, 7 pages.

International Search Report & Written Opinion mailed Sep. 3, 2018, for PCT/EP2018/067240, 12 pages.

Kass, et al., "Bayes Factors," Journal of the American Statistical Association, Jun. 1995; 90(430):773-795.

Knip, et al., "Hydrolyzed infant formula and early B-cell autoimmunity: a randomized clinical trial," JAMA. Jun. 11, 2014; 311(22):2279-87.

Krischer, et al., "The 6 year incidence of diabetes-associated autoantibodies in genetically at-risk children: the TEDDY study," Diabetologia. May 2015; 58(5):980-7. Epub Feb. 10, 2015.

Krischer, J., Teddy Study Group, "The Environmental Determinants of Diabetes in the Young (TEDDY) study: study design," Pediatr Diabetes. Oct. 2007; 8(5):286-98.

Lambert, et al., "Absolute risk of childhood-onset type 1 diabetes defined by human leukocyte antigen class II genotype: a population-based study in the United Kingdom," J Clin Endocrinol Metab. Aug. 2004; 89(8):4037-43.

Lionetti, et al., "Introduction of gluten, HLA status, and the risk of celiac disease in children," N Engl J Med. Oct. 2, 2014; 371(14):1295-303.

Liu, et al., "Risk of pediatric celiac disease according to HLA haplotype and country," N Engl J Med. Jul. 3, 2014; 371(1):42-9. Erratum in: N Engl J Med. Jul. 24, 2014; 371(4):390.

Nolan, et al., "The structure of bovine proinsulin," J Biol Chem. May 10, 1971; 246(9):2780-95.

Rewers, et al., "Newborn screening for HLA markers associated with IDDM: diabetes autoimmunity study in the young (DAISY)," Diabetologia. Jul. 1996; 39(7):807-12.

Sudlow, et al., "UK biobank: an open access resource for identifying the causes of a wide range of complex diseases of middle and old age," PLoS Med. Mar. 31, 2015; 12(3):e1001779, 10 pages.

Vriezinga, et al., "Randomized feeding intervention in infants at high risk for celiac disease," N Engl J Med. Oct. 2, 2014; 371(14):1304-15.

Ziegler, et al., "Seroconversion to multiple islet autoantibodies and risk of progression to diabetes in children," JAMA. Jun. 19, 2013; 309(23):2473-9.

Ziegler, et al., "Prediction and pathogenesis in type 1 diabetes," Immunity. Apr. 23, 2010; 32(4):468-78.

Lu, Shiping, et al., "Clinical development of Type 1 diabetes vaccine," Journal of China Pharmaceutical University, vol. 45, Issue 06, Dec. 25, 2014, pp. 625-632.

Zhang, Liuwei, et al., "Comparing the risk assessment models of type 2 diabetes mellitus on the basis of environmental and genetic risk factors," Department of Sport Statistics and Physique Assessment, Sport Science College, Beijing Sport University, Chinese Journal of Disease Control & Prevention, 2016, vol. 24, Issue 02, pp. 84-88, 2 page abstract.

* cited by examiner

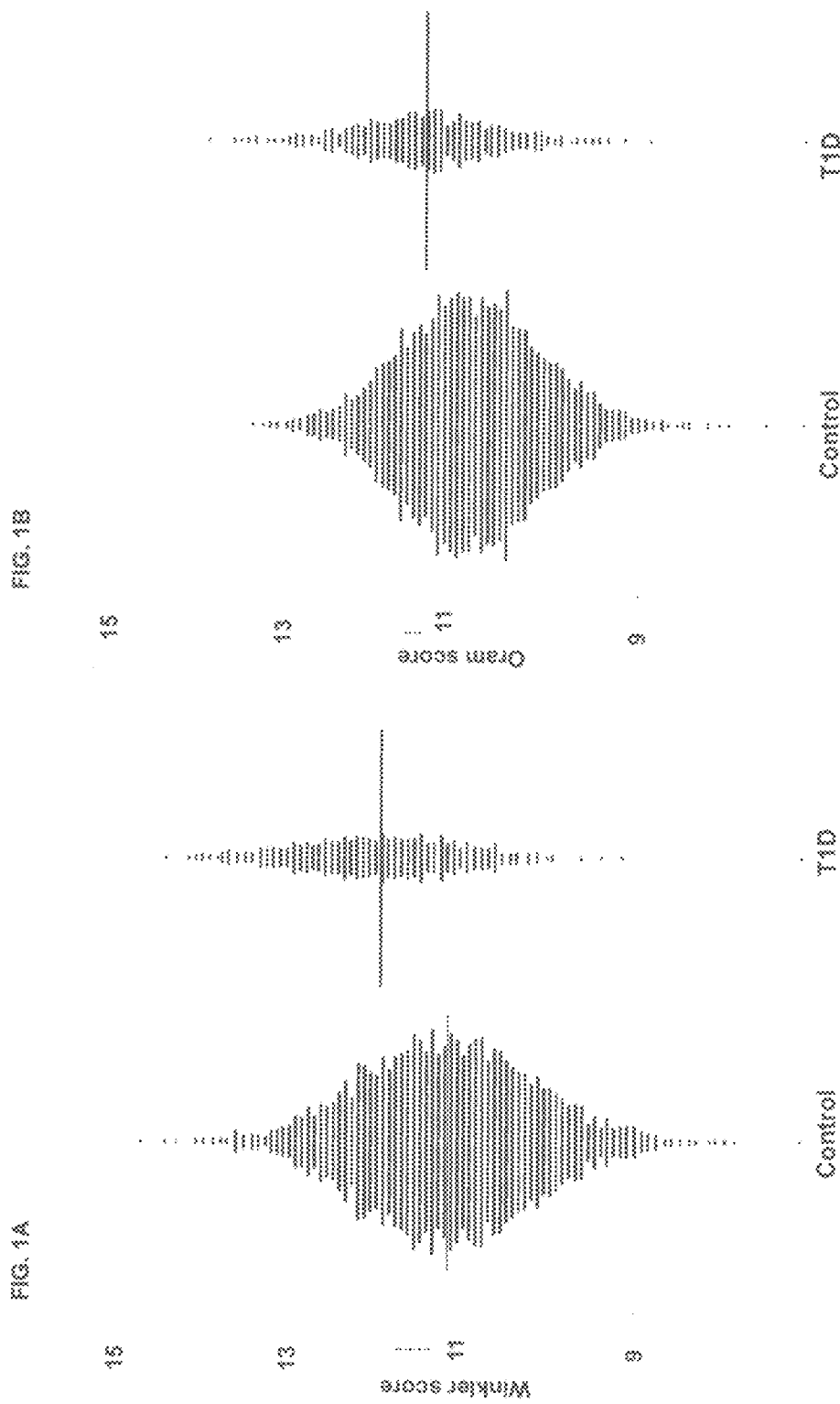

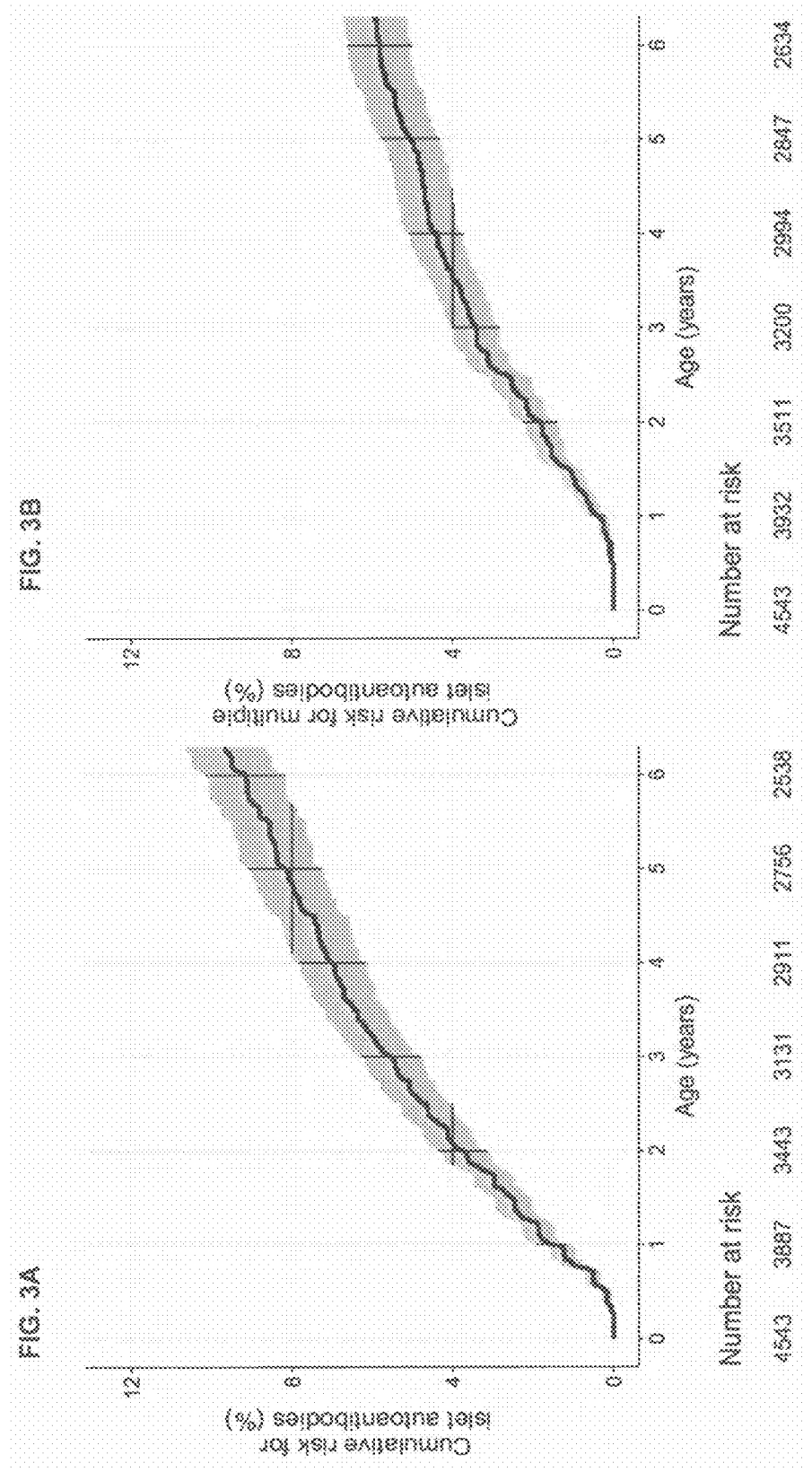

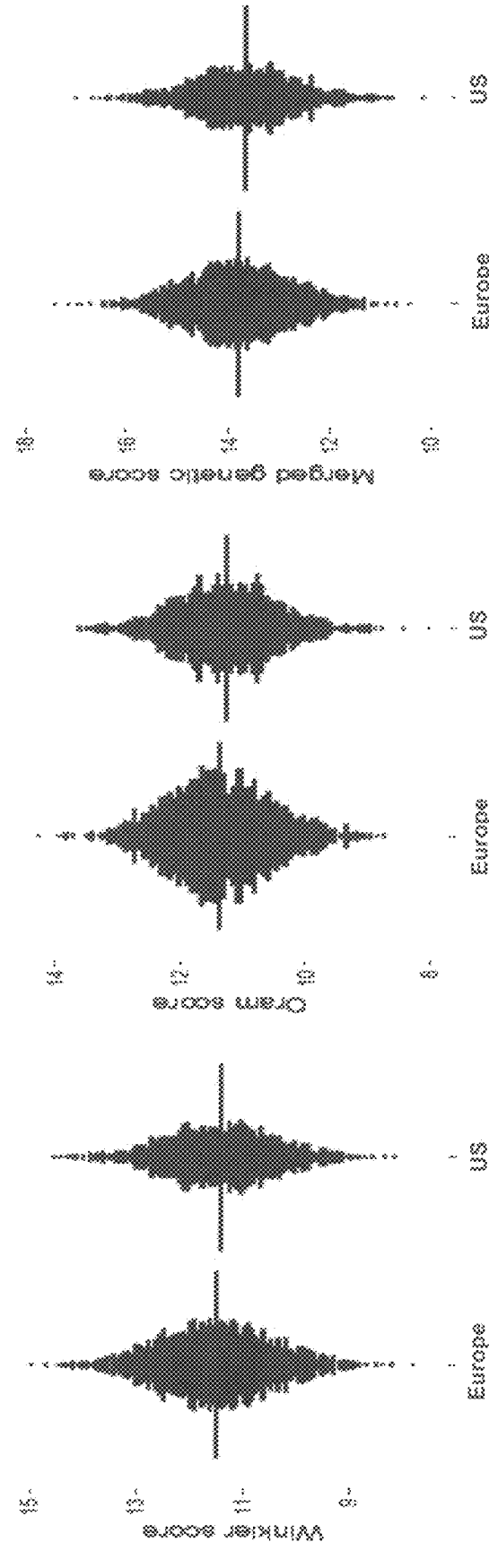

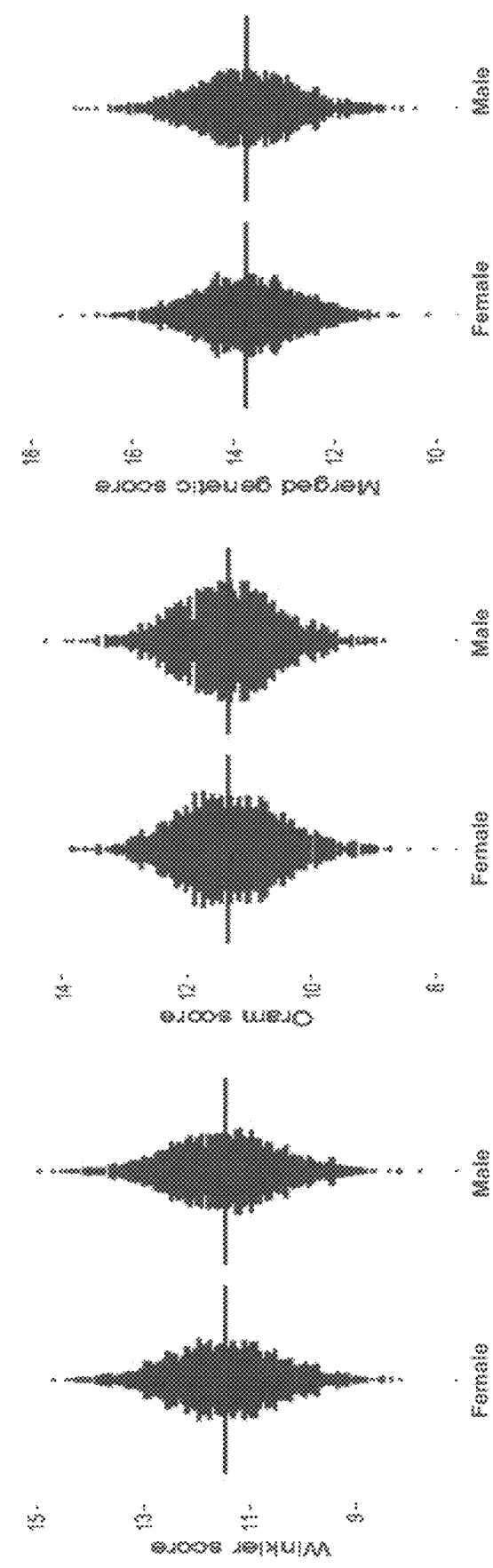

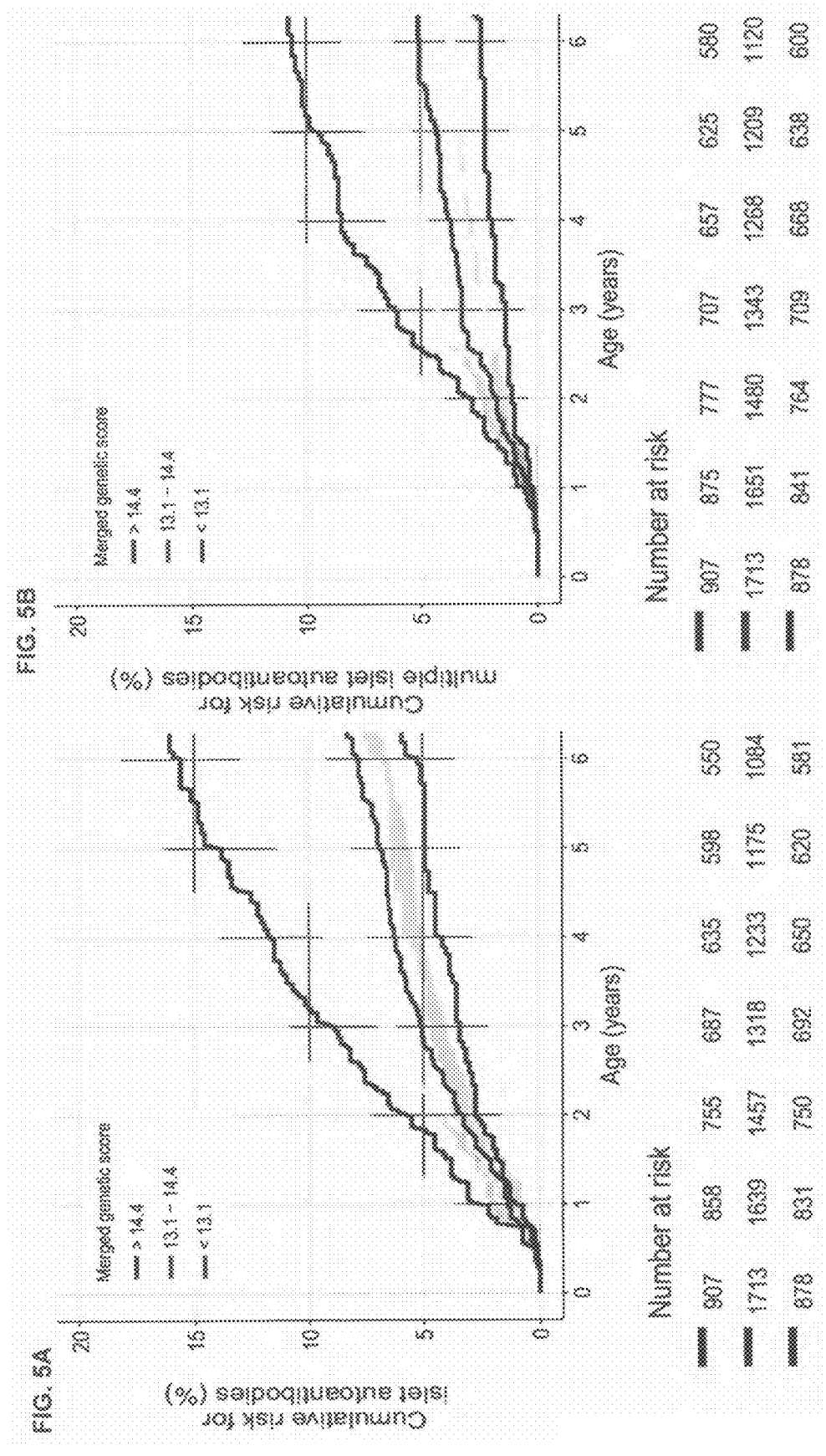

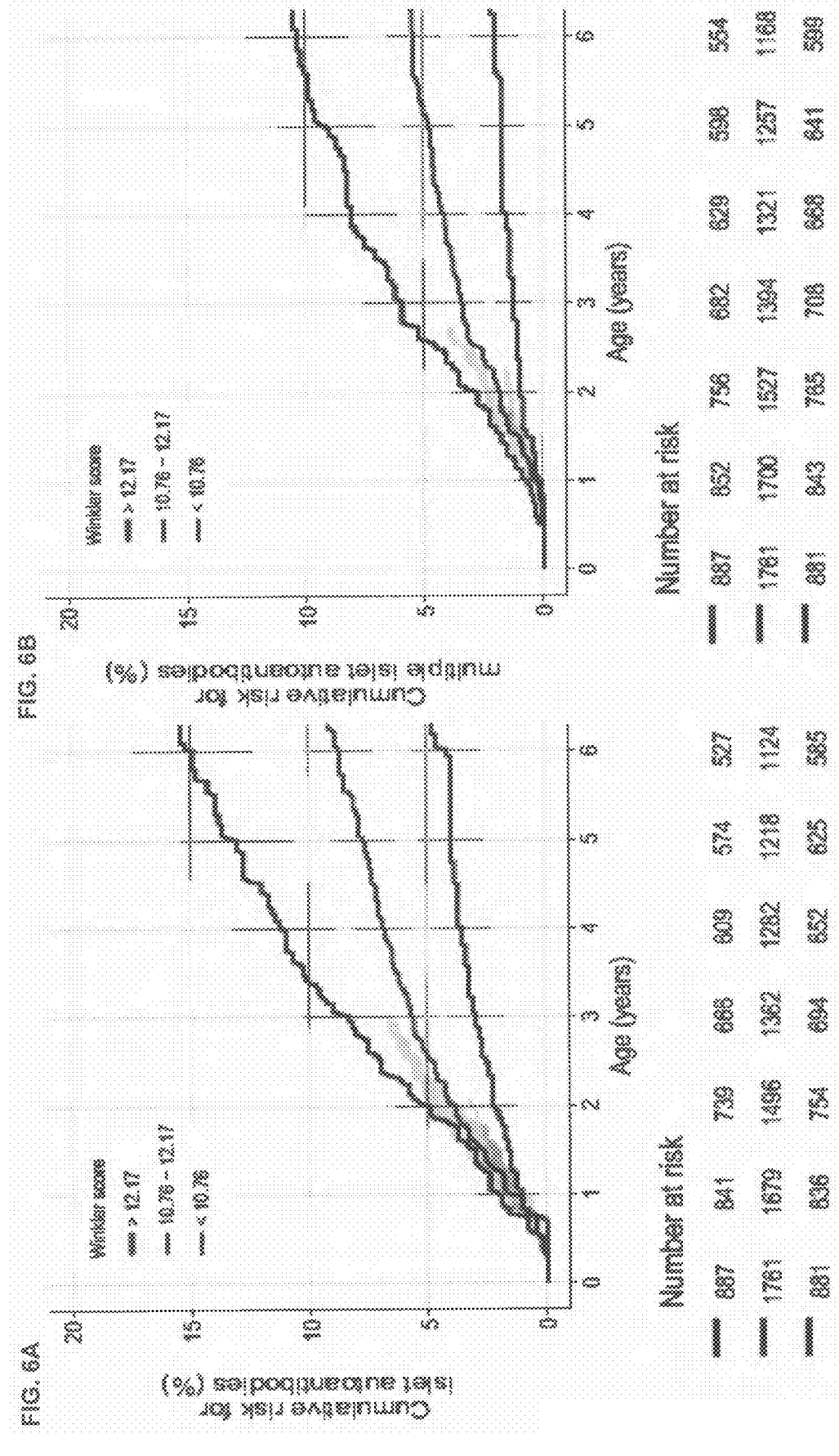

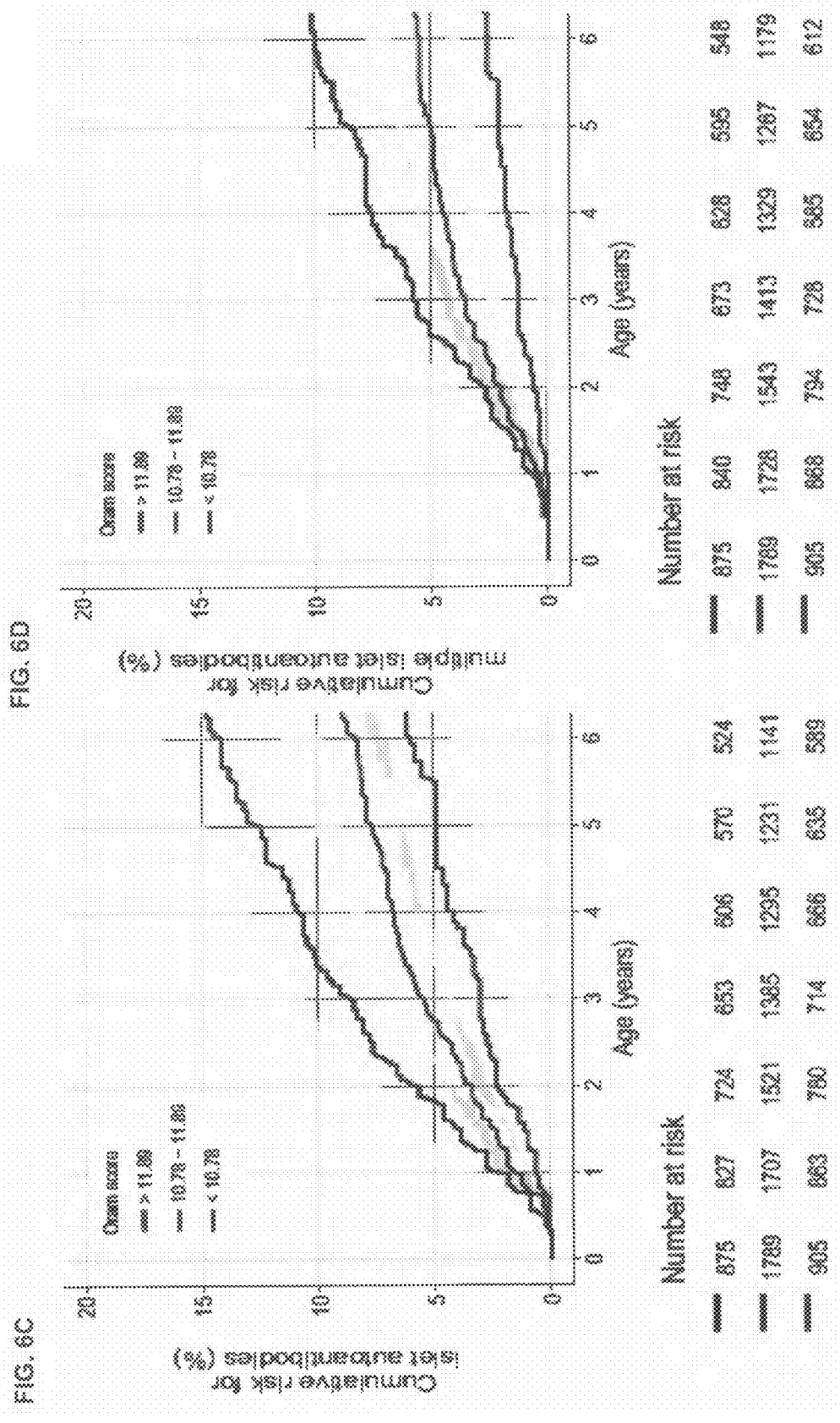

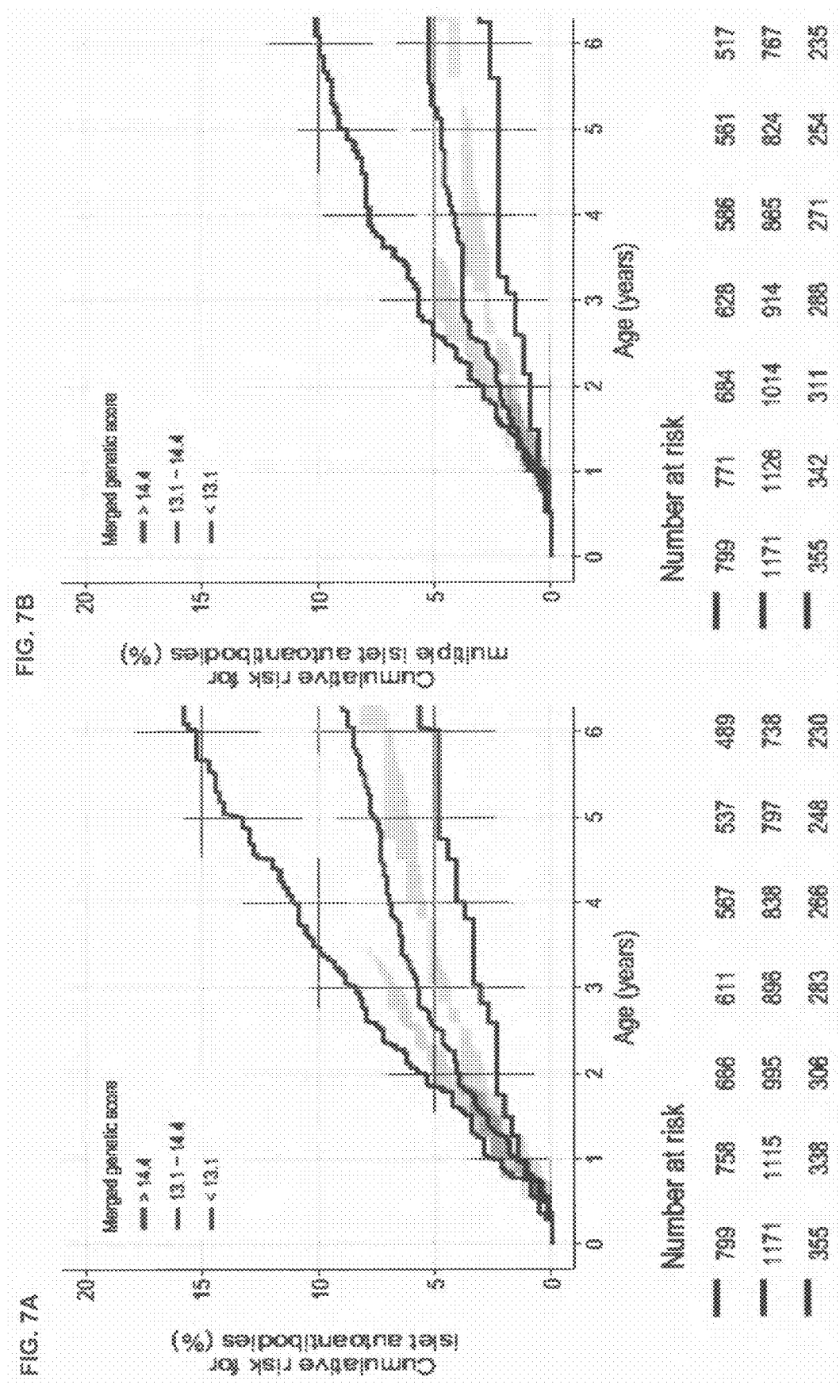

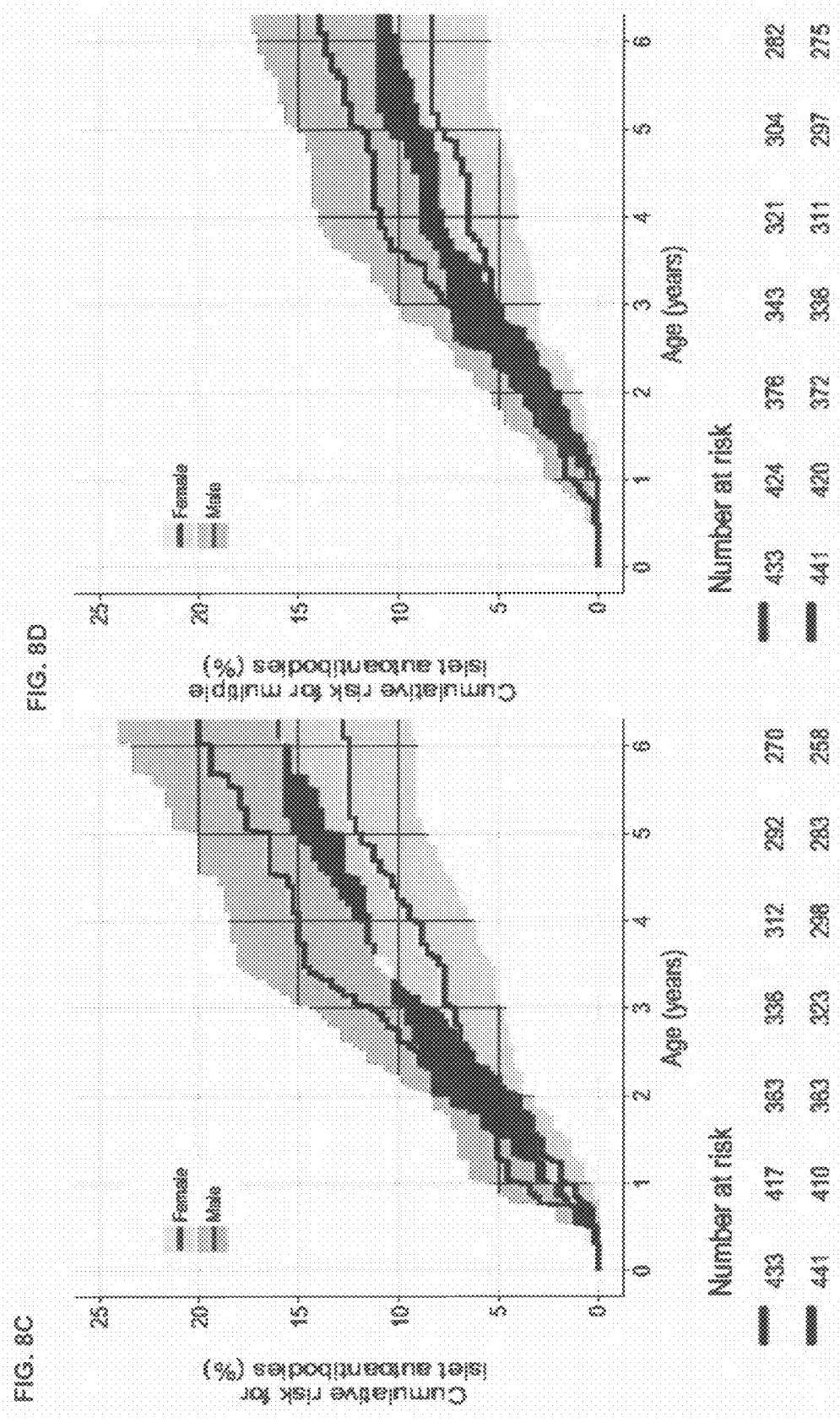

FIG. 10

| Risk score cut-off value | Cumulative risk (95% CI) | Sensitivity (95% CI) |
|---|---|---|
| 12.1 (5th centile) | 6.2 (5.3-7.0) % | 100 (97.8-100) % |
| 12.4 (10th centile) | 6.4 (5.5-7.4) % | 98.8 (95.9-99.7) % |
| 12.7 (15th centile) | 6.6 (5.6-7.6) % | 96.0 (91.9-98.0) % |
| 12.9 (20th centile) | 6.8 (5.7-7.8) % | 92.5 (87.6-95.6) % |
| 13.1 (25th centile) | 7.0 (5.9-8.1) % | 89.6 (84.2-93.3) % |
| 13.2 (30th centile) | 7.3 (6.2-8.4) % | 87.3 (81.5-91.5) % |
| 13.4 (35th centile) | 7.5 (6.3-8.7) % | 83.2 (77.0-88.1) % |
| 13.5 (40th centile) | 7.7 (6.5-9.0) % | 79.8 (73.2-85.1) % |
| 13.6 (45th centile) | 8.1 (6.7-9.4) % | 76.3 (69.4-82.0) % |
| 13.8 (50th centile) | 8.2 (6.8-9.6) % | 71.1 (63.9-77.3) % |
| 13.9 (55th centile) | 8.6 (7.1-10.1) % | 67.1 (59.7-73.6) % |
| 14.0 (60th centile) | 9.1 (7.5-10.8) % | 62.4 (55.0-69.3) % |
| 14.2 (65th centile) | 10.1 (8.2-11.9) % | 60.1 (52.7-67.1) % |
| 14.3 (70th centile) | 10.2 (8.2-12.2) % | 52.6 (45.2-59.9) % |
| 14.4 (75th centile) | 11.0 (8.7-13.3) % | 47.4 (40.1-54.8) % |
| 14.6 (80th centile) | 11.9 (9.2-14.5) % | 40.5 (33.4-47.9) % |
| 14.8 (85th centile) | 12.0 (8.9-15.1) % | 30.1 (23.7-37.3) % |
| 15.1 (90th centile) | 13.2 (9.2-17.1) % | 22.0 (16.4-28.7) % |
| 15.4 (95th centile) | 12.2 (6.7-17.4) % | 10.4 (6.7-15.8) % |

FIG. 12

| Risk score cut-off value | Cumulative risk (95% CI) | Sensitivity (95% CI) |
|---|---|---|
| 6.22 (5th centile) | 6.1 (5.2, 6.9) % | 100 (97.8, 100) % |
| 6.54 (10th centile) | 6.3 (5.3, 7.2) % | 98.2 (94.9, 99.4) % |
| 6.76 (15th centile) | 6.4 (5.5, 7.4) % | 94.7 (90.2, 97.2) % |
| 6.92 (20th centile) | 6.6 (5.6, 7.6) % | 91.2 (86.0, 94.6) % |
| 7.08 (25th centile) | 6.6 (5.5, 7.6) % | 85.3 (79.2, 89.8) % |
| 7.21 (30th centile) | 6.9 (5.8, 8.0) % | 83.5 (77.2, 88.4) % |
| 7.33 (35th centile) | 7.2 (6.0, 8.3) % | 80.6 (74.0, 85.8) % |
| 7.44 (40th centile) | 7.4 (6.2, 8.6) % | 77.1 (70.2, 82.7) % |
| 7.57 (45th centile) | 7.6 (6.3, 8.9) % | 72.4 (65.2, 78.5) % |
| 7.67 (50th centile) | 8.1 (6.7, 9.5) % | 70.0 (62.7, 76.4) % |
| 7.79 (55th centile) | 8.0 (6.5, 9.5) % | 62.4 (54.9, 69.3) % |
| 7.91 (60th centile) | 8.0 (6.4, 9.5) % | 55.3 (47.8, 62.6) % |
| 8.01 (65th centile) | 8.0 (6.3, 9.7) % | 48.2 (40.8, 55.7) % |
| 8.14 (70th centile) | 8.2 (6.4, 10.0) % | 42.4 (35.2, 49.9) % |
| 8.27 (75th centile) | 8.5 (6.5, 10.6) % | 36.5 (29.6, 43.9) % |
| 8.44 (80th centile) | 9.5 (7.1, 11.9) % | 32.4 (25.8, 39.7) % |
| 8.61 (85th centile) | 11.6 (8.5, 14.6) % | 29.4 (23.1, 36.7) % |
| 8.79 (90th centile) | 14.3 (10.1, 18.2) % | 24.1 (18.3, 31.1) % |
| 9.08 (95th centile) | 13.2 (7.4, 18.5) % | 11.2 (7.3, 16.8) % |

| Risk score cut-off value | Cumulative risk (95% CI) | Sensitivity (95% CI) |
|---|---|---|
| 9.72 (5th centile) | 6.0 (5.1, 6.9) % | 98.3 (95.0, 99.4) % |
| 10.08 (10th centile) | 6.2 (5.3, 7.2) % | 96.5 (92.6, 98.4) % |
| 10.36 (15th centile) | 6.5 (5.5, 7.5) % | 95.4 (91.1, 97.6) % |
| 10.59 (20th centile) | 6.7 (5.7, 7.7) % | 92.5 (87.6, 95.6) % |
| 10.76 (25th centile) | 7.1 (6.0, 8.1) % | 91.3 (86.2, 94.7) % |
| 10.92 (30th centile) | 7.0 (5.9, 8.1) % | 85.0 (78.9, 89.5) % |
| 11.05 (35th centile) | 7.3 (6.2, 8.5) % | 82.7 (76.3, 87.6) % |
| 11.19 (40th centile) | 7.7 (6.5, 9.0) % | 80.3 (73.8, 85.6) % |
| 11.32 (45th centile) | 8.2 (6.9, 9.5) % | 78.0 (71.3, 83.6) % |
| 11.46 (50th centile) | 8.5 (7.1, 10.0) % | 74.0 (67.0, 80.0) % |
| 11.60 (55th centile) | 8.9 (7.4, 10.4) % | 69.4 (62.1, 75.8) % |
| 11.74 (60th centile) | 9.2 (7.5, 10.8) % | 63.6 (56.2, 70.4) % |
| 11.89 (65th centile) | 9.7 (7.9, 11.5) % | 59.0 (51.5, 66.0) % |
| 12.02 (70th centile) | 10.4 (8.3, 12.4) % | 53.2 (45.8, 60.5) % |
| 12.17 (75th centile) | 10.3 (8.1, 12.5) % | 43.9 (36.7, 51.4) % |
| 12.37 (80th centile) | 10.1 (7.7, 12.6) % | 34.7 (28.0, 42.0) % |
| 12.55 (85th centile) | 9.5 (6.7, 12.3) % | 24.3 (18.5, 31.2) % |
| 12.78 (90th centile) | 11.2 (7.5, 14.8) % | 19.1 (13.9, 25.6) % |
| 13.16 (95th centile) | 9.9 (5.0, 14.5) % | 8.7 (5.3, 13.6) % |

FIG. 15

Figure 16:
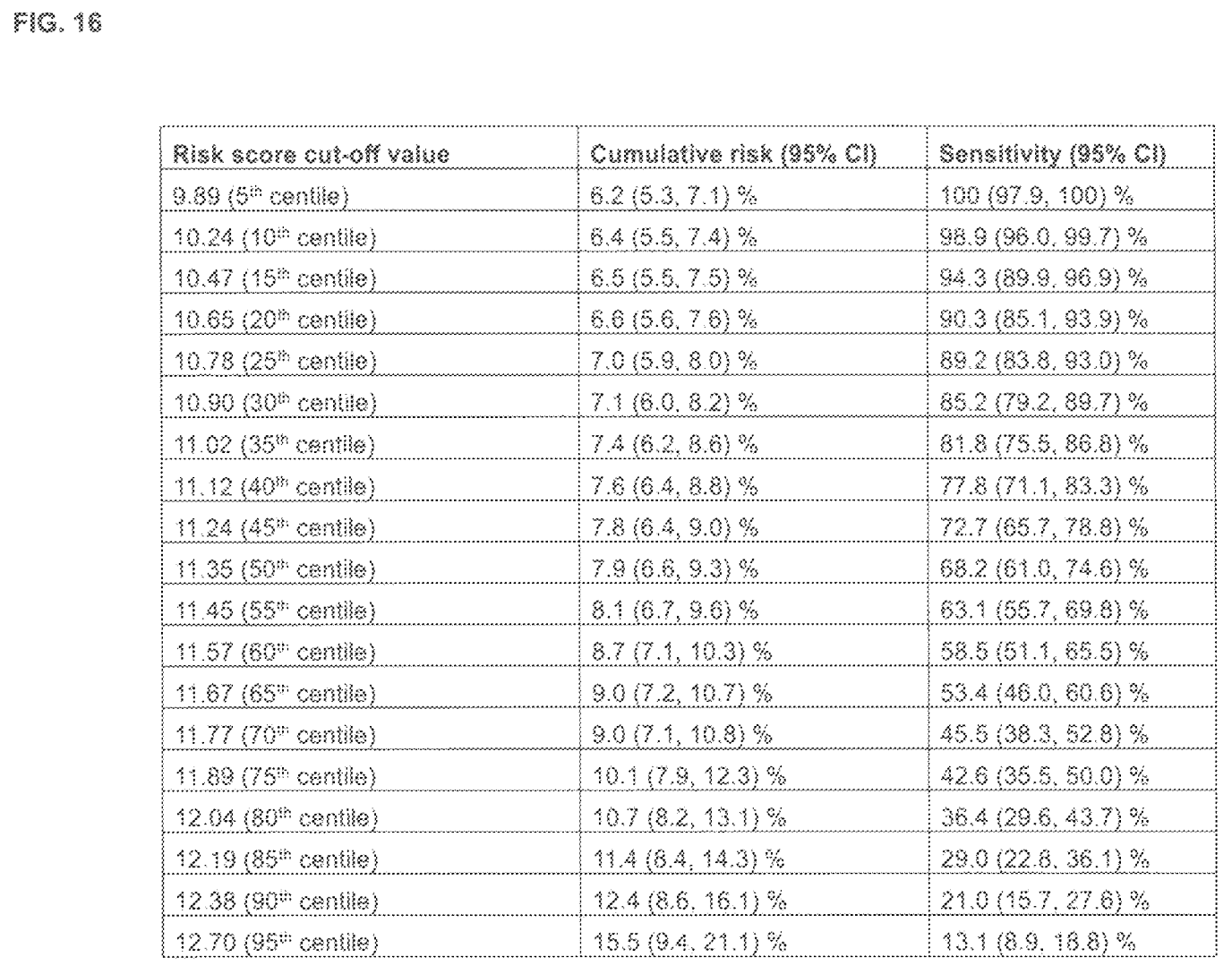

| Risk score cut-off value | Cumulative risk (95% CI) | Sensitivity (95% CI) |
|---|---|---|
| 9.89 (5th centile) | 6.2 (5.3, 7.1) % | 100 (97.9, 100) % |
| 10.24 (10th centile) | 6.4 (5.5, 7.4) % | 98.9 (96.0, 99.7) % |
| 10.47 (15th centile) | 6.5 (5.5, 7.5) % | 94.3 (89.9, 96.9) % |
| 10.65 (20th centile) | 6.6 (5.6, 7.6) % | 90.3 (85.1, 93.9) % |
| 10.78 (25th centile) | 7.0 (5.9, 8.0) % | 89.2 (83.8, 93.0) % |
| 10.90 (30th centile) | 7.1 (6.0, 8.2) % | 85.2 (79.2, 89.7) % |
| 11.02 (35th centile) | 7.4 (6.2, 8.6) % | 81.8 (75.5, 86.8) % |
| 11.12 (40th centile) | 7.6 (6.4, 8.8) % | 77.8 (71.1, 83.3) % |
| 11.24 (45th centile) | 7.8 (6.4, 9.0) % | 72.7 (65.7, 78.6) % |
| 11.35 (50th centile) | 7.9 (6.6, 9.3) % | 68.2 (61.0, 74.6) % |
| 11.45 (55th centile) | 8.1 (6.7, 9.6) % | 63.1 (55.7, 69.8) % |
| 11.57 (60th centile) | 8.7 (7.1, 10.3) % | 58.5 (51.1, 65.5) % |
| 11.67 (65th centile) | 9.0 (7.2, 10.7) % | 53.4 (46.0, 60.6) % |
| 11.77 (70th centile) | 9.0 (7.1, 10.8) % | 45.5 (38.3, 52.8) % |
| 11.89 (75th centile) | 10.1 (7.9, 12.3) % | 42.6 (35.5, 50.0) % |
| 12.04 (80th centile) | 10.7 (8.2, 13.1) % | 36.4 (29.6, 43.7) % |
| 12.19 (85th centile) | 11.4 (6.4, 14.3) % | 29.0 (22.6, 36.1) % |
| 12.38 (90th centile) | 12.4 (8.6, 16.1) % | 21.0 (15.7, 27.6) % |
| 12.70 (95th centile) | 15.5 (9.4, 21.1) % | 13.1 (8.9, 18.8) % |

| COMPARISON | BAYES FACTOR | STRENGTH OF EVIDENCE |
|---|---|---|
| RO VS. WI | 1.2 | - |
| RO VS. ME | 94 | Very strong |
| WI VS ME | 6.4 | Substantial |

FIG. 21

| | Model 1 | | Model 2 | | Model 3 | |
|---|---|---|---|---|---|---|
| | HR (95% CI) | p-value | HR (95% CI) | p-value | HR (95% CI) | p-value |
| Genetic risk score (per unit increase) | 1.22 (1.07, 1.40) | 0.003 | 1.48 (1.21, 1.81) | 0.0001 | 1.29 (1.03, 1.61) | 0.02 |
| HLA DR3/DR4 | 1.11 (0.81, 1.51) | 0.52 | 1.53 (0.96, 2.43) | 0.07 | 1.40 (0.86, 2.29) | 0.18 |
| Age at onset of previous event (per year) | 0.89 (0.83, 0.95) | 0.0003 | 0.70 (0.60, 0.82) | <0.0001 | 0.70 (0.59, 0.82) | <0.0001 |
| Finland | 0.83 (0.59, 1.18) | 0.31 | 1.09 (0.66, 1.78) | 0.74 | 0.95 (0.56, 1.63) | 0.86 |
| Germany | 0.67 (0.31, 1.40) | 0.32 | 0.41 (0.10, 1.73) | 0.23 | 0.43 (0.10, 1.80) | 0.25 |
| Sweden | 0.81 (0.58, 1.12) | 0.19 | 0.99 (0.62, 1.59) | 0.98 | 1.06 (0.64, 1.73) | 0.83 |

SEQUENCE LISTING

<160> NUMBER OF SEQ ID NOS: 42

<210> SEQ ID NO 1
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs1264813 = a/g

<400> SEQUENCE: 1
agagctgggg gcagagagca gggacctgtc tgtccccact rgatctggct gggggcaggg        60
gtgaggaata ggggtcagca g                                                  81

<210> SEQ ID NO 2
<211> LENGTH: 81
<212> TYPE: DNA
<213> ORGANISM: Homo sapiens
<220> FEATURE:
<221> NAME/KEY: misc_feature
<222> LOCATION: (41)..(41)

-continued

```
<223> OTHER INFORMATION: rs2395029 = g/t

<400> SEQUENCE: 2
cacccgctgg tctctggaca catactgtcc aattcccctg kggcagctgt aatgtgtagt       60
tcaatgggca ctcatttgtc c                                                 81

<210> SEQ ID NO 3
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2476601 = a/g

<400> SEQUENCE: 3
tcaccagctt cctcaaccac aataaatgat tcaggtgtcc rtacaggaag tggagggggg       60
atttcatcat ctatccttgg a                                                 81

<210> SEQ ID NO 4
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2816316 = g/t

<400> SEQUENCE: 4
gcagatctta tccagctccc tcctgttgtg gaggaatatt kagttgtctg ttgttttaga       60
taggatttcc atagctgcaa g                                                 81

<210> SEQ ID NO 5
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs3024505 = c/t

<400> SEQUENCE: 5
ggagagagga ggaaaaaaat gagctgagta aacactagtc yccctcacgc tctgcctggg       60
cagccctggt ctgggg aagg c                                                81

<210> SEQ ID NO 6
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs1990760 = c/t

<400> SEQUENCE: 6
tcaccattta tttgatagtc ggcacacttc ttttgcagtg ytttgttttc tcttacaatg       60
taaagttccc tataagtatc a                                                 81

<210> SEQ ID NO 7
<211> LENGTH: 81
<212> TYPE: DNA
<213> ORGANISM: Homo sapiens
<220> FEATURE:
<221> NAME/KEY: misc_feature
```

-continued

```
<222> LOCATION: (41)..(41)
<223> OTHER INFORMATION: rs3087243 = a/g

<400> SEQUENCE: 7
tctttccttt tgatttcttc accactattt gggatataac rtgggttaac acagacatag    60
cagtccttta taaatcaatt g                                              81

<210> SEQ ID NO 8
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs10517086 = a/g

<400> SEQUENCE: 8
tttgcatata tatatatttt ttacaaaaag gatggtcttg raaggttgtc ataaactcag    60
ggacacagga gttccgtctc a                                              81

<210> SEQ ID NO 9
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2069763 = g/t

<400> SEQUENCE: 9
gttctacaaa gaaaacacag ctacaactgg agcatttact kctggattta cagatgattt    60
tgaatggaat taatgtaagt a                                              81

<210> SEQ ID NO 10
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs6897932 = c/t

<400> SEQUENCE: 10
tattcttgct ttccagggga gatggatcct atcttactaa ycatcagcat tttgagtttt    60
ttctctgtcg ctctgttggt c                                              81

<210> SEQ ID NO 11
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs3757247 = a/g

<400> SEQUENCE: 11
aggcatggga accacttggg taaaggcatg gagatgggaa racattccag ggatagctat    60
taaccctttt taactgaagc a                                              81

<210> SEQ ID NO 12
<211> LENGTH: 81
<212> TYPE: DNA
<213> ORGANISM: Homo sapiens
<220> FEATURE:
```

-continued

```
<221> NAME/KEY: misc_feature
<222> LOCATION: (41)..(41)
<223> OTHER INFORMATION: rs9388489 = a/g

<400> SEQUENCE: 12
taaactcaga ttgcagaagg tgatagttaa atgccttgtt rgattttta gccagtgtga          60 gtctgttgta ccacaaaatt g                                                    81

<210> SEQ ID NO 13
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs6920220 = a/g

<400> SEQUENCE: 13
atctgcttcc atctgttagc aggtaacttc tccactaaaa rgatatggtt ctgtagaaca          60
atggcatatg cagacagtga t                                                    81

<210> SEQ ID NO 14
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs1738074 = a/g

<400> SEQUENCE: 14
gtctctctct ctcccagtgg actagaagga gcagagagtt rtgctgtttc tcccattctt          60
tacagctcac cggatgtaaa a                                                    81

<210> SEQ ID NO 15
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs7804356 = c/t

<400> SEQUENCE: 15
taaaataagg gtgtaaaggt agaaaggagg aaaaaggtta ygttcacaat gtgaccctac          60
attgactaga gagagagaca a                                                    81

<210> SEQ ID NO 16
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs4948088 = a/c

<400> SEQUENCE: 16
aagtgggtgc cacaacaaga catgagctag tcttgggata mccacctctg ctgccaggcc          60
aaaaagaaac ctctgatccc g                                                    81

<210> SEQ ID NO 17
<211> LENGTH: 81
<212> TYPE: DNA
<213> ORGANISM: Homo sapiens
```

```
<220> FEATURE:
<221> NAME/KEY: misc_feature
<222> LOCATION: (41)..(41)
<223> OTHER INFORMATION: rs7020673 = c/g

<400> SEQUENCE: 17
gagccttcca cacagtgata atggctacag attgctggag saaattcagg accttcagga        60
atacaccgct cgagggcaat a                                                   81

<210> SEQ ID NO 18
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs12722495 = a/g

<400> SEQUENCE: 18
atcacaatac cttcccttcc agttccttga atacttccaa rtcgcactta ggattgaaac        60
tcaccaaatt agagagatgg a                                                   81

<210> SEQ ID NO 19
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs947474 = a/g

<400> SEQUENCE: 19
aaaacactca caggacaatt ttcctaaccc ttggtctctc rgaatgctat tttttaggct        60
aatttgtttt gatgagaaaa c                                                   81

<210> SEQ ID NO 20
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs10509540 = c/t

<400> SEQUENCE: 20
atttgagcag gtaggatgtg attctgactc agagaaatta yatggtgtct ggaaaggggg        60
catgtgggat ctctgagtgt c                                                   81

<210> SEQ ID NO 21
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs689 = a/t

<400> SEQUENCE: 21
cagggcacct ggccttcagc ctgcctcagc cctgcctgtc wcccagatca ctgtccttct        60
gccatggccc tgtggatgcg c                                                   81

<210> SEQ ID NO 22
<211> LENGTH: 81
<212> TYPE: DNA
```

<213> ORGANISM: Homo sapiens
<220> FEATURE:
<221> NAME/KEY: misc_feature
<222> LOCATION: (41)..(41)
<223> OTHER INFORMATION: rs4763879 = a/g

<400> SEQUENCE: 22
taagtgaaca aattatggta tatccataca agggaattcc rctcagcaat tcaaaataag      60
acaactgata catgcaacaa a                                                81

<210> SEQ ID NO 23
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2292239 = a/c

<400> SEQUENCE: 23
tgtccccatc tgccaccta gatcccttaa gtgctgccct mtagattcaa aagtctcttc       60
actatttgtt gctacaagga g                                                81

<210> SEQ ID NO 24
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs3184504 = c/t

<400> SEQUENCE: 24
caagctacaa gcagcttgct ccagcatcca ggaggtccgg yggtgcacac ggcttgagat      60
gcctgacaac ctttacacct t                                                81

<210> SEQ ID NO 25
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs1465788 = a/g

<400> SEQUENCE: 25
agttgtcagt tgaccattta atggaagtct acactgaata rtcctttgcc aagtgaatag      60
ccccggaatt tgttttgtgg t                                                81

<210> SEQ ID NO 26
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs17574546 = a/c

<400> SEQUENCE: 26
aattcgtact cccaccatgt tgtttccttc tttcatcctc mggtatggta atctagaatc      60
aataatttgt tttgttttca c                                                81

<210> SEQ ID NO 27
<211> LENGTH: 81

```
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs3825932 = c/t

<400> SEQUENCE: 27
cagggtttga gtttaggaca attgactacc agtttgcctc yggagagatt attctggggc      60
cagaataatc tgctggtgaa c                                                81

<210> SEQ ID NO 28
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs12708716 = a/g

<400> SEQUENCE: 28
cgggtcttca gctagtcctc tgggcagtag ggagaatcct ragtaatagc cgcttcacag      60
ggagtcagtg aggatgaagt g                                                81

<210> SEQ ID NO 29
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs4788084 = a/g

<400> SEQUENCE: 29
cctgatttct agggagttct gtggccttca gggagtccca rgggagcaag attagagcac      60
ccagtccctg agtgccctgc t                                                81

<210> SEQ ID NO 30
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs7202877 = c/g/t

<400> SEQUENCE: 30
tcaggcgcgc tccgaactcc gagtgggcgt cttctgtgac bgtcagggcg tgtgtggctt      60
tttagggctg gccggtgggg c                                                81

<210> SEQ ID NO 31
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2290400 = a/g

<400> SEQUENCE: 31
agcgattaat cttcaatagg agctggctca cagagaggga raagagtcag tgggaggtaa      60
ggccctgaga tccttaactc t                                                81

<210> SEQ ID NO 32
```

```
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs7221109 = c/t

<400> SEQUENCE: 32
ttgcccagct tctattctgt aatatattgt attagtcact yggggcacaa atatgaaagc      60
caacacatat ttcttcagga c                                               81

<210> SEQ ID NO 33
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs45450798 = c/g

<400> SEQUENCE: 33
catctctgcc ttgtctcttt atatgccaca taagatttct scataaggct taagtatttt      60 aaaggggggca gttatcattt a                                              81

<210> SEQ ID NO 34
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs763361 = a/c/t

<400> SEQUENCE: 34
tcctctcttg tatcatccat ggattgattg gtaggttgac hggtagagat gggacttcta      60
tagttattgg gtgcctagaa a                                              81

<210> SEQ ID NO 35
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs425105 = a/g

<400> SEQUENCE: 35
aggagttttg gggaggacta gaaggaggtg cttaccatag rggactgggg ctgggtcaga      60
gctttggcgg ggacttttga g                                              81

<210> SEQ ID NO 36
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2281808 = c/t

<400> SEQUENCE: 36
tcccatttgg gtttctcaac attagtttac aatgtggatt yctctgaccc catggagtcc      60
cagcattcaa ataatctaca g                                              81
```

-continued

```
<210> SEQ ID NO 37
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs3788013 = a/c

<400> SEQUENCE: 37
ggtgaaaaaa gagaaaagct gctcagcctc atgggtgtgc mtgttggggt ggagctcttg      60
caggtgtcaa gactgatggt t                                                81

<210> SEQ ID NO 38
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs5753037 = c/t

<400> SEQUENCE: 38
ccaggtatca gtattattgt aatattccct ttatcaaaaa yctataactg aaatttatag      60
gtaagagttt acagtaagca g                                                81

<210> SEQ ID NO 39
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs229541 = c/t

<400> SEQUENCE: 39
ataggggstt aaaggcccct cttagtgaag ggcaaagatg yttatcagaa attgggttag      60
aggcccaaat gaagaaggtt g                                                81

<210> SEQ ID NO 40
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs5979785 = c/t

<400> SEQUENCE: 40
tgtaattctc atattactat cattgttatg tattctttct ytccgaatga agaatgaagg      60
taccatccac tgacaccaca g                                                81

<210> SEQ ID NO 41
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs2664170 = a/g

<400> SEQUENCE: 41
gtcacagtgt ttttcaacca gggatggtat aattcctctc rggagcatct gaaaatatgt      60
gggttttgct tgttataaag g                                                81
```

-continued

```
<210> SEQ ID NO 42
<211> LENGTH: 81
<212> TYPE: DNA
<213> ORGANISM: Homo sapiens
<220> FEATURE:
<221> NAME/KEY: misc_feature
<222> LOCATION: (41)..(41)
<223> OTHER INFORMATION: rs1004446 = c/t

<400> SEQUENCE: 42
ggatggggtg tgcaggaaag gccattgtgg agagggttct yctttagggc tgcacaaagc            60
cactgaggct tttgcaagga a                                                      81
```

METHOD FOR DETERMINING THE RISK TO DEVELOP TYPE 1 DIABETES

CROSS-REFERENCE TO RELATED APPLICATIONS

This application is a U.S. national phase application of International PCT Patent Application Serial No. PCT/EP2018/067240, filed Jun. 27, 2018, which claims priority to European Application No. 17178396.2, filed Jun. 28, 2017, and Luxembourg Application No. 100334, filed Jul. 13, 2017, which are incorporated herein by reference in their entirety.

This application contains a Sequence Listing in computer readable form, which is incorporated herein by reference.

TECHNICAL FIELD OF THE INVENTION

The present invention relates to a method of determining whether a subject is at risk of developing type 1 diabetes by determining the genetic risk score (GRS) of a subject. The present invention also comprises a pharmaceutical composition comprising insulin and a pharmaceutical acceptable carrier for use in a method for preventing type 1 diabetes in a patient having a genetic risk score as determined by the method mentioned above. Further, it encompasses a kit for use in a method of determining whether a subject is at risk of developing type 1 diabetes by determining the genetic risk score of a subject as determined by the method of the present invention. Additionally, a type 1 diabetes antigen for use in a method of immunizing a subject against type 1 diabetes having a genetic risk score as determined by the method of the present invention is also comprised.

BACKGROUND ART

Precision medicine usually relies on our ability to identify individuals with precise genetic elements, which define a disease. These elements may also be used to identify individuals who may benefit from interventions aimed at disease prevention. Most ongoing studies aimed at understanding disease etiology and clinical trials aimed at preventing childhood diseases, such as allergy, type 1 diabetes, and celiac disease, rely on identifying and enrolling infants with increased risk of the disease[17]. The risk is usually assessed in terms of family history[1,3-7], which correctly identifies up to 10% of children who subsequently develop the disease.[7,8]

Genotypes in the human leukocyte antigen (HLA) DR and DQ loci are sometimes used to identify at-risk infants with or without a family history. These at-risk infants could be enrolled in studies aimed at identifying children who are likely to develop autoantibodies before the clinical manifestation of diabetes[2,9,10]. The risk of type 1 diabetes was predicted to be 5% in children with the HLA DR3/4-DQ8 and DR4-DQ8/DR4-DQ8 genotypes without first-degree relatives with diabetes[11]. Although the HLA loci are the strongest genetic risk markers for type 1 diabetes, other regions of the genome also confer susceptibility to type 1 diabetes[12]. Therefore, it is conceivable that risk stratification could be improved if risk is calculated according to genetic information derived from multiple genetic susceptibility regions.

Some researchers have questioned the utility of combining genetic markers for predicting the development of type 1 diabetes[13]. However, multi-loci genetic scores were developed in two case-control cohort studies to identify cases of type 1 diabetes, or discriminates between type 1 and type 2 diabetes[14,15].

Yet, this approach to identify cases of type 1 diabetes from the prior art did not fully satisfy the need to perfectly establish genetic scores, which precisely predict the risk to develop type 1 diabetes.

Thus, the objective of the present invention is the provision of a method to determine the degree to which type 1 diabetes genetic scores stratify the probability for developing type 1 diabetes.

SUMMARY OF THE INVENTION

Even though the prior art provides evidence that multi-loci genetic scores are developed suggesting an approach to identify cases of type 1 diabetes, the risk stratification strategy for developing type 1 diabetes, and particularly pre-symptomatic type 1 diabetes cited by the prior art is insufficient to establish genetic risk scores, which precisely predict the risk to develop type 1 diabetes.

The solution of the present invention is a method of determining whether a subject is at risk of developing type 1 diabetes by determining the genetic risk score (GRS) of a subject by (a) multiplying the score weight of 41 SNPs, if determined in a sample from said subject with the number of risk alleles for each SNP, if determined, wherein the 41 SNPs and their corresponding score weight are selected from the following ones

TABLE 1

Overview of the 41 non HLA class II SNPs of the merged score.

| SNP | score weight per allele |
|---|---|
| rs1264813 | 0.43 |
| rs2395029 | 0.92 |
| rs2476601 | 0.76 |
| rs2816316 | 0.16 |
| rs3024505 | 0.22 |
| rs1990760 | 0.16 |
| rs3087243 | 0.16 |
| rs10517086 | 0.19 |
| rs2069763 | 0.11 |
| rs6897932 | 0.19 |
| rs3757247 | 0.19 |
| rs9388489 | 0.14 |
| rs6920220 | 0.15 |
| rs1738074 | 0.05 |
| rs7804356 | 0.15 |
| rs4948088 | 0.17 |
| rs7020673 | 0.23 |
| rs12722495 | 0.47 |
| rs947474 | 0.15 |
| rs10509540 | 0.25 |
| rs689 or rs1004446 | 0.65 |
| rs4763879 | 0.06 |
| rs2292239 | 0.36 |
| rs3184504 | 0.24 |
| rs1465788 | 0.13 |
| rs17574546 | 0.13 |
| rs3825932 | 0.15 |
| rs12708716 | 0.15 |
| rs4788084 | 0.20 |
| rs7202877 | 0.19 |
| rs2290400 | 0.25 |
| rs7221109 | 0.15 |
| rs45450798 | 0.09 |
| rs763361 | 0.12 |
| rs425105 | 0.21 |
| rs2281808 | 0.07 |
| rs3788013 | 0.16 |

TABLE 1-continued

Overview of the 41 non HLA class II SNPs of the
merged score.

| SNP | score weight per allele |
|---|---|
| rs5753037 | 0.15 |
| rs229541 | 0.18 |
| rs5979785 | 0.09 |
| rs2664170 | 0.14 | and wherein a risk allele is determined by assigning the
number 0, if the determined SNP is a non-risk allele,
and by assigning the number 1, if the determined SNP
is present heterozygously, and by assigning the number
2, if the determined SNP is present homozygously,
thereby obtaining multiplication products;

(b) assigning the score number 3.15 if SNP rs17426593,
SNP rs2187668, and SNP rs7454108 are determined in
a subject having a HLA DR4-DQ8/DR4-DQ8 genotype
and the score number 3.98 if SNP rs17426593, SNP
rs2187668, and SNP rs7454108 are determined in a
subject having a HLA DR3/DR4-DQ8 genotype; (c)
summing up multiplication products of step a) and the
score number of step b), thereby obtaining a genetic
risk score; wherein the genetic risk score is indicative
that a subject is at risk of developing type 1 diabetes.

Further, the present invention relates to a pharmaceutical
composition comprising insulin and a pharmaceutical
acceptable carrier for use in a method for preventing type 1
diabetes in a subject having a genetic risk score as deter-
mined by the method mentioned above.

Additionally, the present invention comprises a kit for use
in a method of determining whether a subject is at risk of
developing type 1 diabetes by determining the genetic risk
score (GRS) of a subject according to the method of the
present invention, the kit comprising means for analyzing 41
SNPs as listed in Table 1 in a sample from a subject and
determining, whether the determined SNP is present het-
erozygously or whether the determined SNP is present
homozygously, and further comprising means for detecting
whether said subject, whose sample is investigated, has a
HLA DR4-DQ8/DR4-DQ8 genotype or whether said subject
has a HLA DR3/DR4-DQ8 genotype.

The present invention further encompasses a type 1
diabetes antigen for use in a method of immunizing a subject
against type 1 diabetes having a genetic risk score as
determined by the method of the present invention.

BRIEF DESCRIPTION OF THE FIGURES

FIGS. 1A-1C: Genetic scores calculated using the Win-
kler model (FIG. 1A) and the Oram model (FIG. 1B) in the
UK Biobank and Wellcome Trust Case Control Cohort
(WTTC) controls, and in WTTC cases with the HLA DR3/
DR4-DQ8 or DR4-DQ8/DR4-DQ8 genotypes. (FIG. 1C)
The empirically calculated risk of type 1 diabetes (y axis)
and the proportion of all cases of type 1 diabetes in each
cohort (x axis) is shown for both genetic scores.

FIGS. 3A-3B: Development of islet autoantibodies (FIG.
3A) and multiple islet autoantibodies (FIG. 3B) in TEDDY
children with the HLA DR3/DR4-DQ8 or DR4-DQ8/DR4-
DQ8 genotypes. The cumulative frequency of positive chil-
dren (y axis) is shown relative to the age of the children (x
axis). The shaded area represents the 95% confidence interval of the cumulative frequency. The numbers indicate the
number of children included in the analysis at each age.

FIGS. 4A-4C: Genetic scores in TEDDY children accord-
ing to their islet autoantibody outcome (FIG. 4A), location
(FIG. 4B), and sex (FIG. 4C). The scores were calculated
using the Winkler (left panels), Oram (middle panels), and
TEDDY (right panels) models.

FIGS. 5A-5B: Cumulative frequencies of islet autoanti-
body (FIG. 5A) and multiple islet autoantibody (FIG. 5B)
development in TEDDY children with the HLA DR3/DR4-
DQ8 or DR4-DQ8/DR4-DQ8 genotypes stratified by their
TEDDY score. The frequency (y axis) is shown relative to
the age in years (x axis). Curves are shown for children with
a merged genetic score of above 14.4 (upper line), below
13.1 (lower line), and between 13.1 and 14.4 (middle line).
The shaded areas represent the 95% confidence interval of
the cumulative frequency. The numbers indicate the number
of children included in the analysis at each age.

FIGS. 6A-6D: Cumulative frequencies of developing islet
autoantibodies (FIG. 6A and FIG. 6C) and multiple islet
autoantibodies (FIG. 6B and FIG. 6D) in TEDDY children
with the HLA DR3/DR4-DQ8 or DR4-DQ8/DR4-DQ8
genotypes stratified by their Winkler (FIG. 6A and FIG. 6B)
and Oram (FIG. 6C and FIG. 6D) genetic scores. The
frequency (y axis) is shown relative to the age in years (x
axis). Curves are shown for children with a genetic score of
above 12.17 (upper line), below 10.76 (lower line), and
between 10.76 and 12.17 (middle line) for the Winkler score
and with a genetic score of above 11.89 (upper line), below
10.78 (lower line), and between 10.78 and 11.89 (middle
line) for the Oram score The shaded areas represent the 95%
confidence interval of the cumulative frequency. The num-
bers indicate the number of children included in the analysis
at each age.

FIGS. 7A-7D: Cumulative frequencies of developing islet
autoantibodies (FIG. 7A and FIG. 7C) and multiple islet
autoantibodies (FIG. 7B and FIG. 7D) in TEDDY children
with the HLA DR3/DR4-DQ8 (FIG. 7A and FIG. 7B) or
DR4-DQ8/DR4-DQ8 (FIG. 7C and FIG. 7D) genotypes.
The frequency (y axis) is shown relative to the age in years
(x axis). Curves are shown for children with a merged
genetic score of above 14.4 (upper line), below 13.1 (lower
line), and between 13.1 and 14.4 (middle line). The shaded
areas represent the 95% confidence interval of the cumula-
tive frequency. The numbers indicate the number of children
included in the analysis at each age.

FIGS. 8A-8D: Cumulative frequencies of the develop-
ment of islet autoantibodies (FIG. 8A and FIG. 8C) and
multiple islet autoantibodies (FIG. 8B and FIG. 8D) in
TEDDY children with the HLA DR3/DR4-DQ8 or DR4-
DQ8/DR4-DQ8 genotypes and TEDDY scores >14.4.
Curves are shown for children divided by location (FIG. 8A
and FIG. 8B; Europe, upper lines; USA, lower lines) and sex
(FIG. 8C and FIG. 8D; boys, upper lines; girls, lower lines).
The shaded areas represent the 95% confidence interval of
the cumulative frequency. The numbers indicate the number
of children included in the analysis at each age.

FIG. 9B) in TEDDY children
with the HLA DR3/DR4-DQ8 or DR4-DQ8/DR4-DQ8
genotypes stratified by their TEDDY score using 41 non-
HLA class II SNPs from Table 1. The risk and sensitivity are
shown for each increment in the genetic score by the 5th
percentile of scores in the TEDDY children with the HLA
DR3/DR4-DQ8 or DR4-DQ8/DR4-DQ8 genotypes ranging
from >12.1 (lower 5th percentile of children) to >15.4 (upper $5^{th}$ percentile of children). The risk and sensitivity are shown for the development of islet autoantibodies (left panels) and multiple islet autoantibodies (right panels).

FIG. 10: Risk of developing multiple islet autoantibodies and the proportion of cases positive for multiple islet autoantibodies (sensitivity) in TEDDY children with the HLA DR3/DR4-DQ8 or DR4-DQ8/DR4-DQ8 genotypes stratified by their TEDDY score using 41 non-HLA class II SNPs from Table 1, with corresponding 95% confidence intervals (CIs). The risk and sensitivity are shown for each increment in the genetic score by the 5th percentile of scores in the TEDDY children with the HLA DR3/DR4-DQ8 or DR4-DQ8/DR4-DQ8 genotypes ranging from >12.1 (lower 5th percentile of children) to >15.4 (upper 5th percentile of children).

FIG. 11B) in TEDDY children with the HLA DR3/DR4-DQ8 or DR4-DQ8/DR4-DQ8 genotypes stratified by their TEDDY score using 12 non-HLA class II SNPs from Table 3 (yellow marked SNPs). The risk and sensitivity are shown for each increment in the genetic score by the $5^{th}$ percentile of scores in the TEDDY children with the HLA DR3/DR4-DQ8 or DR4-DQ8/DR4-DQ8 genotypes ranging from >6.22 (lower $5^{th}$ percentile of children) to >9.08 (upper $5^{th}$ percentile of children). The risk and sensitivity are shown for the development of multiple islet autoantibodies.

FIG. 12: Risk of developing multiple islet autoantibodies and the proportion of cases positive for multiple islet autoantibodies (sensitivity) in TEDDY children with the HLA DR3/DR4-DQ8 or DR4-DQ8/DR4-DQ8 genotypes stratified by their TEDDY score using 12 non-HLA class II SNPs from Table 3 (yellow marked SNPs), with corresponding 95% confidence intervals (CIs). The risk and sensitivity are shown for each increment in the genetic score by the 5th percentile of scores in the TEDDY children with the HLA DR3/DR4-DQ8 or DR4-DQ8/DR4-DQ8 genotypes ranging from >6.22 (lower 5th percentile of children) to >9.08 (upper 5th percentile of children).

FIG. 13C and FIG. 13D) in TEDDY children with the HLA DR3/DR4-DQ8 or DR4-DQ8/DR4-DQ8 genotypes stratified according to the Winkler (FIG. 13A and FIG. 13C) and Oram (FIG. 13B and FIG. 13D) genetic score. The risk and sensitivity are shown for each increment in genetic score by the $5^{th}$ percentile of the scores in the TEDDY children with the HLA DR3/DR4-DQ8 or DR4-DQ8/DR4-DQ8 genotypes with Winkler scores ranging from >9.72 (lower $5^{th}$ percentile of children) to >13.16 (upper $5^{th}$ percentile of children) and Oram scores ranging from >9.89 (lower $5^{th}$ percentile of children) to >12.70 (upper $5^{th}$ percentile of children).

FIG. 14C and FIG. 14D) in TEDDY children with the HLA DR3/DR4-DQ8 or DR4-DQ8/DR4-DQ8 genotypes stratified according to the Winkler (FIG. 14A and FIG. 14C) and Oram (FIG. 14B and FIG. 14D) genetic score. The risk and sensitivity are shown for each increment in genetic score by the $5^{th}$ percentile of the scores in the TEDDY children with the HLA DR3/DR4-DQ8 or DR4-DQ8/DR4-DQ8 genotypes with Winkler scores ranging from >9.72 (lower $5^{th}$ percentile of children) to >13.16 (upper $5^{th}$ percentile of children) and Oram scores ranging from >9.89 (lower $5^{th}$ percentile of children) to >12.70 (upper $5^{th}$ percentile of children).

FIG. 15: Risk of developing multiple islet autoantibodies and the proportion of cases positive for multiple islet autoantibodies (sensitivity) in TEDDY children with the HLA DR3/DR4-DQ8 or DR4-DQ8/DR4-DQ8 genotypes stratified by their Winkler Score using 38 of the 39 non-HLA class II Winkler SNPs, with corresponding 95% confidence intervals (CIs). The risk and sensitivity are shown for each increment in the genetic score by the 5th percentile of scores in the TEDDY children with the HLA DR3/DR4-DQ8 or DR4-DQ8/DR4-DQ8 genotypes ranging from >9.72 (lower 5th percentile of children) to >13.16 (upper 5th percentile of children).

FIG. 16: Risk of developing multiple islet autoantibodies and the proportion of cases positive for multiple islet autoantibodies (sensitivity) in TEDDY children with the HLA DR3/DR4-DQ8 or DR4-DQ8/DR4-DQ8 genotypes stratified by their Oram Score using 26 of the 27 non-HLA class II Oram SNPs, with corresponding 95% confidence intervals (Cis). The risk and sensitivity are shown for each increment in the genetic score by the 5th percentile of scores in the TEDDY children with the HLA DR3/DR4-DQ8 or DR4-DQ8/DR4-DQ8 genotypes ranging from >9.89 (lower 5th percentile of children) to >12.70 (upper 5th percentile of children).

FIG. 19: Assessing significance of the time-dependent discrimination accuracy of the genetic risk scores (RO=Oram score, WI=Winkler score, ME=merged score) using Bayes factors. A Bayes factor <3 was denoted as genetic risk scores are statistically indistinguishable.

FIG. 21: Hazard ratios (HRs) and 95% confidence intervals (CIs) of development of multiple islet autoantibodies after first appearance of any autoantibodies (model 1), development of type 1 diabetes after first appearance of any autoantibodies (model 2), and development of type 1 diabetes after first appearance of multiple autoantibodies (model 3) in children with the HLA DR3/DR4-DQ8 or the HLA DR4-DQ8/DR4-DQ8 genotype (reference), with mutual adjustment for the genetic risk score (only non-HLA SNPs), HLA genotype, age at onset of the previous event (i.e. of any islet autoantibodies in models 1 and 2, and of multiple islet autoantibodies in model 3), and country (reference: US).

DETAILED DESCRIPTION OF THE INVENTION

The solution of the present invention is described in the following, exemplified in the appended examples, illustrated in the figures and reflected in the claims.

Even though established genetic scores were available from Winkler et al. (2014) and Oram et al. (2016), the skilled person in the art was not able to a make a precise prediction of the onset of type 1 diabetes in a subject at a certain age vice versa the prior art was not able to predict the risk to develop type 1 diabetes at a certain age according to a certain genetic risk score obtained by the present invention.

Figure 17:
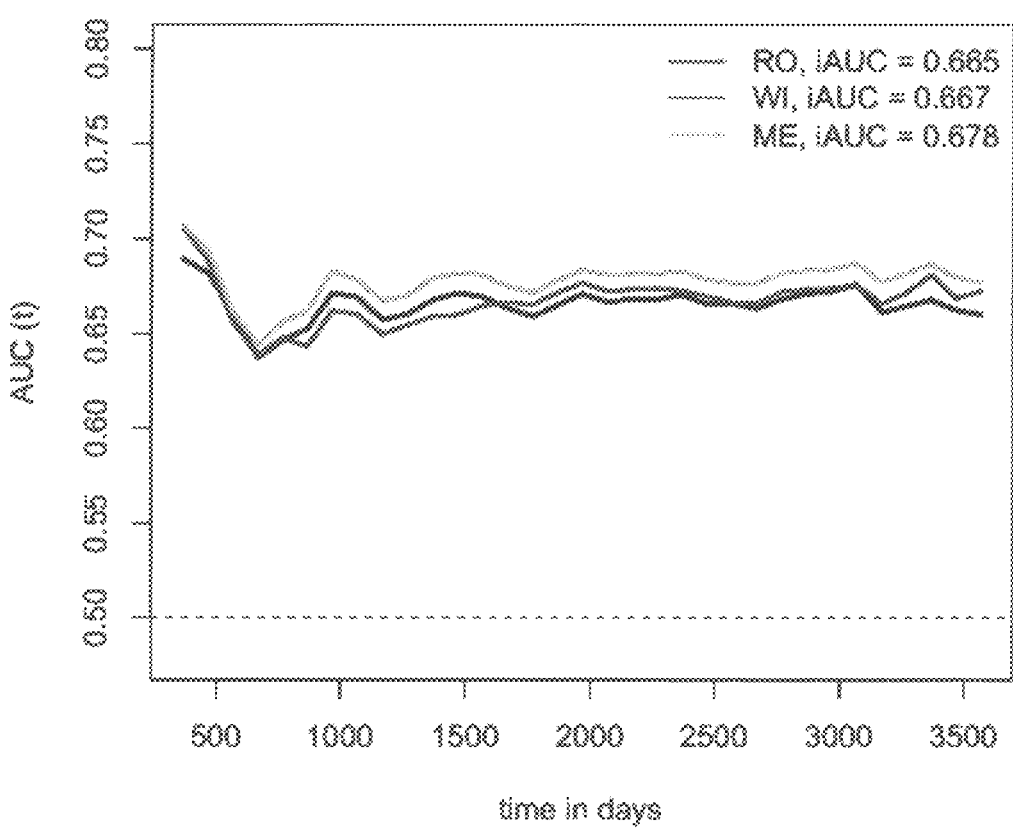
FIG. 17: Evaluation of the time-dependent discrimination accuracy of the genetic risk scores applied to TEDDY data (RO=Oram score, WI=Winkler score, ME=merged score). Discrimination accuracy was calculated between 1 and 10 years of age by increments of 100 days.
Figure 18:
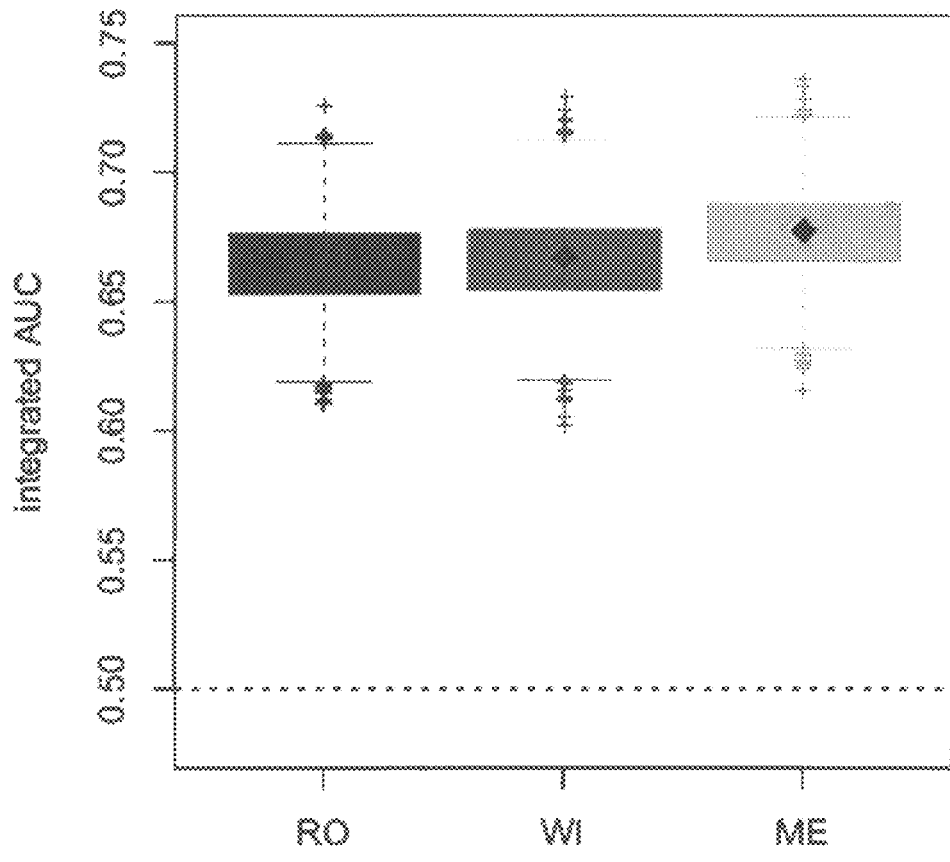
FIG. 18: Boxplots of 2000 paired bootstrap estimates of the integrated discrimination accuracy between 1 and 10 years of age of the three genetic risk scores (RO=Oram score, WI=Winkler score, ME=merged score). Diamonds indicate the integrated AUC on the full TEDDY data.

Since these two already established genetic scores (Winkler and Oram) were not completely overlapping in their SNPs, a score defined by merging the two previously reported genetic scores was also used. The new score brings together the advantages of the Winkler and the Oram score for the stratification of the risk of developing type 1 diabetes in a subject and is significantly better than the Oram and the Winkler score by performing the evaluation of the time-dependent discrimination accuracy (FIGS. 17, 18 and 19).

Besides applying the Winkler and the Oram score, a newly established genetic score called TEDDY or merged score was applied to data from The Environmental Determinants of Diabetes in the Young (TEDDY)[22] and genetic risk score cut-off values indicating the risk (in %) of a subject to develop type 1 diabetes were established. In the TEDDY data, risk stratification using each genetic risk score (Winkler, Oram and merged score) was reproduced. In detail, the abilities of two previously established genetic scores (Winkler and Oram score) and a new genetic score (merged score), which is certainly improved for stratifying the development of type 1 diabetes in children who have been prospectively followed from birth and which were included in the TEDDY cohort were tested. Thereby, applying the merged score using 41 non-HLA class II SNPs as listed in Table 1 to the TEDDY cohort, different genetic risk score cut-off values indicating the risk to develop type 1 diabetes at 6 years of age were provided (FIG. 10). By applying the Winkler score using 38 of the 39 non-HLA class II SNPs or the Oram score using 26 of the 27 non-HLA class II SNPs, different genetic risk score cut-off values indicating the risk to develop type 1 diabetes were also provided (FIGS. 15 and 16).

According to the above-mentioned, the present invention provides a method to precisely predict the risk for developing type 1 diabetes in a subject by using genetic risk scores obtained by the method of the present invention, wherein each of the genetic risk scores (using 41 non-HLA class II SNPs as listed in Table 1) for each subject of the general population including subjects with a first degree family history of type 1 diabetes and without a first degree family history of type 1 diabetes are indicative that said subject is at risk for developing type 1 diabetes and may identify children who, despite not having a first-degree family history of type 1 diabetes, have a risk of developing type 1 diabetes that may be even greater than 10%.

Thus, the present invention provides a method of determining whether a subject is at risk of developing type 1 diabetes by determining the genetic risk score (GRS) of a subject by (a) multiplying the score weight of 41 SNPs, if determined in a sample from said subject with the number of risk alleles for each SNP, if determined, wherein the 41 SNPs and their corresponding score weight are selected from the following ones

TABLE 1

| Overview of the 41 non HLA class II SNPs of the merged score. | |
| --- | --- |
| SNP | score weight per allele |
| rs1264813 | 0.43 |
| rs2395029 | 0.92 |
| rs2476601 | 0.76 |
| rs2816316 | 0.16 |
| rs3024505 | 0.22 |
| rs1990760 | 0.16 |
| rs3087243 | 0.16 |
| rs10517086 | 0.19 |
| rs2069763 | 0.11 |
| rs6897932 | 0.19 |
| rs3757247 | 0.19 |
| rs9388489 | 0.14 |
| rs6920220 | 0.15 |
| rs1738074 | 0.05 |
| rs7804356 | 0.15 |
| rs4948088 | 0.17 |
| rs7020673 | 0.23 |
| rs12722495 | 0.47 |
| rs947474 | 0.15 |
| rs10509540 | 0.25 |
| rs689 or rs1004446 | 0.65 |
| rs4763879 | 0.06 |
| rs2292239 | 0.36 |
| rs3184504 | 0.24 |
| rs1465788 | 0.13 |
| rs17574546 | 0.13 |
| rs3825932 | 0.15 |
| rs12708716 | 0.15 |
| rs4788084 | 0.20 |
| rs7202877 | 0.19 |
| rs2290400 | 0.25 |
| rs7221109 | 0.15 |
| rs45450798 | 0.09 |
| rs763361 | 0.12 |
| rs425105 | 0.21 |
| rs2281808 | 0.07 |
| rs3788013 | 0.16 |
| rs5753037 | 0.15 |
| rs229541 | 0.18 |
| rs5979785 | 0.09 |
| rs2664170 | 0.14 | and wherein a risk allele is determined by assigning the number 0, if the determined SNP is a non-risk allele, and by assigning the number 1, if the determined SNP is present heterozygously, and by assigning the number 2, if the determined SNP is present homozygously, thereby obtaining multiplication products;

(b) assigning the score number 3.15 if SNP rs17426593, SNP rs2187668, and SNP rs7454108 are determined in a subject having a HLA DR4-DQ8/DR4-DQ8 genotype and the score number 3.98 if SNP rs17426593, SNP rs2187668, and SNP rs7454108 are determined in a subject having a HLA DR3/DR4-DQ8 genotype; (c) summing up multiplication products of step a) and the score number of step b), thereby obtaining a genetic risk score; wherein the genetic risk score is indicative that a subject is at risk of developing type 1 diabetes.

The term "type 1 diabetes mellitus (T1D)" refers to an immune-mediated disease in which insulin producing beta-cells (pancreatic islet beta-cells) are completely or near completely destroyed, resulting in life-long dependence on exogenous insulin, in other words resulting in insulin deficiency. It is a chronic and potentially disabling disease that represents a major public health and clinical concern. Symptomatic type 1 diabetes is diagnosed by hyperglycemia often in combination with symptoms of weight loss, thirst, fatigue, and frequent urination, sometimes with ketoacidosis.

The clinical onset of symptomatic T1D is preceded by a pre-symptomatic phase. Pre-symptomatic or stage 1 type 1 diabetes is defined as being normoglycemic but multiple beta cell autoantibody positive. The development of multiple beta cell autoantibodies is defined as being positive for circulating multiple beta cell autoantibodies to beta-cell antigens (GADA, IA-2A, IAA and ZnT8A). First, seroconversion to islet autoantibodies (islet autoantibody positive) occurs in a subject, before said subject may develop multiple islet autoantibodies (multiple islet autoantibody positive). Beta-cell autoimmunity is the pre-symptomatic form of type 1 diabetes and comprises the development of islet autoantibodies and the development of multiple islet autoantibodies.

Further, stage 2 T1D is characterized by having abnormal glucose tolerance and multiple beta cell autoantibodies. Stage 3 is symptomatic T1D with hyperglycemia and clinical signs. Time from stage 1 to stage 3 varies between months and decades.

In this context, the term "type 1 diabetes (T1D)" comprises both the pre-symptomatic and symptomatic phase of type 1 diabetes. In particular, the pre-symptomatic form of T1D namely "beta-cell autoimmunity" may also be preferred in the present invention. Thus, the present invention may also comprise a method of determining whether a subject is at risk of developing pre-symptomatic type 1 diabetes by determining the genetic risk score of a subject.

Neonates and infants who are at increased risk to develop multiple beta-cell autoantibodies (pre-symptomatic T1D) and symptomatic type 1 diabetes can now be identified using genetic markers. This provides opportunity for introducing early therapies to prevent pre-symptomatic and symptomatic type 1 diabetes.

Type 1 diabetes has a multifactorial etiology, which is determined by genetic and environmental factors. Risk in a European population is around 0.4%. A first degree family history of type 1 diabetes is associated with a 5% risk for type 1 diabetes. There are also at least 50 regions of the genome where genetic variation is associated with type 1 diabetes risk. The most important of these is in the HLA DR-DQ region of chromosome 6. Certain HLA DR-DQ genotypes confer markedly elevated risk for type 1 diabetes. Notably, infants who have the HLA DR3/DR4-DQ8 or the DR4-DQ8/DR4-DQ8 genotype have a risk of around 5%. Typing at additional type 1 diabetes susceptibility regions can identify infants with risks that are 10% or more. Thus, family history and genetic markers can be used to identify neonates or infants with 25-fold increased risk for type 1 diabetes.

The term "genetic risk score (GRS)" refers to a score (a number), which is being calculated by the formula as listed in steps (a), (b) and (c) of the method of the present invention and which indicates a certain genetic risk score cut-off value established through the TEDDY cohort. Said risk score cut-off value is indicative that a subject is at risk (in %) of developing type 1 diabetes at a certain age. The genetic risk score of a subject obtained by step (a), (b) and (c) may vary dependent on 1.) whether the nucleotide (e.g. A or G) that is identified at the SNP being analyzed represents a non-risk allele (having no predisposition to develop type 1 diabetes if e.g. the nucleotide A is identified) as one allele type of the SNP, thus assigning the number 0 (subject is homozygous for the non-risk allele) or whether it represents a risk allele (having a predisposition to develop type 1 diabetes if e.g. the nucleotide G is identified) as the other allele type of the SNP, thus assigning the number 1, if the analyzed SNP is present heterozygously or 2, if the analyzed SNP is present homozygously 2.) whether the subject being investigated has the HLA DR3/DR4-DQ8 or the DR4-DQ8/DR4-DQ8 genotype.

In this context, the term "(genetic) risk score cut-off value" refers to a number, which is established by applying either the Winkler (FIG. 15), the Oram (FIG. 16) or the TEDDY score (FIG. 10) to the prospective TEDDY cohort with the HLA DR3/DR4-DQ8 or the DR4-DQ8/DR4-DQ8 genotype and which is indicative that a subject is at risk (in %) of developing type 1 diabetes at a certain age. The cut-off value is indicative that a subject is at risk of developing T1 D by 1 years of age, by 1.5 years of age, by 2 years of age, by 2.5 years of age, by 3 years of age, by 3.5 years of age, by 4 years of age, by 4.5 years of age, by 5 years of age, by 5.5 years of age, by 6 years of age, by 6.5 years of age, by 7 years of age, by 7.5 years of age, by 8 years of age, by 8.5 years of age, by 9 years of age, by 9.5 years of age or by 10 years of age. Preferably, the risk score cut-off value stratifies the risk to develop type 1 diabetes by 6 years of age. Also preferred is a cut-off value stratifying the risk to develop type 1 diabetes by 4 years of age.

The term "a genetic risk score is indicative that a subject is at risk of developing type 1 diabetes" can be used interchangeably with the term "a genetic risk score indicates a certain (genetic) risk score cut-off value, wherein said risk score cut-off value is indicative that a subject is at risk of developing type 1 diabetes". The above mentioned term may also comprise that said genetic risk score is indicative of the rate of progression to develop type 1 diabetes in a subject. The GRS may be indicative of the cumulative risk of developing multiple islet autoantibodies after first appearance of any autoantibodies. Further, it may be indicative of the cumulative risk of developing type 1 diabetes after first appearance of any autoantibodies and additionally be indicative of developing type 1 diabetes after first appearance of multiple autoantibodies. Therefore, a GRS of <13.47 may be indicative for a subject undergoing a slow progression from any to multiple islet autoantibodies or from any autoantibodies to type 1 diabetes or from multiple autoantibodies to type 1 diabetes. A GRS of 13.47-14.88 may be indicative for a subject undergoing average progression from any to multiple islet autoantibodies or from any autoantibodies to type 1 diabetes or from multiple autoantibodies to type 1 diabetes. A GRS>14.88 may be indicative for a subject undergoing average progression from any to multiple islet autoantibodies or from any autoantibodies to type 1 diabetes or from multiple autoantibodies to type 1 diabetes.

After blood or saliva from the subject of the general population is taken on a filter paper, preferably few drops of blood from the heel or venous blood taken from the back of the hand, DNA is extracted and tested for the SNP rs17426593, SNP rs2187668, and SNP rs7454108 which are determined in a subject having a HLA DR4-DQ8/DR4-DQ8 genotype or tested for the SNP rs17426593, SNP rs2187668, and SNP rs7454108 which are determined in a subject having a HLA DR3/DR4-DQ8 genotype. If the HLA DR4-DQ8/DR4-DQ8 or the HLA DR3/DR4-DQ8 genotype is determined in a subject, the subject is classified as having an increased risk (around 5%) to develop type 1 diabetes. Further, the subject is analyzed for the 41 non-HLA class II SNPs as listed in Table 1 that define SNPs from HLA class I and SNPs from the non-HLA type 1 diabetes susceptibility genes, which are also listed in Table 3.

After having analyzed the 41 SNPs, the genetic risk score may be calculated by the formula as listed in step (a), (b) and (c) of the method of the present invention.

As described in step (a) the risk score is calculated by multiplying the number of risk alleles for the 41 SNPs being analyzed (i. e. for each SNP of Table 1 being analyzed for a subject, a risk allele number of 0 is given to a subject, if the determined SNP is a non-risk allele or 1, if the determined SNP is present heterozygously (a subject is heterozygous for the risk allele) or 2, if the determined SNP is present homozygously (a subject is homozygous for the risk allele)) with the score weight assigned for the 41 SNPs, if determined in the sample of the subject having DNA extracted from and being genotyped.

In this context, the term "the determined SNP is a non-risk allele" refers to identifying a nucleotide at the SNP, which defines the allele type of the SNP (risk or no risk), wherein the allele type (in this case a non-risk allele) has no predisposition to develop type 1 diabetes.

The term "the determined SNP is present heterozygously" refers to identifying a nucleotide at the SNP, which defines the allele type of the SNP (risk or no risk), wherein the allele type (in this case a risk allele) has a predisposition to develop type 1 diabetes, thus having a SNP being a risk allele, which a subject is heterozygous for.

The term "the determined SNP is present homozygously" refers to identifying a nucleotide at the SNP, which defines the allele type of the SNP (risk or no risk), wherein the allele type (in this case a risk allele) has a predisposition to develop type 1 diabetes, thus having a SNP being a risk allele, which a subject is homozygous for.

The term "score weight" assigns to the 41 non-HLA class II SNPs listed in Table 1 (comprising HLA class I and non-HLA SNPs) a defined weighted contribution with respect to analyzing 41 SNPs. A SNP (e.g. rs2476601 with a score weight of 0.76) having a higher score weight has greater importance compared to a SNP (e.g. rs4763879 with a score weight of 0.06) having a smaller score weight. By analyzing only e.g. 30 SNPs, different score weights may be assigned to each SNP and thus different genetic score cut-off values for predicting the risk to develop type 1 diabetes may be established through TEDDY data.

The term "SNP" refers to a single-nucleotide polymorphism, being a variation in a single nucleotide that occurs at a specific position in the genome. Depending on the nucleotides and their zygosity found at each SNP being analyzed, the genetic risk score varies. The minimum number of SNPs being tested is 15 SNPs, which are being highlighted in yellow in Table 3 and which are also envisioned by the method of the present invention. The preferred number of SNPs being tested is 41 SNPs listed in Table 1. Also envisioned by the method of the present invention are the analysis of 16, 17, 18, 19, 20, 21, 22, 23, 24, 25, 26, 27, 28, 29, 30, 31, 32, 33, 34, 35, 36, 37, 38, 39, and 40 SNPs of Table 1.

Dependent on how many non-HLA class II SNPs and which SNPs are chosen from Table 1 for the TEDDY score being applied to the TEDDY cohort, different risk score cut-off values indicating the risk of a subject of developing type 1 diabetes may be established (FIG. 10 and FIG. 12).

Thus, if the genetic risk score of a newborn or an infant is calculated by analyzing e.g. 30 SNPs, the risk of developing type 1 diabetes may be stratified from different risk score cut-off values being established by applying the same number of SNPs (e.g. 30 SNPs) to the TEDDY cohort beforehand in comparison to a newborn or an infant, whose genetic risk score is calculated by analyzing 41 SNPs and whose risk to develop type 1 diabetes is stratified from the risk score cut-off values depicted in FIG. 10 being established by applying the merged score using 41 SNPs to the TEDDY cohort. For analyzing only 38, 39 or 40 SNPs, the score weights depicted in Table 1 may also be used as for analyzing all 41 SNPs being preferred and thus the same risk score cut-off values may be used to predict the risk to develop type 1 diabetes as can be seen from FIG. 10. Thus, by using 41 SNPs listed in Table 1 in the present invention, an equivalent use of any of 38, 39, or 40 SNPs of Table 1 may also be comprised by said term herein. However, the present invention works at its best by applying all 41 SNPs listed in Table 1. If one SNP is missing/not being available in a subject, its score and the genotype distribution may be examined to provide what would be the likely score based on the population. If e.g. SNPxx had a score for a risk allele (A) of 0.5, and the population distribution of genotypes was AA 10%, AT 45%, TT 55%, then the score given to a missing value would be:

$$(0.1 \times (2 \times 0.5)) + (0.45 \times (1 \times 0.5)) + (0.55 \times (0 \times 0.5)) = 0.55.$$

However, the invention may also be applied using the 41 SNPs listed in Table 1 and any additional SNPs, thus having the 41 SNPs of Table 1 plus one, two, three, four, five or more additional SNPs.

Figures 22A, 22B:
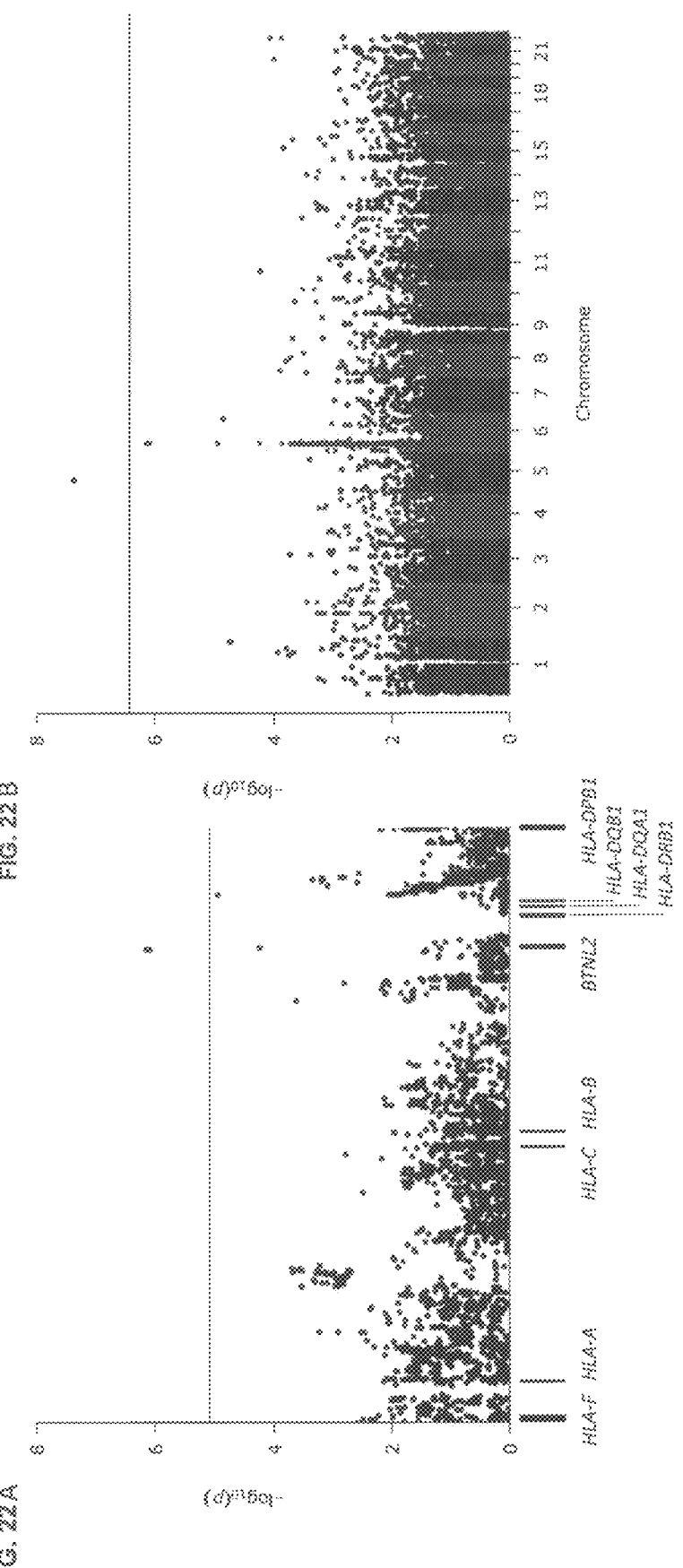
FIGS. 22A-22B: Manhattan plot for enrichment of alleles in children with first degree family history (FDR children). Analysis was made for SNPs in the HLA region on chromosome 6 (FIG. 20A) and the whole Immunochip data (FIG. 20B). The thresholds for p-values after correction $(8.2 \times 10^{-6}$ and $4.5 \times 10^{-7};)$ are indicated by the sold lines.

The inventors have found that two additional SNPs, not yet being listed and examined for calculating the GRS of the present invention, are significantly enriched in a subject having a first degree family history. These two SNPs refer to rs3763305 and rs3817964 being intron variants of BTNL2 (FIG. 22A). Both SNPs are close to HLA DRB1.

Further, another SNP called rs7735139 on chromosome 5 has also been identified with allelic enrichment in a subject having a first degree family history (FIG. 22B). These new SNPs are additional susceptibility genes that are in linkage disequlibrium with HLA DR. These additional SNPs may be increased in frequency in a subject having a first degree family history and account for some of the excess risk in these children. The present invention may therefore be applied by using all 41 SNPs listed in Table 1 and the additional SNPs rs3763305, rs3817964 and/or rs7735139, preferably by using all 41 SNPs listed in Table 1 and the additional BTNL2 SNP rs3763305.

The oligo- or polynucleotides, or complementary strands thereof, defined by the SEQ ID NOs contain one type 1 diabetes susceptibility SNP marker that is a single nucleotide polymorphism (SNP) which is present in a haplotype block represented by a sequence set forth in any one of SEQ ID NO. 1-42. When a certain nucleotide at the type 1 diabetes susceptibility SNP marker of these oligo- or polynucleotides, or complementary strands thereof, is detected, the genetic predisposition of developing type 1 diabetes in a subject can be examined and/or determined since the identified nucleotide represents the allele type of the SNP (non-risk allele or risk allele). Therefore, the nucleotide at the SNP of these oligo- or polynucleotides, or complementary strands thereof identifying the allele type of the SNP can be defined and used as a marker for determining the genetic predisposition of developing type 1 diabetes in a subject. The nucleotide at the analyzed SNP may be identified by sequencing or through PCR, or any other method that is known to the person skilled in the art.

The length (nucleotide length) of these oligo- or polynucleotides, or complementary strands, is desirably a length which is specifically recognized in human genome. The length is usually equal to or more than 10-mers and equal to or fewer than 1000-mers, preferably equal to or more than 20-mers and equal to or fewer than 500-mers, and more preferably equal to or more than 20-mers and equal to or fewer than 100-mers, and most preferably equal to or more than 40-mers and equal to or fewer than 100-mers. Therefore, if necessary, the length can be set to, for example, 11 nucleotides containing a type I diabetes susceptibility SNP marker, preferably including 5 nucleotides each on the 5' side and the 3' side of the type I diabetes susceptibility SNP marker; or 21 nucleotides preferably including 10 nucleotides each on the 5' side and the 3' side of the type I diabetes susceptibility SNP marker; or 41 nucleotides preferably including 20 nucleotides each on the 5' side and the 3' side of the type I diabetes susceptibility SNP marker; or 61 nucleotides preferably including 30 nucleotides each on the 5' side and the 3' side of the type I diabetes susceptibility SNP marker; or 81 nucleotides preferably including 40 nucleotides each on the 5' side and the 3' side of the type I diabetes susceptibility SNP marker, or 101 nucleotides preferably including 50 nucleotides each on the 5' side and the 3' side of the type I diabetes susceptibility SNP marker. Preferably, a length of 81 nucleotides including 40 nucleotides each on the 5' side and the 3' side of the type I diabetes susceptibility SNP marker.

The type I diabetes susceptibility SNP markers of Table 1 used in the present invention, are characterized by the following:

(1) nucleotide represented by Nucleotide Number 41 (dbSNP Database ID: rs1264813, A or G) in the sequence set forth in SEQ ID NO 1, (2) nucleotide represented by Nucleotide Number 41 (dbSNP Database ID: rs2395029, G or T) in the sequence set forth in SEQ ID NO 2, (3) nucleotide represented by Nucleotide Number 41 (dbSNP Database ID: rs2476601, A or G) in the sequence set forth in SEQ ID NO 3, (4) nucleotide represented by Nucleotide Number 41 (dbSNP Database ID: rs2816316, G or T) in the sequence set forth in SEQ ID NO 4, (5) nucleotide represented by Nucleotide Number 41 (dbSNP Database ID: rs3024505, C or T) in the sequence set forth in SEQ ID NO 5, (6) nucleotide represented by Nucleotide Number 41 (dbSNP Database ID: rs1990760, C or T) in the sequence set forth in SEQ ID NO 6, (7) nucleotide represented by Nucleotide Number 41 (dbSNP Database ID: rs3087243, A or G) in the sequence set forth in SEQ ID NO 7, (8) nucleotide represented by Nucleotide Number 41 (dbSNP Database ID: rs10517086, A or G) in the sequence set forth in SEQ ID NO 8, (9) nucleotide represented by Nucleotide Number 41 (dbSNP Database ID: rs2069763, G or T) in the sequence set forth in SEQ ID NO 9,

(10) nucleotide represented by Nucleotide Number 41 (dbSNP Database ID: rs6897932, C or T) in the sequence set forth in SEQ ID NO 10,

(11) nucleotide represented by Nucleotide Number 41 (dbSNP Database ID: rs3757247, A or G) in the sequence set forth in SEQ ID NO 11,

(12) nucleotide represented by Nucleotide Number 41 (dbSNP Database ID: rs9388489, A or G) in the sequence set forth in SEQ ID NO 12,

(13) nucleotide represented by Nucleotide Number 41 (dbSNP Database ID: rs6920220, A or G) in the sequence set forth in SEQ ID NO 13,

(14) nucleotide represented by Nucleotide Number 41 (dbSNP Database ID: rs1738074, A or G) in the sequence set forth in SEQ ID NO 14,

(15) nucleotide represented by Nucleotide Number 41 (dbSNP Database ID: rs7804356, C or T) in the sequence set forth in SEQ ID NO 15,

(16) nucleotide represented by Nucleotide Number 41 (dbSNP Database ID: rs4948088, A or C) in the sequence set forth in SEQ ID NO 16,

(17) nucleotide represented by Nucleotide Number 41 (dbSNP Database ID: rs7020673, C or G) in the sequence set forth in SEQ ID NO 17,

(18) nucleotide represented by Nucleotide Number 41 (dbSNP Database ID: rs12722495, A or G) in the sequence set forth in SEQ ID NO 18,

(19) nucleotide represented by Nucleotide Number 41 (dbSNP Database ID: rs947474, A or G) in the sequence set forth in SEQ ID NO 19,

(20) nucleotide represented by Nucleotide Number 41 (dbSNP Database ID: rs10509540, C or T) in the sequence set forth in SEQ ID NO 20,

(21) nucleotide represented by Nucleotide Number 41 (dbSNP Database ID: rs689, A or T) in the sequence set forth in SEQ ID NO 21,

(22) nucleotide represented by Nucleotide Number 41 (dbSNP Database ID: rs4763879, A or G) in the sequence set forth in SEQ ID NO 22,

(23) nucleotide represented by Nucleotide Number 41 (dbSNP Database ID: rs2292239, A or C) in the sequence set forth in SEQ ID NO 23,

(24) nucleotide represented by Nucleotide Number 41 (dbSNP Database ID: rs3184504, C or T) in the sequence set forth in SEQ ID NO 24,

(25) nucleotide represented by Nucleotide Number 41 (dbSNP Database ID: rs1465788, A or G) in the sequence set forth in SEQ ID NO 25,

(26) nucleotide represented by Nucleotide Number 41 (dbSNP Database ID: rs17574546, A or C) in the sequence set forth in SEQ ID NO 26,

(27) nucleotide represented by Nucleotide Number 41 (dbSNP Database ID: rs3825932, C or T) in the sequence set forth in SEQ ID NO 27,

(28) nucleotide represented by Nucleotide Number 41 (dbSNP Database ID: rs12708716, A or G) in the sequence set forth in SEQ ID NO 28,

(29) nucleotide represented by Nucleotide Number 41 (dbSNP Database ID: rs4788084, A or G) in the sequence set forth in SEQ ID NO 29,

(30) nucleotide represented by Nucleotide Number 41 (dbSNP Database ID: rs7202877, C or G or T) in the sequence set forth in SEQ ID NO 30,

(31) nucleotide represented by Nucleotide Number 41 (dbSNP Database ID: rs2290400, A or G) in the sequence set forth in SEQ ID NO 31,

(32) nucleotide represented by Nucleotide Number 41 (dbSNP Database ID: rs7221109, C or T) in the sequence set forth in SEQ ID NO 32,

(33) nucleotide represented by Nucleotide Number 41 (dbSNP Database ID: rs45450798, C or G) in the sequence set forth in SEQ ID NO 33,

(34) nucleotide represented by Nucleotide Number 41 (dbSNP Database ID: rs763361, A or C or T) in the sequence set forth in SEQ ID NO 34,

(35) nucleotide represented by Nucleotide Number 41 (dbSNP Database ID: rs425105, A or G) in the sequence set forth in SEQ ID NO 35,

(36) nucleotide represented by Nucleotide Number 41 (dbSNP Database ID: rs2281808, C or T) in the sequence set forth in SEQ ID NO 36,

(37) nucleotide represented by Nucleotide Number 41 (dbSNP Database ID: rs3788013, A or C) in the sequence set forth in SEQ ID NO 37,

(38) nucleotide represented by Nucleotide Number 41 (dbSNP Database ID: rs5753037, C or T) in the sequence set forth in SEQ ID NO 38,

(39) nucleotide represented by Nucleotide Number 41 (dbSNP Database ID: rs229541, C or T) in the sequence set forth in SEQ ID NO 39,

(40) nucleotide represented by Nucleotide Number 41 (dbSNP Database ID: rs5979785, C or T) in the sequence set forth in SEQ ID NO 40,

(41) nucleotide represented by Nucleotide Number 41 (dbSNP Database ID: rs2664170, A or G) in the sequence set forth in SEQ ID NO 41,

(42) nucleotide represented by Nucleotide Number 41 (dbSNP Database ID: rs1004446, C or T; often used instead of rs689) in the sequence set forth in SEQ ID NO 42.

Further, in the sequence set forth in SEQ ID NO 1, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes ("non risk allele"). Since SEQ ID NO. 1 is located on the reverse strand, the nucleotide represented by Nucleotide Number 41 may be T or C, and it is determined, when the nucleotide is T ("risk allele"), that the subject has a predisposition to develop type 1 diabetes, or when the nucleotide is C, the subject does not have a predisposition to develop type 1 diabetes ("non risk allele").

Further, in the sequence set forth in SEQ ID NO 2, it is identified whether the nucleotide represented by Nucleotide Number 41 is G or T, and it is determined, when the nucleotide is T ("risk allele"), that the subject has a predisposition to develop type 1 diabetes, or when the nucleotide is G, the subject does not have a predisposition to develop type 1 diabetes.

Further, in the sequence set forth in SEQ ID NO 3, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes.

Further, in the sequence set forth in SEQ ID NO 4, it is identified whether the nucleotide represented by Nucleotide Number 41 is G or T, and it is determined, when the nucleotide is T ("risk allele"), that the subject has a predisposition to develop type 1 diabetes, or when the nucleotide is G, the subject does not have a predisposition to develop type 1 diabetes. Since SEQ ID NO. 4 is located on the reverse strand, the nucleotide represented by Nucleotide Number 41 may be C or A, and it is determined, when the nucleotide is A ("risk allele"), that the subject has a predisposition to develop type 1 diabetes, or when the nucleotide is C, the subject does not have a predisposition to develop type 1 diabetes.

Further, in the sequence set forth in SEQ ID NO 5, it is identified whether the nucleotide represented by Nucleotide Number 41 is C or T, and it is determined, when the nucleotide is C ("risk allele"), that the subject has a predisposition to develop type 1 diabetes, or when the nucleotide is T, the subject does not have a predisposition to develop type 1 diabetes. Since SEQ ID NO. 5 is located on the reverse strand, the nucleotide represented by Nucleotide Number 41 may be G or A, and it is determined, when the nucleotide is G ("risk allele"), that the subject has a predisposition to develop type 1 diabetes, or when the nucleotide is A, the subject does not have a predisposition to develop type 1 diabetes.

Further, in the sequence set forth in SEQ ID NO 6, it is identified whether the nucleotide represented by Nucleotide Number 41 is C or T, and it is determined, when the nucleotide is A ("risk allele"), that the subject has a predisposition to develop type 1 diabetes, or when the nucleotide is C or T, the subject does not have a predisposition to develop type 1 diabetes.

Further, in the sequence set forth in SEQ ID NO 7, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes.

Further, in the sequence set forth in SEQ ID NO 8, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes.

Further, in the sequence set forth in SEQ ID NO 9, it is identified whether the nucleotide represented by Nucleotide Number 41 is G or T, and it is determined, when the nucleotide is A ("risk allele"), that the subject has a predisposition to develop type 1 diabetes, or when the nucleotide is G or T, the subject does not have a predisposition to develop type 1 diabetes. Since SEQ ID NO. 9 is located on the reverse strand, the nucleotide represented by Nucleotide Number 41 may be C or A, and it is determined, when the nucleotide is T ("risk allele"), that the subject has a predisposition to develop type 1 diabetes, or when the nucleotide is C or A, the subject does not have a predisposition to develop type 1 diabetes.

Further, in the sequence set forth in SEQ ID NO 10, it is identified whether the nucleotide represented by Nucleotide Number 41 is C or T, and it is determined, when the nucleotide is G ("risk allele"), that the subject has a predisposition to develop type 1 diabetes, or when the nucleotide is C or T, the subject does not have a predisposition to develop type 1 diabetes.

Further, in the sequence set forth in SEQ ID NO 11, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes. Since SEQ ID NO. 11 is located on the reverse strand, the nucleotide represented by Nucleotide Number 41 may be T or C, and it is determined, when the nucleotide is T ("risk allele"), that the subject has a predisposition to develop type 1 diabetes, or when the nucleotide is C, the subject does not have a predisposition to develop type 1 diabetes.

Further, in the sequence set forth in SEQ ID NO 12, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes.

Further, in the sequence set forth in SEQ ID NO 13, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes.

Further, in the sequence set forth in SEQ ID NO 14, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes. Since SEQ ID NO. 14 is located on the reverse strand, the nucleotide represented by Nucleotide Number 41 may be T or C, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 15, it is identified whether the nucleotide represented by Nucleotide Number 41 is C or T, and it is determined, when the nucleotide is A ("risk allele"), that the subject has a predisposition to develop type 1 diabetes, or when the nucleotide is C or T, the subject does not have a predisposition to develop type 1 diabetes.

Further, in the sequence set forth in SEQ ID NO 16, it is identified whether the nucleotide represented by Nucleotide Number 41 is A or C, and it is determined, when the nucleotide is C ("risk allele"), that the subject has a predisposition to develop type 1 diabetes, or when the nucleotide is A, the subject does not have a predisposition to develop type 1 diabetes.

Further, in the sequence set forth in SEQ ID NO 17, it is identified whether the nucleotide represented by Nucleotide Number 41 is C or G, and it is determined, when the nucleotide is G ("risk allele"), that the subject has a predisposition to develop type 1 diabetes, or when the nucleotide is C, the subject does not have a predisposition to develop type 1 diabetes.

Further, in the sequence set forth in SEQ ID NO 18, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes. Since SEQ ID NO. 18 is located on the reverse strand, the nucleotide represented by Nucleotide Number 41 may be T or C, and it is determined, when the nucleotide is T ("risk allele"), that the subject has a predisposition to develop type 1 diabetes, or when the nucleotide is C, the subject does not have a predisposition to develop type 1 diabetes.

Further, in the sequence set forth in SEQ ID NO 19, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes.

Further, in the sequence set forth in SEQ ID NO 20, it is identified whether the nucleotide represented by Nucleotide Number 41 is C or T, and it is determined, when the nucleotide is T ("risk allele"), that the subject has a predisposition to develop type 1 diabetes, or when the nucleotide is C, the subject does not have a predisposition to develop type 1 diabetes.

Further, in the sequence set forth in SEQ ID NO 21, it is identified whether the nucleotide represented by Nucleotide Number 41 is A or T, and it is determined, when the nucleotide is T ("risk allele"), that the subject has a predisposition to develop type 1 diabetes, or when the nucleotide is A, the subject does not have a predisposition to develop type 1 diabetes. Since SEQ ID NO. 21 is located on the reverse strand, the nucleotide represented by Nucleotide Number 41 may be T or A, and it is determined, when the nucleotide is A ("risk allele"), that the subject has a predisposition to develop type 1 diabetes, or when the nucleotide is T, the subject does not have a predisposition to develop type 1 diabetes.

Further, in the sequence set forth in SEQ ID NO 22, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes.

Further, in the sequence set forth in SEQ ID NO 23, it is identified whether the nucleotide represented by Nucleotide Number 41 is A or C, and it is determined, when the nucleotide is A ("risk allele"), that the subject has a predisposition to develop type 1 diabetes, or when the nucleotide is C, the subject does not have a predisposition to develop type 1 diabetes. Since SEQ ID NO. 23 is located on the reverse strand, the nucleotide represented by Nucleotide Number 41 may be T or G, and it is determined, when the nucleotide is T ("risk allele"), that the subject has a predisposition to develop type 1 diabetes, or when the nucleotide is G, the subject does not have a predisposition to develop type 1 diabetes.

Further, in the sequence set forth in SEQ ID NO 24, it is identified whether the nucleotide represented by Nucleotide Number 41 is C or T, and it is determined, when the nucleotide is T ("risk allele"), that the subject has a predisposition to develop type 1 diabetes, or when the nucleotide is C, the subject does not have a predisposition to develop type 1 diabetes.

Further, in the sequence set forth in SEQ ID NO 25, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes. Since SEQ ID NO. 25 is located on the reverse strand, the nucleotide represented by Nucleotide Number 41 may be T or C, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 26, it is identified whether the nucleotide represented by Nucleotide Number 41 is A or C, and it is determined, when the nucleotide is C ("risk allele"), that the subject has a predisposition to develop type 1 diabetes, or when the nucleotide is A, the subject does not have a predisposition to develop type 1 diabetes.

Further, in the sequence set forth in SEQ ID NO 27, it is identified whether the nucleotide represented by Nucleotide Number 41 is C or T, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 28, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes.

Further, in the sequence set forth in SEQ ID NO 29, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes. Since SEQ ID NO. 29 is located on the reverse strand, the nucleotide represented by Nucleotide Number 41 may be T or C, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 30, it is identified whether the nucleotide represented by Nucleotide Number 41 is C or G or T, and it is determined, when the nucleotide is C ("risk allele"), that the subject has a predisposition to develop type 1 diabetes, or when the nucleotide is G or T, the subject does not have a predisposition to develop type 1 diabetes.

Further, in the sequence set forth in SEQ ID NO 31, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes. Since SEQ ID NO. 31 is located on the reverse strand, the nucleotide represented by Nucleotide Number 41 may be T or C, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 32, it is identified whether the nucleotide represented by Nucleotide Number 41 is C or T, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 33, it is identified whether the nucleotide represented by Nucleotide Number 41 is C or G, and it is determined, when the nucleotide is C ("risk allele"), that the subject has a predisposition to develop type 1 diabetes, or when the nucleotide is G, the subject does not have a predisposition to develop type 1 diabetes. Since SEQ ID NO. 33 is located on the reverse strand, the nucleotide represented by Nucleotide Number 41 may be G or C, and it is determined, when the nucleotide is G ("risk allele"), that the subject has a predisposition to develop type 1 diabetes, or when the nucleotide is C, the subject does not have a predisposition to develop type 1 diabetes.

Further, in the sequence set forth in SEQ ID NO 34, it is identified whether the nucleotide represented by Nucleotide Number 41 is A or C or T, and it is determined, when the nucleotide is A ("risk allele"), that the subject has a predisposition to develop type 1 diabetes, or when the nucleotide is C or T, the subject does not have a predisposition to develop type 1 diabetes.

Further, in the sequence set forth in SEQ ID NO 35, it is identified whether the nucleotide represented by Nucleotide Number 41 is A or G, and it is determined, when the nucleotide is A ("risk allele"), that the subject has a predisposition to develop type 1 diabetes, or when the nucleotide is G, the subject does not have a predisposition to develop type 1 diabetes. Since SEQ ID NO. 35 is located on the reverse strand, the nucleotide represented by Nucleotide Number 41 may be T or C, and it is determined, when the nucleotide is T ("risk allele"), that the subject has a predisposition to develop type 1 diabetes, or when the nucleotide is C, the subject does not have a predisposition to develop type 1 diabetes.

Further, in the sequence set forth in SEQ ID NO 36, it is identified whether the nucleotide represented by Nucleotide Number 41 is C or T, and it is determined, when the nucleotide is C ("risk allele"), that the subject has a predisposition to develop type 1 diabetes, or when the nucleotide is T, the subject does not have a predisposition to develop type 1 diabetes.

Further, in the sequence set forth in SEQ ID NO 37, it is identified whether the nucleotide represented by Nucleotide Number 41 is A or C, and it is determined, when the nucleotide is A ("risk allele"), that the subject has a predisposition to develop type 1 diabetes, or when the nucleotide is C, the subject does not have a predisposition to develop type 1 diabetes.

Further, in the sequence set forth in SEQ ID NO 38, it is identified whether the nucleotide represented by Nucleotide Number 41 is C or T, and it is determined, when the nucleotide is A ("risk allele"), that the subject has a predisposition to develop type 1 diabetes, or when the nucleotide is C or T, the subject does not have a predisposition to develop type 1 diabetes.

Further, in the sequence set forth in SEQ ID NO 39, it is identified whether the nucleotide represented by Nucleotide Number 41 is C or T, and it is determined, when the nucleotide is A ("risk allele"), that the subject has a predisposition to develop type 1 diabetes, or when the nucleotide is C or T, the subject does not have a predisposition to develop type 1 diabetes. Since SEQ ID NO. 39 is located on the reverse strand, the nucleotide represented by Nucleotide Number 41 may be G or A, and it is determined, when the nucleotide is T ("risk allele"), that the subject has a predisposition to develop type 1 diabetes, or when the nucleotide is G or A, the subject does not have a predisposition to develop type 1 diabetes.

Further, in the sequence set forth in SEQ ID NO 40, it is identified whether the nucleotide represented by Nucleotide Number 41 is C or T, and it is determined, when the nucleotide is T ("risk allele"), that the subject has a predisposition to develop type 1 diabetes, or when the nucleotide is C, the subject does not have a predisposition to develop type 1 diabetes.

Further, in the sequence set forth in SEQ ID NO 41, it is identified whether the nucleotide represented by Nucleotide Number 41 is A or G, and it is determined, when the nucleotide is G ("risk allele"), that the subject has a predisposition to develop type 1 diabetes, or when the nucleotide is A, the subject does not have a predisposition to develop type 1 diabetes.

Further, in the sequence set forth in SEQ ID NO 42, it is identified whether the nucleotide represented by Nucleotide Number 41 is C or T, and it is determined, when the nucleotide is T ("risk allele"), that the subject has a predisposition to develop type 1 diabetes, or when the nucleotide is C, the subject does not have a predisposition to develop type 1 diabetes. Since SEQ ID NO. 42 is located on the reverse strand, the nucleotide represented by Nucleotide Number 41 may be G or A, and it is determined, when the nucleotide is A ("risk allele"), that the subject has a predisposition to develop type 1 diabetes, or when the nucleotide is G, the subject does not have a predisposition to develop type 1 diabetes.

In this context, the term "risk allele" refers to a nucleotide at a certain position (at position 11, 21, 31, 41, 51, 61, 71, 81, 91 or 101 of a sequence used as a marker for determining the genetic predisposition of developing type 1 diabetes in a subject), preferably at position 41 of any one of SEQ ID NO. 1-42, which indicates a predisposition to develop type 1 diabetes.

In this context, the term "Nucleotide Number" refers to two nucleotides at a certain position (at position 11, 21, 31, 41, 51, 61, 71, 81, 91 or 101 of a sequence used as a marker for determining the genetic predisposition of developing type 1 diabetes in a subject), preferably at position 41 of any one of SEQ ID NO. 1-42, one indicating that a subject has a predisposition to type 1 diabetes, the other indicating that a subject does not have a predisposition to type 1 diabetes. If the listed risk allele (e.g. A) is conform with the Nucleotide Number listed (e.g. A or G), the Nucleotide Number (e.g. A) is indicative that a subject has a predisposition to type 1 diabetes and the other Nucleotide Number (e.g G) is indicative that a subject does not have a predisposition to type 1 diabetes. If the listed risk allele (e.g. A) is not conform with the Nucleotide Number listed (e.g. C or T), the Nucleotide Number (e.g. C or T) is indicative that a subject does not have a predisposition to type 1 diabetes.

In the following Table 2 the oligo- or polynucleotides, or complementary strands thereof, defined by the SEQ ID NOs containing one type 1 diabetes susceptibility SNP marker are characterized in detail.

TABLE 2

Overview of all 42 SEQ ID NOs. containing one type 1 diabetes
susceptibility SNP marker (depicted as rs-number).

| SEQ ID No. | SNP | FWD (+) | REV (-) | Risk allele | REV. Annot. of risk allele | Fre-quency of risk allele | Sequence |
|---|---|---|---|---|---|---|---|
| 1 | rs1264813 | 0 | 1 | A | T | major | AGAGCTGGGGGCAGAGAGCAGGGACCTGTCTGTCCCCACT R = A or G<br>GATCTGGCTGGGGCAGGGGTGAGGAATAGGGGTCAGCAG |
| 2 | rs2395029 | 1 | 0 | T | T | major | CACCCGCTGGTCTCTGGACACATACTGTCCAATTCCCCTG K = G or T<br>GGCAGCTGTAATGTGTAGTTCAATGGGCACTCATTTGTCC |
| 3 | rs2476601 | 1 | 0 | A | A | minor | TCACCAGCTTCCTCAACCACAATAAATGATTCAGGTGTCC R = A or G<br>TACAGGAAGTGGAGGGGGGATTTCATCATCTATCCTTGGA |
| 4 | rs2816316 | 0 | 1 | T | A | major | GCAGATCTTATCCAGCTCCCTCCTGTTGTGGAGGAATATT K = G or T<br>AGTTGTCTGTTGTTTTAGATAGGATTTCCATAGCTGCAAG |
| 5 | rs3024505 | 0 | 1 | C | G | major | GGAGAGAGGAGGAAAAAAATGAGCTGAGTAAACACTAGTC Y = C or T<br>CCCTCACGCTCTGCCTGGGCAGCCCTGGTCTGGGGAAGGC |
| 6 | rs1990760 | 1 | 0 | A | A | major | TCACCATTTATTTGATAGTCGGCACACTTCTTTTGCAGTG Y = C or T<br>TTTGTTTTCTCTTACAATGTAAAGTTCCCTATAAGTATCA |
| 7 | rs3087243 | 1 | 0 | G | G | major | TCTTTCCTTTTGATTTCTTCACCACTATTTGGGATATAAC R = A or G<br>TGGGTTAACACAGACATAGCAGTCCTTTATAAATCAATTG |
| 8 | rs10517086 | 1 | 0 | A | A | minor | TTTGCATATATATATATTTTTTACAAAAAGGATGGTCTTG R = A or G<br>AAGGTTGTCATAAACTCAGGGACACAGGAGTTCCGTCTCA |
| 9 | rs2069763 | 0 | 1 | A | T | minor | GTTCTACAAAGAAAACACAGCTACAACTGGAGCATTTACT K = G or T<br>CTGGATTTACAGATGATTTTGAATGGAATTAATGTAAGTA |
| 10 | rs6897932 | 1 | 0 | G | G | major | TATTCTTGCTTTCCAGGGGAGATGGATCCTATCTTACTAA Y = C or T<br>CATCAGCATTTTGAGTTTTTTCTCTGTCGCTCTGTTGGTC |
| 11 | rs3757247 | 0 | 1 | A | T | minor | AGGCATGGGAACCACTTGGGTAAAGGCATGGAGATGGGAA R = A or G<br>ACATTCCAGGGATAGCTATTAACCCTTTTTAACTGAAGCA |
| 12 | rs9388489 | 1 | 0 | G | G | minor | TAAACTCAGATTGCAGAAGGTGATAGTTAAATGCCTTGTT R = A or G<br>GATTTTTTAGCCAGTGTGAGTCTGTTGTACCACAAAATTG |
| 13 | rs6920220 | 1 | 0 | A | A | minor | ATCTGCTTCCATCTGTTAGCAGGTAACTTCTCCACTAAAA R = A or G<br>GATATGGTTCTGTAGAACAATGGCATATGCAGACAGTGAT |
| 14 | rs1738074 | 0 | 1 | G | C | major | GTCTCTCTCTCTCCCAGTGGACTAGAAGGAGCAGAGAGTT R = A or G<br>TGCTGTTTCTCCCATTCTTTACAGCTCACCGGATGTAAAA |
| 15 | rs7804356 | 1 | 0 | A | A | major | TAAAATAAGGGTGTAAAGGTAGAAAGGAGGAAAAAGGTTA Y = C or T<br>GTTCACAATGTGACCCTACATTGACTAGAGAGAGAGACAA |

TABLE 2-continued

Overview of all 42 SEQ ID NOs. containing one type 1 diabetes
susceptibility SNP marker (depicted as rs-number).

| SEQ ID No. | SNP | FWD (+) | REV (−) | Risk allele | REV. Annot. of risk allele | Frequency of risk allele | Sequence | |
|---|---|---|---|---|---|---|---|---|
| 16 | rs4948088 | 1 | 0 | C | C | major | AAGTGGGTGCCACAACAAGACATGAGCTAGTCTTGGGATA<br>CCACCTCTGCTGCCAGGCCAAAAAGAAACCTCTGATCCCG | M = A or C |
| 17 | rs7020673 | 1 | 0 | G | G | major | GAGCCTTCCACACAGTGATAATGGCTACAGATTGCTGGAG<br>AAATTCAGGACCTTCAGGAATACACCGCTCGAGGGCAATA | S = C or G |
| 18 | rs12722495 | 0 | 1 | A | T | major | ATCACAATACCTTCCCTTCCAGTTCCTTGAATACTTCCAA<br>TCGCACTTAGGATTGAAACTCACCAAATTAGAGAGATGGA | R = A or G |
| 19 | rs947474 | 1 | 0 | A | A | major | AAAACACTCACAGGACAATTTTCCTAACCCTTGGTCTCTC<br>GAATGCTATTTTTTAGGCTAATTTGTTTTGATGAGAAAAC | R = A or G |
| 20 | rs10509540 | 1 | 0 | T | T | major | ATTTGAGCAGGTAGGATGTGATTCTGACTCAGAGAAATTA<br>ATGGTGTCTGGAAAGGGGGCATGTGGGATCTCTGAGTGTC | Y = C or T |
| 21 | rs689*(or) | 0 | 1 | T | A | major | CAGGGCACCTGGCCTTCAGCCTGCCTCAGCCCTGCCTGTC<br>CCCAGATCACTGTCCTTCTGCCATGGCCCTGTGGATGCGC | W = A or T |
| 22 | rs4763879 | 1 | 0 | A | A | minor | TAAGTGAACAAATTATGGTATATCCATACAAGGGAATTCC<br>CTCAGCAATTCAAAATAAGACAACTGATACATGCAACAAA | R = A or G |
| 23 | rs2292239 | 0 | 1 | A | T | minor | TGTCCCCATCTGCCACCCTAGATCCCTTAAGTGCTGCCCT<br>TAGATTCAAAAGTCTCTTCACTATTTGTTGCTACAAGGAG | M = A or C |
| 24 | rs3184504 | 1 | 0 | T | T | minor | CAAGCTACAAGCAGCTTGCTCCAGCATCCAGGAGGTCCGG<br>GGTGCACACGGCTTGAGATGCCTGACAACCTTTACACCTT | Y = C or T |
| 25 | rs1465788 | 0 | 1 | G | C | major | AGTTGTCAGTTGACCATTTAATGGAAGTCTACACTGAATA<br>TCCTTTGCCAAGTGAATAGCCCCGGAATTTGTTTTGTGGT | R = A or G |
| 26 | rs17574546 | 1 | 0 | C | C | minor | AATTCGTACTCCCACCATGTTGTTTCCTTCTTTCATCCTC<br>GGTATGGTAATCTAGAATCAATAATTTGTTTTGTTTTCAC | M = A or C |
| 27 | rs3825932 | 1 | 0 | C | C | minor | CAGGGTTTGAGTTTAGGACAATTGACTACCAGTTTGCCTC<br>GGAGAGATTATTCTGGGGCCAGAATAATCTGCTGGTGAAC | Y = C or T |
| 28 | rs12708716 | 1 | 0 | A | A | major | CGGGTCTTCAGCTAGTCCTCTGGGCAGTAGGGAGAATCCT<br>AGTAATAGCCGCTTCACAGGGAGTCAGTGAGGATGAAGTG | R = A or G |
| 29 | rs4788084 | 0 | 1 | G | C | major | CCTGATTTCTAGGGAGTTCTGTGGCCTTCAGGGAGTCCCA<br>GGGAGCAAGATTAGAGCACCCAGTCCCTGAGTGCCCTGCT | R = A or G |
| 30 | rs7202877 | 1 | 0 | C | C | major | AGGCGCGCTCCGAACTCCGAGTGGGCGTCTTCTGTGAC<br>GTCAGGGCGTGTGTGGCTTTTTAGGGCTGGCCGGTGGGGC | B = C or G or T |
| 31 | rs2290400 | 0 | 1 | G | C | major | AGCGATTAATCTTCAATAGGAGCTGGCTCACAGAGAGGGA<br>AAGAGTCAGTGGGAGGTAAGGCCCTGAGATCCTTAACTCT | R = A or G |
| 32 | rs7221109 | 1 | 0 | C | C | major | TTGCCCAGCTTCTATTCTGTAATATATTGTATTAGTCACT<br>GGGGCACAAATATGAAAGCCAACACATATTTCTTCAGGAC | Y = C or T |
| 33 | rs45450798 | 0 | 1 | C | G | major | CATCTCTGCCTTGTCTCTTTATATGCCACATAAGATTTCT<br>CATAAGGCTTAAGTATTTTAAAGGGGGCAGTTATCATTTA | S = C or G |
| 34 | rs763361 | 1 | 0 | A | A | major | TCCTCTCTTGTATCATCCATGGATTGATTGGTAGGTTGAC<br>GGTAGAGATGGGACTTCTATAGTTATTGGGTGCCTAGAAA | H = A or C or T |
| 35 | rs425105 | 0 | 1 | A | T | major | AGGAGTTTTGGGGAGGACTAGAAGGAGGTGCTTACCATAG<br>GGACTGGGGCTGGGTCAGAGCTTTGGCGGGGACTTTTGAG | R = A or G |
| 36 | rs2281808 | 1 | 0 | C | C | major | TCCCATTTGGGTTTCTCAACATTAGTTTACAATGTGGATT<br>CTCTGACCCCATGGAGTCCCAGCATTCAAATAATCTACAG | Y = C or T |
| 37 | rs3788013 | 1 | 0 | A | A | minor | GGTGAAAAAAGAGAAAAGCTGCTCAGCCTCATGGGTGTGC<br>TGTTGGGGTGGAGCTCTTGCAGGTGTCAAGACTGATGGTT | M = A or C |
| 38 | rs5753037 | 1 | 0 | A | A | major | CCAGGTATCAGTATTATTGTAATATTCCCTTTATCAAAAA<br>CTATAACTGAAATTTATAGGTAAGAGTTTACAGTAAGCAG | Y = C or T |
| 39 | rs229541 | 0 | 1 | A | T | minor | TAGGGGGTTAAAGGCCCCTCTTAGTGAAGGGCAAAGATG<br>TTATCAGAAATTGGGTTAGAGGGCCCAAATGAAGAAGGTTG | Y = C or T |

TABLE 2-continued

Overview of all 42 SEQ ID NOs. containing one type 1 diabetes
susceptibility SNP marker (depicted as rs-number).

| SEQ ID No. | SNP | FWD (+) | REV (-) | Risk allele | REV. Annot. of risk allele | Frequency of risk allele | Sequence | |
|---|---|---|---|---|---|---|---|---|
| 40 | rs5979785 | 1 | 0 | T | T | major | TGTAATTCTCATATTACTATCATTGTTATGTATTCTTTCT TCCGAATGAAGAATGAAGGTACCATCCACTGACACCACAG | Y = C or T |
| 41 | rs2664170 | 1 | 0 | G | G | minor | GTCACAGTGTTTTTCAACCAGGGATGGTATAATTCCTCTC GGAGCATCTGAAAATATGTGGGTTTTGCTTGTTATAAAGG | R = A or G |
| 42* | rs1004446 | 0 | 1 | T | A | major | GGATGGGGTGTGCAGGAAAGGCCATTGTGGAGAGGGTTCT CTTTAGGGCTGCACAAAGCCACTGAGGCTTTTGCAAGGAA | Y = C or T |

FWD: forward strand (+); 0 = no, 1 = yes
REV: reverse strand (-); 0 = no, 1 = yes
REV Annot.: reverse annotation
Frequency of risk allele gives the frequency of the risk allele without REV. annotation
minor: refers to the frequency at which the second most common allele occurs in a given population The term "heterozygous" means having two different alleles of a given SNP (one on each chromosome), whereas the term "homozygous" means having the same allele of a SNP on both chromosomes.

The sum of the obtained multiplication products from step (a) and the score number 3.15 for a subject who has the HLA DR4-DQ8/DR4-DQ8 genotype or 3.98 for a subject who has the HLA DR3/DR4-DQ8 genotype from step (b) produce the genetic risk score of the present invention.

In this context, the term "score number" may not be confused with the term "score weight". The score number is the number (e.g. 3.15) only assigned to subjects having the HLA DR4-DQ8/DR4-DQ8 genotype if SNP rs17426593, SNP rs2187668, and SNP rs7454108) are being genotyped or the number (e.g. 3.98) assigned to subjects having the HLA DR3/DR4-DQ8 genotype if SNP rs17426593, SNP rs2187668, and SNP rs7454108 are being genotyped.

As an example, the genetic risk score for a subject being analyzed for all 41 SNPs of Table 1 with the HLA DR3/DR4-DQ8 genotype, being homozygous for the HLA class I risk allele of rs1264813 (score weight 0.43), being homozygous for the risk allele of rs2395029 (score weight 0.92), being homozygous for the non-risk allele of rs2476601 (score weight 0.76) and heterozygous for the risk alleles of the remaining SNPs analyzed of Table 1 is calculated as follows:

$$GRS = 3.98^{(=score\ number)} + (2^{(=number\ of\ risk\ alleles)} *$$
$$0.43^{(=score\ weight)}) + (2*0.92) + (0*0.76) + (1*0.16) +$$
$$(1*0.22) + (1*0.16) + (1*0.16) + (1*0.19) + (1*0.11) +$$
$$(1*0.19) + (1*0.19) + (1*0.14) + (1*0.15) + (1*0.05) +$$
$$(1*0.15) + (1*0.17) + (1*0.23) + (1*0.47) + (1*0.15) +$$
$$(1*0.25) + (1*0.65) + (1*0.06) + (1*0.36) + (1*0.24) +$$
$$(1*0.13) + (1*0.13) + (1*0.15) + (1*0.15) + (1*0.20) +$$
$$(1*0.19) + (1*0.25) + (1*0.15) + (1*0.09) + (1*0.12) +$$
$$(1*0.21) + (1*0.07) + (1*0.16) + (1*0.15) + (1*0.18) +$$
$$(1*0.09) + (1*0.14) = 13.69.$$

A genetic risk score of e.g. 13.69 obtained by the method of the present invention indicates a risk score above the cut-off value 13.6. Subjects with a value above 13.6 have a risk of about 8.1% to develop type 1 diabetes by age 6 years according to FIG. 10 depicting different risk score cut-off values indicating the risk of developing multiple islet autoantibodies in TEDDY children with the HLA DR3/DR4-

DQ8 or DR4-DQ8/DR4-DQ8 genotypes established by applying the TEDDY score using all 41 SNPs from Table 1 to the TEDDY cohort.

The term "precisely" refers to the determination of a genetic risk score obtained by the method of the present invention indicating a certain risk score cut-off value which is indicative that a subject is at risk of developing type 1 diabetes by certain years of age, by 1, 1.5, 2, 2.5, 3, 3.5, 4, 4.5, 5, 5.5, 6, 6.5, 7, 7.5, 8, 8.5, 9, 9.5 or by 10 years of age, preferably by 6 years of age.

In general, the subject being at risk to develop type 1 diabetes may be a human.

The present invention may comprise an adult or non-adult as a subject, whose genetic risk score is determined by the method of the present invention. Preferably, the present invention encompasses a newborn or an infant, whose genetic risk score is determined by the method of the present invention. More preferably, the subject is Caucasian, in particular a Caucasian newborn or infant.

The term "adult" refers to a person with an age above 18 years. Vice versa a non-adult refers to a person with an age below 18 years.

The term "newborn" refers to a baby which is not older than 1 month. Preferably, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h or 1 day, 2 days, 3 days, 4 days, 5 days, 6 days, 7 days (1 week), or 2 weeks, 3 weeks, 4 weeks.

According to the Commission Directive 91/321/EEC of 14 May 1991 on infant formulae and follow-on formulae, article 1.2(a), the term "infant" means children under the age of 12 months when appropriate complementary feeding is introduced after breast feeding and/or giving baby food in the first months of life. This definition is adopted in the present specification. Preferably, an infant of the present invention is older than 1 month and under the age of 12 months.

The present invention may further comprise a newborn or an infant not older than 3 months as a subject whose genetic risk score is determined by the method of the present invention. If a newborn is preferred, newborn screening for genetic, endocrine, and metabolic disorder is routinely done within the first days after birth at obstetric clinics or pediatrician offices, using a few drops of blood from the heel onto filter paper cards, or venous blood taken from the back of the hand. The dried filter paper blood spots are sent to specialized laboratories.

Additionally, the present invention may also comprise that if the genetic risk score is at least 13.9, it is indicative that said newborn or said infant may have an at least 10% genetic risk to develop type 1 diabetes by an age of 6 years.

Further, a genetic risk score of at least 14.0, 14.2, 14.3, 14.4, 14.6, 14.8, 15.1 and 15.4 is indicative that said newborn or said infant may have an at least 10% genetic risk to develop type 1 diabetes by a certain age, preferably by an age of 6 years (FIG. 10).

In detail, a genetic risk score cut-off value of 13.9 is indicative that said newborn or said infant may have an 8.6% (95% confidence interval of: 7.1 to 10.1%, such as 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 and 10.0%) genetic risk to develop type 1 diabetes by a certain age, preferably by an age of 6 years. A genetic risk score cut-off value of 14.0 is indicative that said newborn or said infant may have an 9.1% (95% confidence interval of: 7.5 to 10.8%, such as 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6 and 10.7%) genetic risk to develop type 1 diabetes by a certain age, preferably by an age of 6 years. A genetic risk score cut-off value of 14.2 is indicative that said newborn or said infant may have an 10.1% (95% confidence interval of: 8.2 to 11.9%, such as 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7 and 11.8%) genetic risk to develop type 1 diabetes by a certain age, preferably by an age of 6 years. A genetic risk score cut-off value of 14.3 is indicative that said newborn or said infant may have an 10.2% (95% confidence interval of: 8.2 to 12.2%, such as 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0 and 12.1%) genetic risk to develop type 1 diabetes by a certain age, preferably by an age of 6 years. A genetic risk score cut-off value of 14.4 is indicative that said newborn or said infant may have an 11.0% (95% confidence interval of: 8.7 to 13.3%, such as 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1 and 13.2%) genetic risk to develop type 1 diabetes by a certain age, preferably by an age of 6 years. A genetic risk score cut-off value of 14.6 is indicative that said newborn or said infant may have an 11.9% (95% confidence interval of: 9.2 to 14.5%, such as 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3 and 14.4%) genetic risk to develop type 1 diabetes by a certain age, preferably by an age of 6 years. A genetic risk score cut-off value of 14.8 is indicative that said newborn or said infant may have an 12.0% (95% confidence interval of: 8.9 to 15.1%, such as 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, and 15.0%) genetic risk to develop type 1 diabetes by a certain age, preferably by an age of 6 years. A genetic risk score cut-off value of 15.1 is indicative that said newborn or said infant may have an 13.2% (95% confidence interval of: 9.2 to 17.1%, such as 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9 and 17.0%) genetic risk to develop type 1 diabetes by a certain age, preferably by an age of 6 years. A genetic risk score cut-off value of 15.4 is indicative that said newborn or said infant may have an 12.2% (95% confidence interval of: 6.7 to 17.4%, such as 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2 and 17.3%) genetic risk to develop type 1 diabetes by a certain age, preferably by an age of 6 years.

Preferably, if the genetic risk score cut-off value (genetic risk score) is at least 14.4, it is indicative that said newborn or said infant may have an at least 10.0% genetic risk to develop type 1 diabetes by a certain age, preferably by an age of 6 years.

Figure 9A:
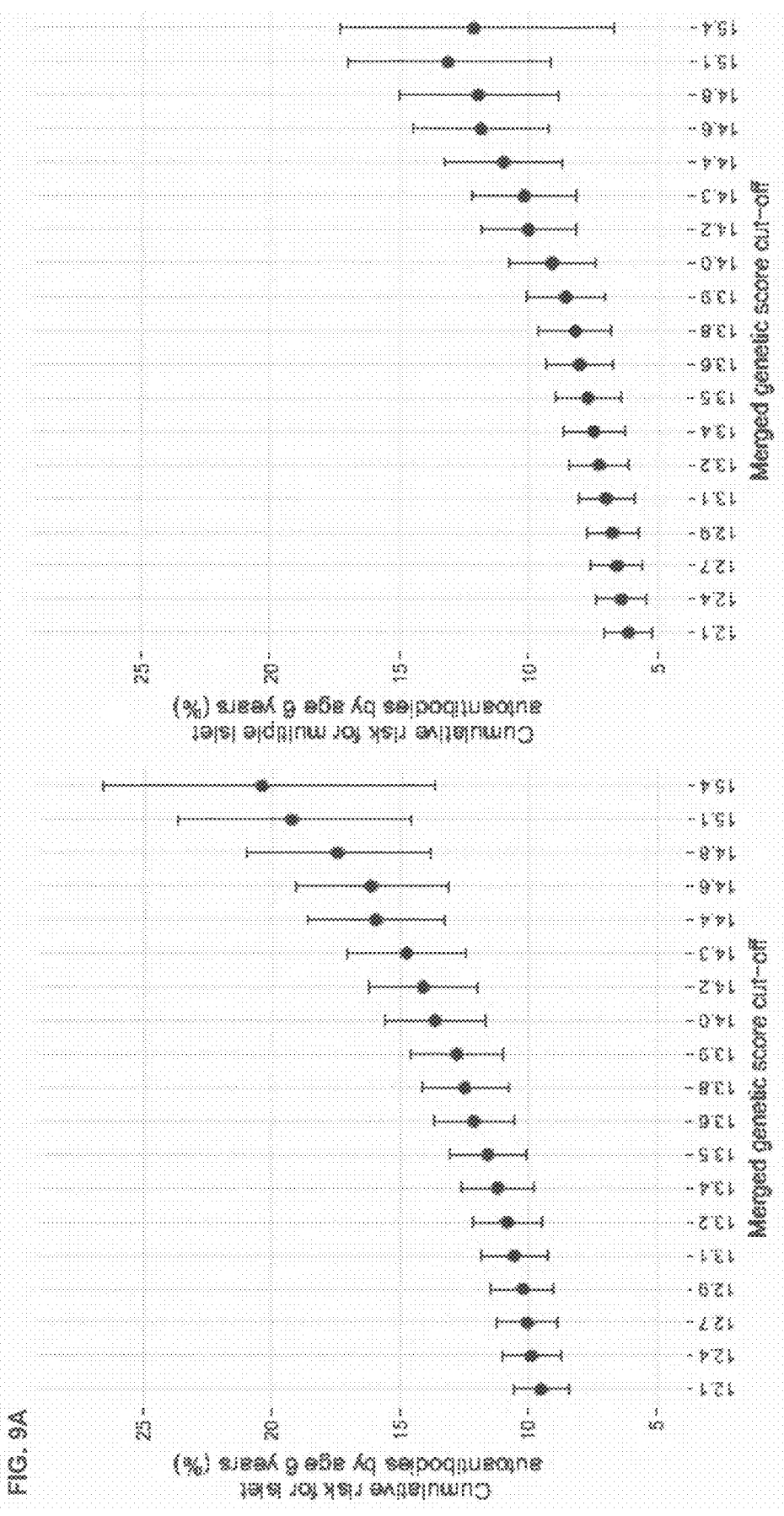
FIGS. 9A-9B: Risk of developing islet autoantibodies
(FIG. 9A) and the proportion of cases positive for islet
autoantibodies (sensitivity.

The risk score cut-off value (genetic risk score) of 14.4 determines an at least 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3% risk to develop type 1 diabetes by 6 years of age. The risk score cut-off value (genetic risk score) of 14.4 indicates a risk from 8.7% to 13.3%, 9.0% to 13.0%, 9.5% to 12.5%, 10.0% to 12.0%, 10.5% to 11.5% to develop type 1 diabetes by 6 years of age. Preferably, the risk score cut-off value (genetic risk score) of 14.4 indicates a 11% (95% Cl, 8.7%-13.3%) risk that a subject who has the HLA DR3/DR4-DQ8 or DR4-DQ8/DR4-DQ8 genotype develops multiple islet autoantibodies at 6 years of age (FIG. 9A right) and a 16% (95% Cl, 13.3%-18.6%) risk that a subject who has the HLA DR3/DR4-DQ8 or DR4-DQ8/DR4-DQ8 genotype develops islet autoantibodies at 6 years of age (FIG. 9A left).

By identifying subjects (said subjects having a genetic risk score obtained by step (a), (b) and (c) of e.g. 14.4 by the method of the present invention) having an at least 10% risk for developing type 1 diabetes by 6 years of age, parents of the subject are asked to allow their children to participate in a primary prevention randomized controlled trial. In this context "the randomized controlled trial" aims to prevent beta-cell autoimmunity or type 1 diabetes by oral insulin immune tolerance induction.

Figure 20B:
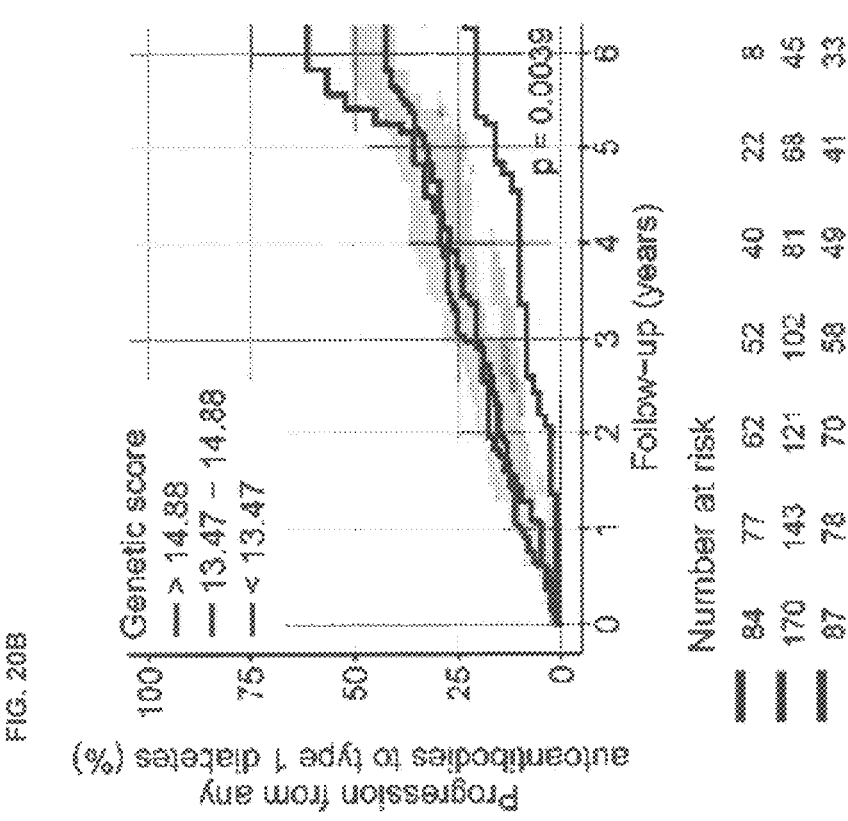
FIGS. 20A-20C: Cumulative risks of (FIG. 20A) development of multiple islet autoantibodies after first appearance of any autoantibodies, (FIG. 20B) development of type 1 diabetes after first appearance of any autoantibodies, and (FIG. 20C) development of type 1 diabetes after first appearance of multiple autoantibodies, in children with the HLA DR3/DR4-DQ8 or the HLA DR4-DQ8/DR4-DQ8 genotype. P-values were calculated using log-rank tests.
Figure 20A:
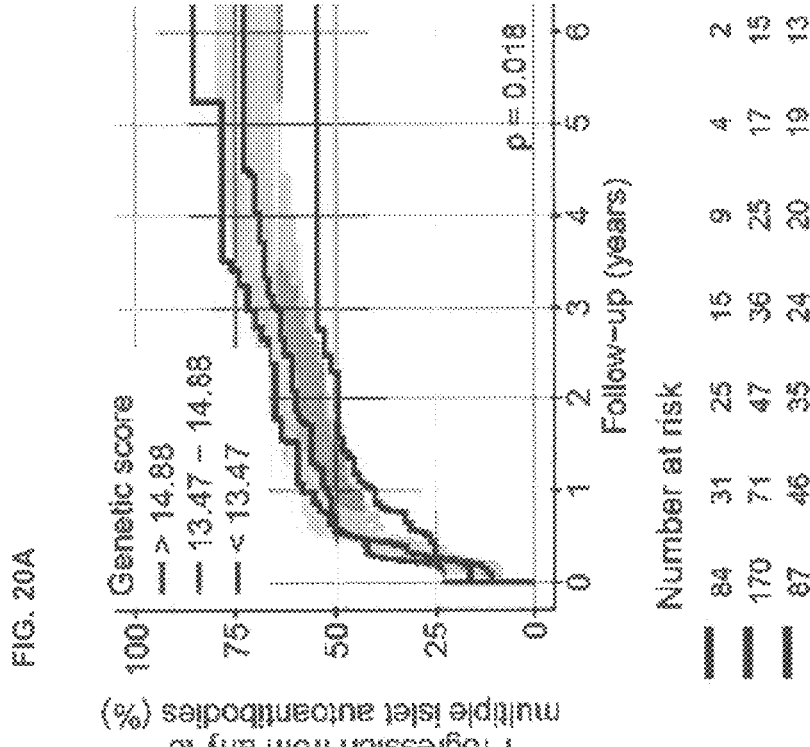
Figure 20C:
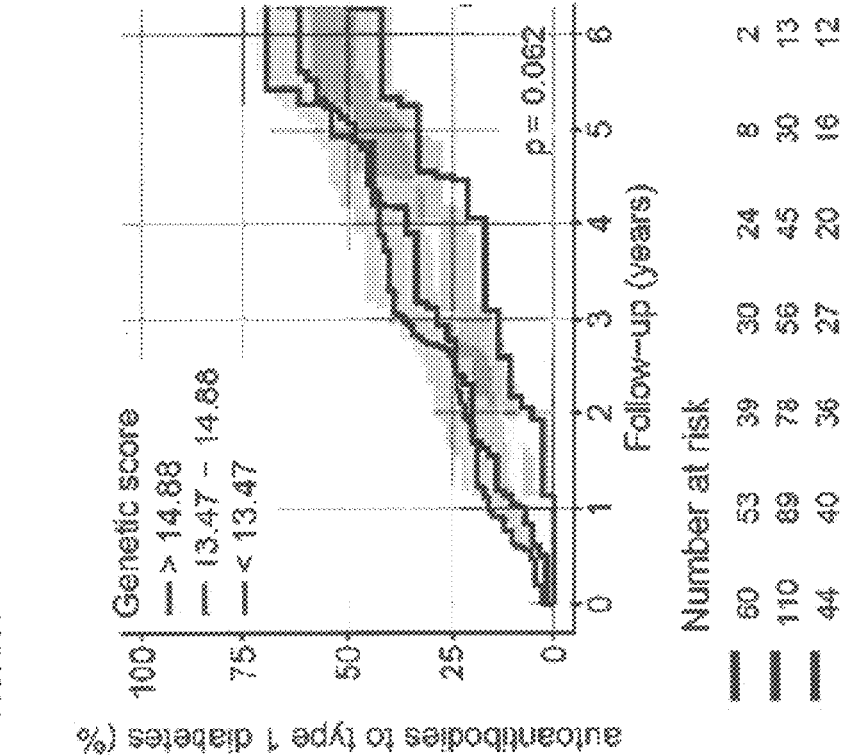

Further, the TEDDY score (merged score) is predictive of the rate of progression to type 1 diabetes. In the autoantibody positive children with a genetic risk score in the lowest quartile (genetic risk score <13.47), there was slower progression from single to multiple islet autoantibodies, single autoantibodies to diabetes, and multiple islet autoantibodies to diabetes (FIGS. 20A-20C). In a Cox proportional hazards analysis, an increased genetic risk score and an earlier age of islet autoantibody development were associated with faster progression to subsequent stages of autoimmunity and type 1 diabetes (FIG. 21). Vice versa, a low genetic risk score may be used to identify a subset of islet autoantibody positive children with slower progression to clinical type 1 diabetes. The prediction based on using the TEDDY score did not include the HLA class II genes, suggesting the impact of genetic variants on progress is independent of the HLA DR3/4-DQ8 of DR4-DQ8/DR4-DQ8 genotypes in these TEDDY participants. The method of the present invention is therefore also applicable, when the rate of progression to type 1 diabetes may be investigated.

The sample used to determine the genetic risk score of a subject may be a blood sample or saliva sample. If blood samples are used, the blood is preferably taken from the heel, the hand (in particular venous blood is taken from the back of the hand) or the arm. In infants or older children the blood sample is preferably taken from the arm. Samples such as amniotic fluid, hair or buccal smear may also be used to determine the genetic risk score of a subject.

While there have been significant improvements in insulin analogs and insulin delivery systems, such as continuous subcutaneous insulin infusions with insulin pumps, normal glucose control, particularly in children, is rarely achieved. Therefore, individuals with T1 D remain at risk for chronic secondary end-organ complications including but not limited to visual impairment and blindness, renal failure vascular disease and limb amputation, peripheral neuropathy, and stroke. They are also at high risk for acute complications such as severe hypoglycemia, recurrent ketoacidosis, and others. Thus, prevention of beta-cell autoimmunity and T1D would clearly represent a significant advancement.

Since self-tolerance is achieved by T cell exposure to self-antigens in the thymus or in the periphery (i.e. outside the thymus or bone marrow, in secondary lymphoid tissues such as lymph nodes, gut and spleen) in a manner that deletes autoreactive effector T cells and induces regulatory T cells and immunological tolerance by administration of antigen under appropriate conditions[16,17], evidence is now emerging in humans that these approaches may be effective in chronic inflammatory diseases such as multiple sclerosis, allergy, and T1D as well.

If infant tolerance to beta-cell autoantigens could be enhanced, this could prevent or delay the onset of pre-symptomatic type 1 diabetes (defined as loss of tolerance and multiple beta-cell autoantibodies), and hence prevent or delay disease diagnosis. The key here is "infant", the time when the natural mechanisms of immune tolerance are fully active as the child becomes tolerant to commensal microorganisms and dietary components.

The present invention may comprise immune tolerance to beta-cell autoantigens before the start of beta-cell autoimmunity as primary prevention for T1D through regular exposure of insulin.

Thus, the present invention relates to a pharmaceutical composition comprising insulin and a pharmaceutical acceptable carrier for use in a method for preventing type 1 diabetes in a subject having a genetic risk score as determined by the method of the present invention.

The pharmaceutical composition used in present invention may contain at least insulin. The pharmaceutical composition used in the present invention may contain at least insulin and a pharmaceutical acceptable carrier. The pharmaceutical composition comprising insulin and a pharmaceutical acceptable carrier may be administered to a subject, as described herein.

The term "insulin" refers to a peptide hormone produced by beta cells of the pancreatic islets. It regulates the metabolism of carbohydrates, fats and protein by promoting the absorption of, especially, glucose from the blood into fat, liver and skeletal muscle cells.

There is clear evidence from man and animal models that insulin is the key early and primary autoantigen of childhood diabetes. There is also a strong genetic rationale for loss of tolerance against insulin as a primary cause of T1D. Allelic variation in the insulin gene is associated with T1D and beta-cell autoimmunity via a mechanism of thymic T cell deletion. Polymorphisms in the INSULIN (INS) gene confer genetic risk for T1D by altering insulin expression in the thymus, thereby influencing immune tolerance to insulin and its precursors. Moreover, insulin autoimmunity is closely linked to the HLA DR4-DQ8 haplotype present in the majority of children who develop T1 D.

The term "pharmaceutically acceptable" refers to something being approved by a regulatory agency or other generally recognized pharmacopoeia for use in animals, and more particularly in humans.

The term "carrier" refers to a diluent, adjuvant, or vehicle with which the pharmaceutical composition is administered. Such pharmaceutical acceptable carriers can be sterile liquids, such as water and oils including those of petroleum, animal, vegetable or synthetic origin, such as peanut oil, soybean oil, mineral oil, sesame oil and the like. Water is a preferred carrier when the pharmaceutical composition is administered intravenously or orally. Saline solutions and aqueous dextrose and glycerol solutions can also be employed as liquid carriers, particularly for injectable solutions. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Where the composition is administered orally, the pharmaceutically acceptable carrier may also comprise filling substance such as microcrystalline cellulose of a total weight of 200 mg, which is formulated together with the insulin crystals in a hard gelatin capsule.

As used herein, the term "prevent" refers to the prevention of the recurrence or onset of one or more symptoms of a disorder in a subject, preferably T1 D.

Thus, the present invention comprises a pharmaceutical composition for use in the method for preventing type 1 diabetes in a subject having a genetic risk score as determined by the method of the present invention, wherein said method may comprise administering the pharmaceutical composition comprising a dose of insulin for 60 months (5 years) or less to a subject and wherein said dose may be effective to prevent type 1 diabetes in said subject. Preferably, a dose of insulin of the pharmaceutical composition is administered for 12 months (1 year), 18 months (1.5 years), 24 months (2 years), 30 months (2.5 years), 36 months (3 years), 42 months (3.5 years), 48 months (4 years), 54 months (4.5 years) or from 12 months to 60 months, 18 months to 60 months, 24 months to 60 months, 30 months to 60 months, 36 months to 60 months, 42 months to 60 months, 48 months to 60 months, 54 months to 60 months, or 18 months to 54 months, 24 months to 48 months, 30 months to 42 months, or 24 months to 36 months, 25 months to 35 months, 26 months to 34 months, 27 months to 33 months, 28 months to 32 months, 29 months to 31 months. More preferably, a dose of insulin of the pharmaceutical composition is administered for 30 months. The method of preventing type 1 diabetes by applying the pharmaceutical composition of the present invention comprising administering a dose of insulin for 60 months or less may start in the first year of life of a subject.

The dose of insulin of the pharmaceutical composition of the present invention used in the method for preventing type 1 diabetes may be from 50 to 100 mg. The dose of insulin of the pharmaceutical composition of the present invention used in the method for preventing type 1 diabetes may be from 50 to 100 mg, from 55 to 95 mg, from 60 to 90 mg, from 65 to 85 mg, from 65 to 80 mg. from 65 to 70 mg or 60 mg, 60.5 mg, 61 mg, 61.5 mg, 62 mg, 62.5 mg, 63 mg, 63.5 mg, 64 mg, 64.5 mg, 65 mg, 65.5 mg, 66 mg, 66.5 mg, 67 mg, 67.5 mg, 68 mg, 68.5 mg, 69 mg, 69.5 mg, 70 mg, or at least 50 mg, at least 60 mg, at least 65 mg, at least 66 mg, at least 67 mg. Preferably, the dose of insulin of the pharmaceutical composition of the present invention used in the method for preventing type 1 diabetes may be 67.5 mg.

Additionally, the present invention comprises that the pharmaceutical composition of the present invention may be administered daily.

The term "daily" means every day in a week having 7 days. Preferably, the pharmaceutical composition of the present invention is administered once a week, twice a week, three times a week, four times a week, five time a week, six times a week or seven times a week, or 1 to 7 days per week, 2 to 7 days per week, 3 to 7 days per week, 4 to 7 days per week. More preferably, the pharmaceutical composition of the present invention is administered 4 to 7 days per week, meaning either 4 days, or 5 days or 6 days or even 7 days per week. Only one capsule per day is administered, preferably in the morning between 7 and 10 am.

Further, said administration of the pharmaceutical composition may be performed by injection or by infusion. The pharmaceutical composition may be injected. This injection may be performed intraperitoneally, intravenously, subcutaneously or intramuscularly. In this context, the term "injection" refers to the administration of a liquid comprising for example insulin or any other type 1 diabetes antigen by applying a syringe and a hollow needle, which is pierced though the skin to be administered into the body.

The pharmaceutical composition may also be infused. In this context, the term "infusion" refers to a continuous, most commonly parenteral administration of liquid comprising for example insulin or any other type 1 diabetes antigen intravenously.

The pharmaceutical composition may also be taken orally. The oral administration refers to swallowing insulin crystals or any other type 1 diabetes antigen formulated with filing substances and contained in hard gelatin capsules with water or any other liquid used as a pharmaceutically acceptable carrier.

Thus, the present invention comprises that said administration of the pharmaceutical composition may be performed intraperitoneally, intravenously, subcutaneously, intramuscularly or orally. Preferably, said administration is performed orally. The preferred dose of 67.5 mg insulin of the pharmaceutical composition may be too highly dosed for another administration except for oral administration, because said dose of 67.5 mg insulin may not be digested in the stomach by injection or by infusion as it is done for the oral administration, instead being directly transferred to the blood stream when intravenous infusion or any injection is applied.

The subject, who becomes the pharmaceutical composition of the present invention administered, may be an infant. Said infant may be 2 to 10 months old at the beginning of the administration of the pharmaceutical composition. Preferably, 3 to 9 months, or 4 to 8 months, 4 to 7 months, 4 to 6 months, 4 to 5 months or at least 2 months, at least 3 months, at least 4 months, at least 5 months. More preferably, said infant is 4 to 7 months old at the beginning of the administration of the pharmaceutical composition.

Additionally, the present invention may also provide a pharmaceutical composition comprising insulin and a pharmaceutical acceptable carrier for use in a method for preventing type 1 diabetes in a subject having a genetic risk score as determined by the method of the present invention, wherein said method comprises administering the pharmaceutical composition comprising different doses of insulin to a subject for 60 months or less. The different doses of insulin may be seen as a dose increase, which may start in the first year of life of a subject. The pharmaceutical composition for use in a method for preventing type 1 diabetes in a subject having a genetic risk score as determined by the method of the present invention, wherein said method comprises administering a first dose of insulin for 1 or 2 or 3 month(s) and/or administering a second dose of insulin for another 1 or 2 or 3 month(s) and administering a third dose (highest dose) of insulin for another 12 to 60 months, or 18 months to 60 months, 24 months to 60 months, 30 months to 60 months, 36 months to 60 months, 42 months to 60 months, 48 months to 60 months, 54 months to 60 months, or 18 months to 54 months, 24 months to 48 months, 30 months to 42 months, or 24 months to 36 months, 25 months to 35 months, 26 months to 34 months, 27 months to 33 months, 28 months to 32 months, 29 months to 31 months and wherein said doses are effective to prevent type 1 diabetes in said subject, may also be provided by the present invention Preferably, the third dose (highest dose) of insulin is administered for 30 months. The highest dose of insulin may already be reached in the first year of life of a subject.

The present invention may also include a pharmaceutical composition comprising insulin and a pharmaceutical acceptable carrier for use in a method for preventing type 1 diabetes in a subject having a genetic risk score as determined by the method of the present invention, wherein said method comprises administering the pharmaceutical composition comprising a first dose of insulin for 2 months, followed by a second dose of insulin for another 2 months, followed by a third dose of insulin for another 30 months.

Said first dose of insulin may be from 5 to 10 mg, from 5.5 to 9.5 mg, from 6 to 9 mg, from 6.5 to 8.5 mg, from 7 to 8 mg. Preferably, said first dose of insulin may be 7.5 mg. Said second dose of insulin may be from 15 to 30 mg, from 20 to 25 mg, from 20.5 to 24.5 mg, from 21 to 24 mg, from 21.5 to 23.5 mg, 22 to 23 mg. Preferably, said second dose of insulin may be 22.5 mg. Said third dose of insulin may be from 60 to 75 mg, from 65 to 70 mg, from 65.5 to 69.5 mg, from 66 to 69 mg, from 66.5 to 68.5, from 67 to 68 mg. Preferably, said third dose of insulin may be 67.5 mg. Said first and/or said second dose of insulin are more or less for safety than efficacy reasons and may be omitted if not necessary or needed.

Thus, the present invention may also comprise a pharmaceutical composition comprising insulin and a pharmaceutical acceptable carrier for use in a method for preventing type 1 diabetes in a subject having a genetic risk score as determined by the method of the present invention, wherein the first dose of insulin is from 5 to 10 mg, and wherein the second dose of insulin is from 15 to 30 mg, and wherein the third dose of insulin is from 60 to 75 mg. Preferably, the present invention may also encompass a pharmaceutical composition comprising insulin and a pharmaceutical acceptable carrier for use in a method for preventing type 1 diabetes in a subject having a genetic risk score as determined by the method of the present invention, wherein the first dose of insulin is 7.5 mg, and wherein the second dose of insulin is 22.5 mg, and wherein the third dose of insulin is 67.5 mg.

The conversion of the mg unit into international unit (IU) for the 7.5 mg of the oral insulin results in 215.3 IU insulin in a 0.5 mL capsule, the 22.5 mg dose contains 645.8 IU insulin in a 0.5 mL capsule, and the 67.5 mg dose has 1937.3 IU insulin in the 0.5 mL capsule.

The inclusion criteria for the treatment with insulin (in particular oral insulin) or for the treatment comprising a dose increase of insulin (in particular oral insulin) may comprise enrolling an infant being between 4 months and 7 months at the time of randomization in this trial. Said infant has to be identified with increased type 1 diabetes risk for enrollment into primary prevention trials using insulin, preferably oral insulin. The increased risk comprises having a predicted genetic risk of >10% to develop beta-cell auto-immunity by an age of 6 years:

a) for infants without a first degree family history of type 1 diabetes, high genetic risk is defined as a HLA DR3/DR4-DQ8 or HLA DR4-DQ8/DR4-DQ8 genotype, and a genetic risk score that is >14.4 corresponding to the upper $75^{th}$ centile of children with these HLA class II genotypes, b) for infants with a first degree family history of type 1 diabetes, high genetic risk is defined as having HLA DR4 and DQ8, and none of the following protective alleles: DRB1*1501 (rs3129889) and/or DQB1*0503 (rs1794265).

Additionally, solid foods have to be introduced to said infants and a written informed consent signed by either parent(s) or legal guardian(s) has to be submitted to enroll said infant into the prevention trial.

Participants meeting any of the following criteria will not be eligible for inclusion into the study:

a) concomitant disease or treatment which may interfere with assessment or cause immunosuppression, as judged by the investigators, b) any condition that could be associated with poor compliance.

Potential study subjects will be identified through the identification of infants with increased type 1 diabetes risk for enrollment into primary prevention trials. Infants are tested for genetic risk of type 1 diabetes based on risk scores derived from SNPs that define HLA DR3, HLA DR4, and HLA DQ8 alleles (rs17426593, rs2187668, rs7454108 of Tab. 3) as well as SNPs from HLA class I (rs1264813, rs2395029 of Tab. 3), and non-HLA type 1 diabetes susceptibility genes (from rs2476601 to rs2664170 of Tab. 3), and from HLA class II protective alleles (rs3129889 for DRB1*1501, rs1794265 for DQB1*0503) as mentioned for the method of the present invention. Testing will be offered either at delivery (cord blood), or together with the regular newborn screening, or at a pediatric baby-visit before the age of 3 months. Infants with a predicted risk for type 1 diabetes of >10% to develop beta-cell autoimmunity by an age of 6 years and who fulfill the inclusion criteria as stated above will be offered to participate in the primary prevention trial with oral insulin.

The administration of insulin, preferably oral insulin, will be conducted only among those who consent to participate. Infants will be randomized to receive either oral insulin or placebo along with close monitoring for beta-cell autoimmunity and abnormal glucose tolerance or diabetes. The study treatment will be given orally as a powder spread on a small quantity meal serving e.g. with infant formula, tea spoon of water, breast milk, commercial baby food or yogurt. The insulin will be provided in a capsule box a 32 hard gelatin capsules containing insulin crystals or placebo. The investigational product (oral insulin or placebo) will be self-administered by the child's parents or guardians as content of one capsule per day. Treatment will be administered preferably in the morning (7-10 am). Participants will be observed for 2 hours after administration of the study drug at each visit starting from baseline to the age of 30 months.

Participants will be withdrawn from study treatment if they:

a.) develop diabetes (study endpoint), b.) report moderate to severe intolerance of study treatments, c.) develop an intercurrent illness deemed incompatible with the study, d.) withdraw consent.

During the course of the study, participants will undergo assessments for beta-cell autoimmunity, glucose levels, beta-cell function, and their overall health and well-being. In children with beta-cell autoimmunity, oral glucose tolerance test (OGTT) will be performed at six month intervals starting from age 3.0 years.

The present invention may also comprise a pharmaceutical composition comprising insulin, which is administered to a subject, in particular to an infant, which does not have a first-degree family history of type 1 diabetes. In other words, a pharmaceutical composition, which is administered to a subject, in particular to an infant without a first degree family history of type 1 diabetes is also comprised by the present invention. Said infant without a first degree family history of type 1 diabetes has the protective allele DRB1*1501 and/or DQB1*0503.

The present invention may further encompass a pharmaceutical composition comprising insulin, wherein said pharmaceutical composition may be in the form of a multiple-dosage-kit containing sufficient amounts of administration doses of insulin for effectively preventing type 1 diabetes in a subject.

In this context, the term "multiple-dosage-kit" refers to a kit containing different doses of insulin, which are being administered to a subject (in particular an infant of 4 to 7 months old) of the present invention. Said multiple-dosage-kit may be used for the treatment comprising a dose increase. The first dose of insulin used in the multiple-dosage-kit may be from 5 to 10 mg, from 5.5 to 9.5 mg, from 6 to 9 mg, from 6.5 to 8.5 mg, from 7 to 8 mg. Preferably, the first dose of insulin used in the multiple-dosage-kit may be 7.5 mg. The second dose of insulin used in the multiple-dosage-kit may be from 15 to 30 mg, from 20 to 25 mg, from 20.5 to 24.5 mg, from 21 to 24 mg, from 21.5 to 23.5 mg, 22 to 23 mg. Preferably, the second dose of insulin used in the multiple-dosage-kit may be 22.5 mg. The third dose of insulin used in the multiple-dosage-kit may be from 60 to 75 mg, from 65 to 70 mg, from 65.5 to 69.5 mg, from 66 to 69 mg, from 66.5 to 68.5, from 67 to 68 mg. Preferably, the third dose of insulin used in the multiple-dosage-kit may be 67.5 mg.

The present invention also comprises a kit for use in a method of determining whether a subject is at risk of developing type 1 diabetes by determining the genetic risk score (GRS) of a subject according to the method of the present invention mentioned above, the kit comprising means for analyzing 41 SNPs as listed in Table 1 in a sample from a subject and determining, whether the determined SNP is present heterozygously or whether the determined SNP is present homozygously, and further comprising means for detecting whether said subject, whose sample is investigated has a HLA DR4-DQ8/DR4-DQ8 genotype or whether said subject has a HLA DR3/DR4-DQ8 genotype.

Said means are preferably provided in one or more containers or vials in a kit (pharmaceutical pack), which may be associated with a notice in the form prescribed by a governmental agency regulating the manufacture, use or sale of pharmaceuticals or biological products, reflecting approval by the agency of the manufacture, use or sale of the product for human administration or diagnostics. In this context, the term "means" refers to tools, which are applied in the field of diagnostics for detecting certain characteristics (e.g. zygosity of alleles, genotype of a subject) of a subject being investigated.

In this context, the subject may be an adult or non-adult. Preferably, the subject is a newborn or an infant. More preferably, said newborn or said infant is not older than 3 months.

The sample applied in the kit and being investigated may be a blood sample or saliva sample. If blood samples are used, the blood is preferably taken from the heel, the hand (in particular venous blood is taken from the back of the hand) or the arm. In infants or older children the blood sample is preferably taken from the arm. Samples such as amniotic fluid, hair or buccal smear may also be used in the kit.

Additionally, the present invention also provides a type 1 diabetes antigen for use in a method of immunizing a subject against type 1 diabetes having a genetic risk score as determined by the method of the present invention. The type 1 diabetes antigen may act immunologically and may not act as a hormone in order to lower the blood sugar level. Immune tolerance to beta-cell autoantigens through regular exposure of a type 1 diabetes antigen to a subject, preferably through regular exposure of oral insulin may be induced. This refers to the process of "immunization", which refers to the process by which a subject's immune system becomes fortified against an agent (in particular a type 1 diabetes antigen). Regular exposure of type 1 diabetes antigen throughout the susceptible period in life (starting before the end of the first year and administering for preferably 2.5 years), where beta-cell autoimmunity usually initiates may tolerize against a type 1 diabetes antigen and train the body's immune system to recognize the treatment product without reacting to it. This immune tolerance induction therapy may lead to the prevention of beta-cell autoimmunity.

Said type 1 diabetes antigen may be selected from the group consisting of insulin, proinsulin, insulin analog, or peptides thereof. Proinsulin is the prohormone precursor to insulin made in the beta cells of the islets of Langerhans, which refers to specialized regions of the pancreas. Even though proinsulin and insulin have structural differences, proinsulin demonstrates some affinity for the insulin receptor. It would actually be expected to be better if proinsulin did not bind to the receptor and was hormonally inactive since this might be expected to be safer. Proinsulin has 81 residues and is formed by three distinct chains. The A chain, B chain, and the area connecting the two named the C-peptide. Proinsulin exhibits three disulfide bonds which are necessary to give mature insulin the correct structure. Between chain A and B there are two of these disulfide bonds, and one is an intra-A chain bond[18]. Mature insulin occurs from proinsulin by post translational modification in the beta cells of the islets of Langerhans. The C-peptide is cleaved from proinsulin when proinsulin is transported through the Golgi apparatus, thereby resulting in mature insulin.[19]

Insulin analogs are altered forms of insulin, different from any occurring in nature, but still available to the human body for performing the same action as human insulin. Insulin analogs may comprise but are not limited to insulin lispro (Humalog), insulin aspart (NovoLog/NovoRapid), insulin glulisine (Apidra), insulin detemir (Levemir), insulin deglu-dec (Tresiba), insulin glargine (Lantus), NPH insulin (Neutral Protamine Hagedorn) or non-glucose lowering analogs. These insulin analogs are known by the skilled man in the art. Animal insulin of different mammals is also very similar to human insulin. Thus, porcine insulin having only a single amino acid variation from the human insulin or bovine insulin varying by three amino acids to human insulin may also be included as insulin analogs.

The present invention also comprises said type 1 diabetes antigen for use in the method of immunizing a subject against type 1 diabetes having a genetic risk score as determined by the method of the present invention, wherein said method comprises administering a dose of type 1 diabetes antigen for 60 months or less to a subject.

Preferably, a dose of type 1 diabetes antigen is administered for 12 months (1 year), 18 months (1.5 years), 24 months (2 years), 30 months (2.5 years), 36 months (3 years), 42 months (3.5 years), 48 months (4 years), 54 months (4.5 years) or from 12 months to 60 months, 18 months to 60 months, 24 months to 60 months, 30 months to 60 months, 36 months to 60 months, 42 months to 60 months, 48 months to 60 months, 54 months to 60 months, or 18 months to 54 months, 24 months to 48 months, 30 months to 42 months, or 24 months to 36 months, 25 months to 35 months, 26 months to 34 months, 27 months to 33 months, 28 months to 32 months, 29 months to 31 months. More preferably, a dose of type 1 diabetes antigen is administered for 30 months. The method of immunizing a subject against type 1 diabetes using a type 1 diabetes antigen of the present invention and comprising administering a dose of type 1 diabetes antigen for 60 months or less, preferably for 30 months may start in the first year of life of a subject.

The dose of type 1 diabetes antigen of the present invention used in the method of immunizing a subject against type 1 diabetes may be from 50 to 100 mg. The dose of type 1 diabetes antigen used in the method of immunizing a subject against type 1 diabetes may be from 50 to 100 mg, from 55 to 95 mg, from 60 to 90 mg, from 65 to 85 mg, from 70 to 80 mg or 60 mg, 60.5 mg, 61 mg, 61.5 mg, 62 mg, 62.5 mg, 63 mg, 63.5 mg, 64 mg, 64.5 mg, 65 mg, 65.5 mg, 66 mg, 66.5 mg, 67 mg, 67.5 mg, 68 mg, 68.5 mg, 69 mg, 69.5 mg, 70 mg, or at least 50 mg, at least 60 mg, at least 65 mg, at least 66 mg, at least 67 mg. Preferably, the dose of type 1 diabetes antigen used in the method of immunizing a subject against type 1 diabetes may be 67.5 mg.

Additionally, the present invention comprises that the type 1 diabetes antigen of the present invention may be administered daily.

Preferably, the type 1 diabetes antigen of the present invention is administered once a week, twice a week, three times a week, four times a week, five time a week, six times a week or seven times a week, or 1 to 7 days per week, 2 to 7 days per week, 3 to 7 days per week, 4 to 7 days per week. More preferably, the type 1 diabetes antigen of the present invention is administered 4 to 7 days per week, meaning either 4 days, or 5 days or 6 days or even 7 days per week.

Only one capsule per day is administered, preferably in the morning between 7 and 10 am.

Said administration of the type 1 diabetes antigen may be performed by injection or by infusion. The type 1 diabetes antigen may be injected. This injection may be performed intraperitoneally, intravenously, subcutaneously or intramuscularly. The type 1 diabetes antigen may also be infused. The type 1 diabetes antigen may also be taken orally.

Thus, the present invention comprises that said administration of the type 1 diabetes antigen may be performed intraperitoneally, intravenously, subcutaneously, intramuscularly or orally. Preferably, said administration of the type 1 diabetes antigen is performed orally.

The type 1 diabetes antigen of the present invention of a dose of 67.5 mg, preferably oral insulin of a dose of 67.5 mg, perfectly acts immunologically and does not act as a hormone in order to lower the blood sugar level. Preferably, a dose of 67.5 mg of oral insulin induces immune tolerance to beta-cell autoantigens and is perfectly used in the method of immunizing a subject against type 1 diabetes.

The subject, who becomes the type 1 diabetes antigen of the present invention administered, may be an infant. Said infant may be 2 to 10 months old at the beginning of the administration of the type 1 diabetes antigen. Preferably, 3 to 9 months, or 4 to 8 months, 4 to 7 months, 4 to 6 months, 4 to 5 months or at least 2 months, at least 3 months, at least 4 months, at least 5 months. More preferably, said infant is 4 to 7 months old at the beginning of the administration of the type 1 diabetes antigen.

The present invention may also comprise a method of immunizing a subject against type 1 diabetes antigen having a genetic risk score as determined by the method of the present invention comprising administering an effective amount of a type 1 diabetes antigen to said subject in need thereof.

The subject in need thereof may be an infant. Said infant may be 2 to 10 months old at the beginning of the administration of the type 1 diabetes antigen. Preferably, 3 to 9 months, or 4 to 8 months, 4 to 7 months, 4 to 6 months, 4 to 5 months or at least 2 months, at least 3 months, at least 4 months, at least 5 months. More preferably, said infant is 4 to 7 months old at the beginning of the administration of the type 1 diabetes antigen.

Also comprised by the invention may be the use of a type 1 diabetes antigen for the manufacture of a medicament for the therapeutic application in type 1 diabetes, wherein the type 1 diabetes antigen immunizes a subject against type 1 diabetes having a genetic risk score as determined by the method of the present invention.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, f.e. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publication s cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be had from the following examples, offered for illustrative purposes only. The examples are not intended to limit the scope of the present invention in any way.

EXAMPLES OF THE INVENTION

Hereinafter, the present invention is described in more detail and specifically with reference to the examples, which however are not intended to limit the present invention.

Material and Methods

Example 1: Study Design

The main objective of the study was to provide a paradigm for the enrollment of individuals who are genetically at risk for disease into studies of early prevention. In detail, the study tries to identify infants who have a 10% risk for developing beta-cell autoantibodies by age 6 years in order to ask the parents to allow their infant to participate in a primary prevention randomized controlled trial. The randomized controlled trial aims to prevent beta-cell autoimmunity by oral insulin immune tolerance induction (ITI).

Genetic scores were determined from multiple risk loci in individuals with the HLA DR3/DR4-DQ8 or DR4-DQ8/DR4-DQ8 genotypes, which confer the highest risk for type 1 diabetes. A limitation of previous applications of genetic scores for type 1 diabetes prediction was the inclusion of relatively few controls individuals who had these HLA genotypes. Therefore, in order to validate the robustness of the initial findings, we extended genetic scores to the UK Biobank data (https://www.ukbiobank.ac.uk/)[20]. Genetic scores were calculated in 4371 non-diabetic individuals from the UK Biobank and 781 patients with type 1 diabetes in the Wellcome Trust Case Control Cohort (WTCCC)[21] who had the HLA DR3/DR4-DQ8 or DR4-DQ8/DR4-DQ8 genotype and were of white British ancestry.

The same genetic scores were therefore applied to children with high risk HLA genotypes, who were enrolled in prospectively followed "The Environmental Determinants of Diabetes in the Young" (TEDDY) cohort.[22] Children in the TEDDY cohort are followed for the development of islet autoantibodies and diabetes, which provides the ability to assess genetic score stratification of the disease already at the pre-symptomatic stage. A family history of type 1 diabetes is known to increase the risk of developing islet autoantibodies, and therefore, the analysis was restricted to children without a family history of type 1 diabetes.

Example 2: TEDDY Cohort

The Environmental Determinants of Diabetes in the Young (TEDDY) is a prospective cohort study funded by the National Institutes of Health with the primary goal being to identify environmental causes of type 1 diabetes. It is conducted at three centers in the USA (Colorado, Georgia/Florida, and Washington) and three centers in Europe (Finland, Germany, and Sweden). The study design has been published in more detail elsewhere.[22] Between 1 Sep. 2004 and 28 Feb. 2010, a total of 421,047 newborn children or infants at an age of 0 to 3 months were screened for high-risk HLA genotypes for type 1 diabetes. HLA genotype screening was conducted using either a dried blood spot punch or a small whole blood lysate specimen.

In detail, before the screening for high-risk HLA genotypes parents or legal guardians of neonates or infants of the TEDDY cohort were asked about their interest to participate in the study. It was explained that type 1 diabetes is increasing in childhood and that prevention with oral insulin may help to train the immune system to develop tolerance and no autoimmune disease such as type 1 diabetes during early life. They were also informed that early diagnosis will allow optimal care and treatment and prevent potential complications. They were told that genetic testing for type 1 diabetes risk does not mean that they must participate in the prevention trial or follow-up study, and that if their newborn was found to have a high risk for type 1 diabetes, they will be contacted and offered the possibility to participate in the prevention or follow-up study with further informed consent.

Parents or guardians were given sufficient time to read the informed consents and have any questions answered. It was explained that participation in the project was voluntary and consent could be withdrawn at any time without providing a reason and without disadvantages by doing so.

Name, contact information of the parents, child's date of birth, gender, weight, delivery mode, gestational age, date of blood collection, mother's date of birth, first-degree family history of type 1 diabetes was then collected.

Newborn screening for genetic, endocrine, and metabolic disorders was routinely done within the first days after birth at obstetric clinics or pediatrician offices, using a few drops of blood from the heel onto filter paper cards, or venous blood taken from the back of the hand (Sweden). The dried filter paper blood spots were sent to specialized laboratories. Testing for type 1 diabetes risk was done via separate Freder1k filter paper cards, and offered to families together with the regular newborn screening as a supplemental test with separate consent. Alternatively, it was offered via filter paper cards at delivery (using cord blood), or at a pediatric visit before the age of 3 months. At least one and a maximum of two blood spots was collected for testing of type 1 diabetes risk.

Then, DNA was extracted from two 3 mm punches of one and a maximum of two dried blood spot(s) and then HLA genotype screening was performed.

After the screening, if high-risk HLA genotypes were detected in newborns or infants, the HLA genotypes were confirmed by the central HLA Reference Laboratory at Roche Molecular Systems (Oakland, CA) for enrolled subjects at 9 months of age. The present report included TEDDY children with the DR3-DQA1*0501-DQB1*0201/DR4-DQA1*030X-DQB1*0302 genotype (HLA DR3/DR4-DQ8) or DR4-DQA1*030X-DQB1*0302/DR4-DQA1*030X-DQB1*0302 genotype (HLA DR4-DQ8/DR4-DQ8), without a first-degree relative with type 1 diabetes, if at least one sample was obtained after birth. Written informed consent was obtained for all study participants from a parent or primary caretaker for genetic screening and to participate in the prospective follow-up. The study was approved by local institutional review boards and is monitored by an External Advisory Board established by the National Institutes of Health.

After the screening, the families of children with the high-risk HLA genotypes were invited to participate in the follow-up study in which blood samples were obtained every 3 months for the first 4 years and biannually thereafter for the analysis of islet autoantibodies (glutamic acid decarboxylase antibody [GADA], insulinoma antigen-2 [IA-2A], and insulin autoantibodies [IAA]) (see Example 3)

Example 3: TEDDY Study Outcomes

Islet autoantibodies (IAA, GADA, and IA-2A) were measured by radio-binding assays every 3 months for the first 4 years and biannually thereafter. In the US, autoantibodies were assayed at the Barbara Davis Center for Childhood Diabetes at the University of Colorado Denver reference laboratory. In Europe, autoantibodies were assayed at the University of Bristol, the UK reference laboratory. All radio-binding assays were performed as described in the prior art.[23] Samples positive for islet autoantibodies were retested at the second reference laboratory for confirmation. The outcome islet autoantibody positivity was defined as a positive result at both reference laboratories and by the presence of islet autoantibodies (GADA, IA-2A, or IAA) on two or more consecutive visits. The date of seroconversion to islet autoantibodies (time to first autoantibody) was defined as the date of drawing the first of the two consecutive samples positive for an autoantibody. The presence of persistent multiple islet autoantibodies was defined as the presence of at least two persistent and confirmed islet autoantibodies. The date of persistent multiple islet autoantibodies was defined as the date of drawing the first sample when the second persistent and confirmed islet autoantibody was detected.

Children with positive islet autoantibodies that were due to maternal IgG transmission were not considered to be positive for that autoantibody unless the child had a negative sample before the first positive sample or the autoantibody persisted beyond 18 months of age.

Example 4: Single Nucleotide Polymorphism (SNP) Typing

In the TEDDY study, SNPs of immune-related genes were genotyped using the Illumina ImmunoChip.[24] For SNPs rs11755527 (BACH2) and rs1004446 (INS), which were not available on the ImmunoChip, the SNPs rs3757247 (BACH2) and rs689 (INS) were used.

Example 5: Determining Genetic Scores

Genetic scores were determined as described by Winkler[14] without intercept, and by Oram[15]. A total of 38/39 non-HLA class II SNPs (Tab. 3, left column) used in the Winkler score and 26/27 non-HLA class II SNPs (Tab. 3, middle column) used in the Oram score were available to calculate the genetic scores in the TEDDY children.

Genetic risk was based on risk scores derived from SNPs that define HLA DR3, HLA DR4, and HLA DQ8 alleles (rs17426593, rs2187668, rs7454108 of Tab. 3) as well as SNPs from HLA class I (rs1264813, rs2395029 of Tab. 3) and non-HLA type 1 diabetes susceptibility genes (from rs2476601 to rs2664170 of Tab. 3), and from HLA class II protective alleles (rs3129889 for DRB1*1501, rs1794265 for DQB1*0503). SNPs from HLA class I and non-HLA SNPs are classified together to "non-HLA class II SNPs" in Table 3.

For both scores, the HLA DR-DQ genotype weights (HLA class II) were added to the weighted risks for each SNP according to the child's number of risk alleles (0, 1, or 2) for each SNP (Tab. 3). Additionally, a merged genetic score based on the mean weights of each SNP in the Winkler and Oram scores was calculated for the TEDDY children (Tab. 3, right column). For two SNPs (rs2069763 and rs3825932), which had a negative weight in the Winkler score but a positive weight in the Oram score, we used the Oram score weight to calculate the merged score.

The yellow marked SNPs of Table 3 are the strongest and most important SNPs used in the merged score. In particular the 12 yellow marked non-HLA class II SNPs may apply for the minimal number of SNPs used for the merged score that may still predict a precise risk to develop type 1 diabetes at 6 years of age.

TABLE 3

Score weights for single nucleotide polymorphismsused to calculate the genetic scores. Yellow highlighted SNPs are the minimum number and most important SNPs being analyzed for and used in the merged score.

| SNP | Winkler Score Weight | Oram Score Weight | Merged Score Weight |
|---|---|---|---|
| HLA class II | | | |
| rs17426593 | 3.21 | 3.09 | 3.15 |
| rs2187668 | 4.09 | 3.87 | 3.98 |
| rs7454108 | | | |
| Non-HLA class II SNPs | | | |
| rs1264813 | | 0.43 | 0.43 |
| rs2395029 | | 0.92 | 0.92 |
| rs2476601 | 0.85 | 0.67 | 0.76 |
| rs2816316 | 0.16 | | 0.16 |

TABLE 3-continued

Score weights for single nucleotide polymorphismsused to calculate the genetic scores. Yellow highlighted SNPs are the minimum number and most important SNPs being analyzed for and used in the merged score.

| SNP | Winkler Score Weight | Oram Score Weight | Merged Score Weight |
|---|---|---|---|
| rs3024505 | 0.26 | 0.17 | 0.22 |
| rs1990760 | 0.16 | 0.15 | 0.16 |
| rs3087243 | 0.12 | 0.20 | 0.16 |
| rs10517086 | 0.19 | | 0.19 |
| rs2069763 | −0.01 | 0.11 | 0.11 |
| rs6897932 | 0.19 | | 0.19 |
| rs3757247 | 0.25 | 0.12 | 0.19 |
| rs9388489 | 0.12 | 0.16 | 0.14 |
| rs6920220 | 0.15 | | 0.15 |
| rs1738074 | 0.05 | | 0.05 |
| rs7804356 | 0.15 | | 0.15 |
| rs4948088 | 0.09 | 0.26 | 0.17 |
| rs7020673 | 0.23 | | 0.23 |
| rs12722495 | 0.47 | 0.46 | 0.47 |
| rs947474 | 0.15 | | 0.15 |
| rs10509540 | 0.22 | 0.29 | 0.25 |
| rs689 or rs1004446 | 0.74 | 0.56 | 0.65 |
| rs4763879 | 0.06 | | 0.06 |
| rs2292239 | 0.41 | 0.30 | 0.36 |
| rs3184504 | 0.24 | | 0.24 |
| rs1465788 | 0.12 | 0.15 | 0.13 |
| rs17574546 | | 0.13 | 0.13 |
| rs3825932 | −0.20 | 0.15 | 0.15 |
| rs12708716 | 0.09 | 0.21 | 0.15 |
| rs4788084 | 0.25 | 0.15 | 0.20 |
| rs7202877 | 0.13 | 0.25 | 0.19 |
| rs2290400 | 0.25 | | 0.25 |
| rs7221109 | 0.15 | | 0.15 |
| rs45450798 | 0.01 | 0.18 | 0.09 |
| rs763361 | 0.10 | 0.15 | 0.12 |
| rs425105 | 0.26 | 0.15 | 0.21 |
| rs2281808 | 0.05 | 0.10 | 0.07 |
| rs3788013 | 0.20 | 0.12 | 0.16 |
| rs5753037 | 0.20 | 0.10 | 0.15 |
| rs229541 | 0.18 | | 0.18 |
| rs5979785 | 0.09[b] | | 0.09 |
| rs2664170 | 0.14[b] | | 0.14 |
| rs917997 | 0.14[a,b] | | 0.14[a] |

[a]not included in the genetic score calculation for the TEDDY cohort
[b]not included in the Winkler genetic score calculation for the UK cohort and WTTCC patients

Example 6: Statistical Analysis

For TEDDY children, the risks of developing islet autoantibodies and multiple islet autoantibodies at 4 and 6 years of age were estimated using the Kaplan-Meier method and were compared between risk groups using the log-rank test. The risks of islet autoantibodies risk and multiple islet autoantibodies were calculated for increasing thresholds of genetic scores. The sensitivity was assessed by calculating the proportion of children who developed islet autoantibodies or multiple islet autoantibodies whose genetic score was above the threshold value. Spearman's correlation coefficient was used to assess whether the autoantibody risk and sensitivity changed with increasing score thresholds. The proportion of children in the general population who would be expected to have a genetic score above the threshold was calculated based on the frequency of HLA DR3/DR4-DQ8 and DR4-DQ8/DR4-DQ8 children (2.9%) identified in the screening phase of the TEDDY study.[20]

For the case-control dataset, we calculated the proportions of non-diabetic controls and cases of type 1 diabetes whose genetic score exceeded the thresholds, with score increments of 0.1. The sensitivity was assessed by calculating the proportion of cases within the cohort who had a score above the threshold. Specificity was calculated as 100–the proportion of controls with scores above the threshold. The empirical risk was calculated as the proportion of cases divided by the proportion of controls above the threshold multiplied by the assumed background risk of 5% for individuals with the DR3/DR4-DQ8 or DR4-DQ8/DR4-DQ8 genotype.[11]

The distribution of genetic scores was compared among the groups using the Mann-Whitney U test.

All analyses were performed using the R 3.3.2 software (R Foundation for Statistical Computing, Vienna, Austria), the SPSS version 22.0 (SPSS Inc., Chicago, IL), and SAS 9.4 (SAS Institute, Cary, NC).

Example 7: Time-Dependent Analysis of the Discrimination Accuracy

To make use of the actual time information of the development of islet autoantibodies, we performed a time-dependent analysis of the discrimination accuracy. To this end, we calculated the integral of a time dependent ROC curve[25] for each genetic risk score from 1 year to 10 years with increments of 100 days (FIG. 17). To obtain a distribution for each of these predicted scores, we performed 2000 paired bootstrap replicates for each genetic risk score (FIG. 18). These bootstrap replicates were further used to assess statistical differences of the time-dependent ROC estimates per genetic risk score. To this end, we calculated Bayes factors of the paired estimates[26] of two risk scores. Specifically, by comparing risk score 1 (RS1) and risk score 2 (RS2) the Bayes factor of RS1 versus RS2 is calculated as the posterior probability of the alternative hypothesis (defined as RS1 is better than RS2) as the fraction of bootstrap replications in which RS1 is better than RS2 divided by the posterior probability of null hypothesis (defined as RS1 is no better than RS2) as the fraction of bootstrap replications in which RS1 is no better than RS2. We denoted two genetic risk scores indistinguishable with a Bayes factor <3.[27]

Example 8: Progression from Islet Autoimmunity to Clinical Type 1 Diabetes Determined by the Genetic Risk Score In 341 islet autoantibody positive children with the HLA DR3/DR4-DQ8 or the HLA DR4-DQ8/DR4-DQ8 genotype from the prospective TEDDY study, it was investigated whether a genetic risk score that had previously been shown to predict islet autoimmunity is also associated with progression (a) from any to multiple autoantibodies, (b) from any autoantibodies to type 1 diabetes onset, and (c) from multiple autoantibodies to type 1 diabetes.

Hereto, Kaplan-Meier curves for progression stratified by quartiles of the genetic risk score were calculated from (a) any to multiple autoantibodies, (b) any autoantibodies to type 1 diabetes onset, and (c) multiple autoantibodies to type 1 diabetes onset (FIGS. 20A-20C). In order to determine the potential contribution of HLA and non-HLA SNPs and explore potential confounding by other factors, we applied Cox proportional hazards regression analysis for the three progression times with adjustment for the genetic risk score (without weighting the different HLA genotypes), HLA genotype, age at onset of the previous event (e.g., of any autoantibodies in the model of progression from any autoantibodies to type 1 diabetes), and country of ascertainment (FIG. 21). All analyses were performed using R 3.3.3 (R Foundation for Statistical Computing, Vienna, Austria). Significance was defined by p<0.05 without adjustment for multiple testing.

Results

Example 9: Case-Control Population

Figure 1C:
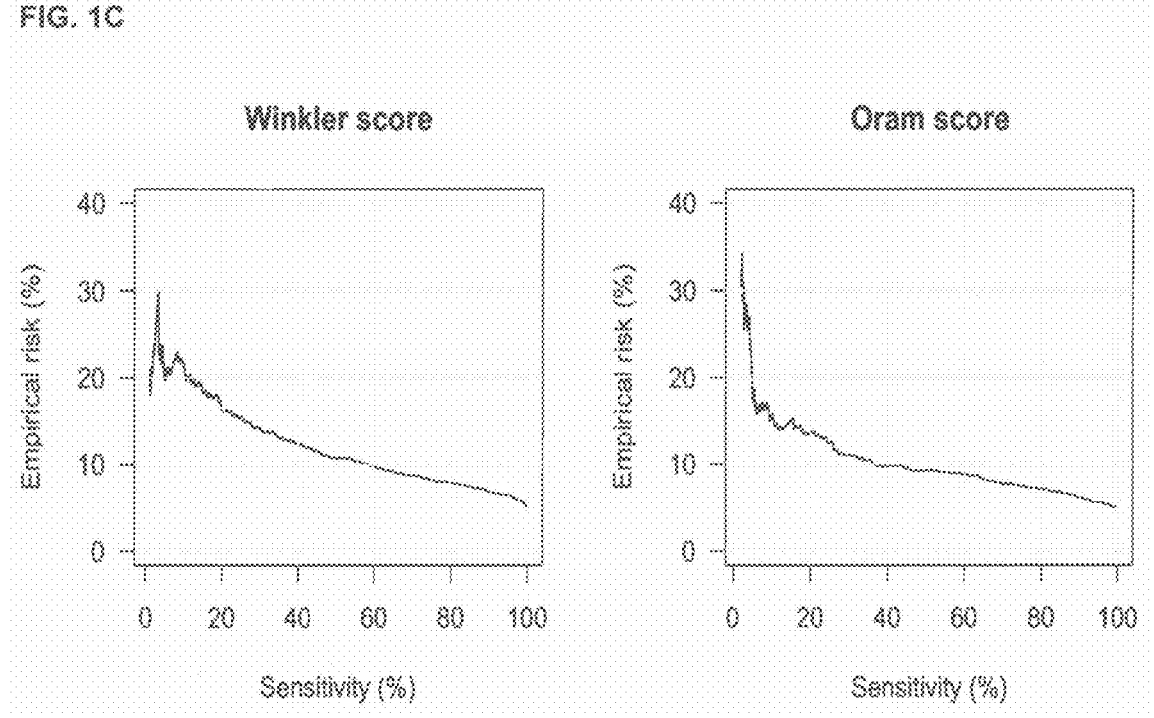

The median genetic scores in controls and cases were 11.14 (interquartile range [IQR], 10.49-11.80) and 11.91 (IQR, 11.20-12.50; P<0.0001), respectively, for the Winkler score using 35/40 SNPs, and were 10.93 (IQR, 10.39-11.45) and 11.43 (IQR, 10.96-11.59; P<0.0001), respectively, for the Oram score (FIGS. 1A and 1B). The empirical risk calculated from the case-control dataset reached 10% using the Winkler Score at a threshold of 11.718, corresponding to a sensitivity of 58.7% (95% confidence interval [CI], 55.2%-62.2%) of the patients who had HLA DR3/DR-DQ8 or DR4-DQ87DR4-DQ8 genotypes. Using the Oram score, the empirical risk of 10% was reached with a score of 11.672 corresponding to a sensitivity of 36.6% (95% CI, 33.2%-40.0%) (FIG. 1C). Having validated the ability of the genetic scores to empirically stratify the risk for type 1 diabetes in individuals with high risk HLA genotypes, we subsequently applied the scores to the TEDDY cohort using the outcome of islet autoantibodies.

Figure 2:
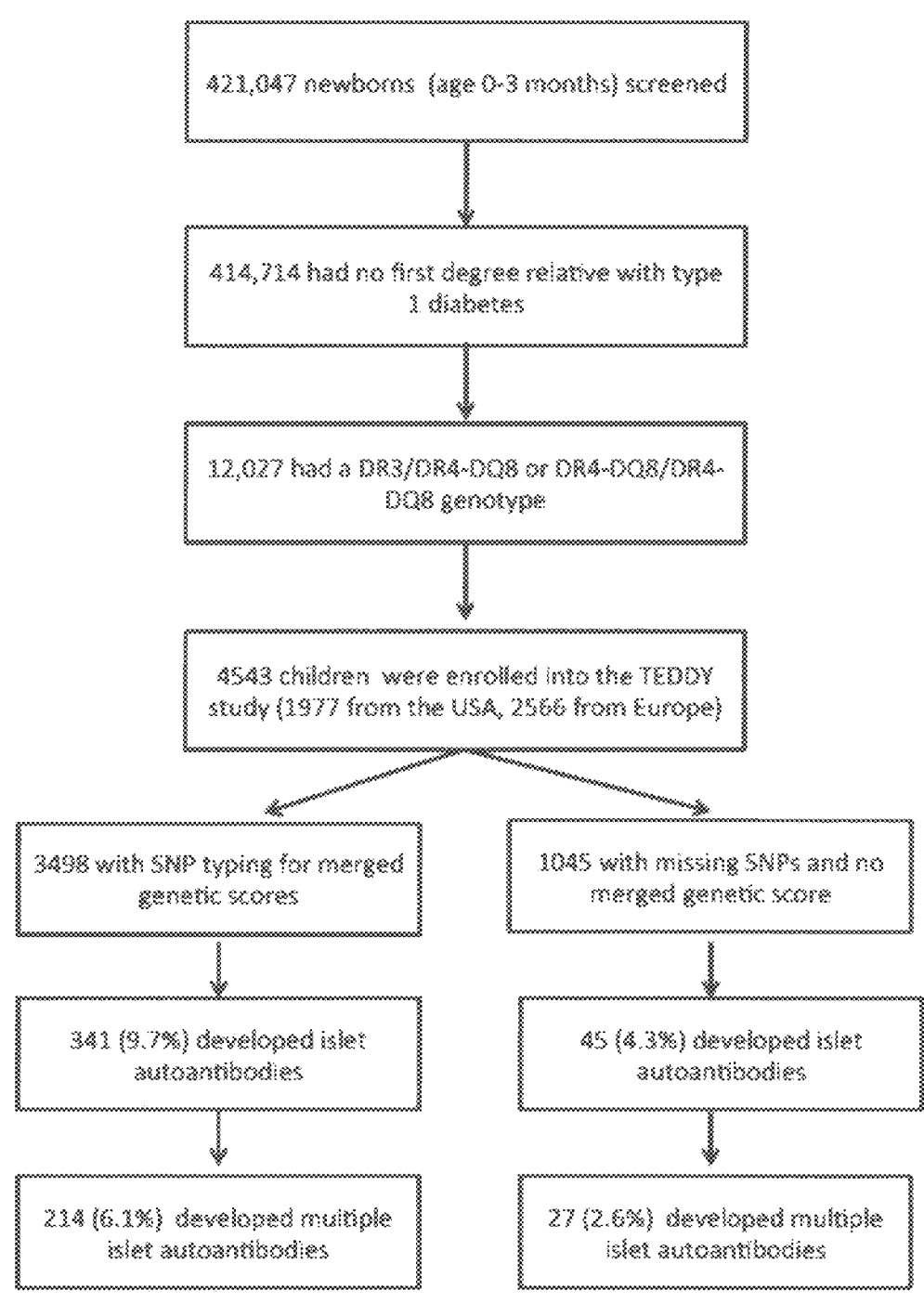
FIG. 2: Flow diagram of the participants in the TEDDY
study.

Example 10: Baseline Risk of Islet Autoantibodies in TEDDY Children with HLA DR3/DR4-DQ8 or DR4-DQ8/DR4-DQ8 Genotypes without Family History of Type 1 Diabetes Of 421,047 newborns screened, 414,714 did not have a first-degree family history of type 1 diabetes. Of these, 12,027 (2.9%) had a DR3/DR4-DQ8 or DR4-DQ8/DR4-DQ8 genotype, and of these, 4543 children, of which 1977 (43.5%) were in the USA, enrolled into the TEDDY follow-up (FIG. 2). Among these 4543 children, the median follow-up (from birth) of children with islet autoantibody measurements was 6.68 years (IQR, 2.52-8.62 years). Islet autoantibody measurements were available until at least 6 years of age in 2757 children.

Seroconversion to islet autoantibodies occurred in 386 children (8.5%) (166 [43.0%] girls) while 4157 children (91.5%) remained islet autoantibody negative (2112 [50.8%] girls).

Of the 386 children with islet autoantibodies, 241 children (62.4%) developed multiple islet autoantibodies (102 [42.3%] girls), of which 81 (33.6%) were from the USA and 160 (66.4%) from Europe. The remaining 145 children (37.6%) were positive for a single islet autoantibody at their last follow-up (64 [44.1%] girls), of which 42 (29.0%) were from the USA and 103 (71.0%) from Europe.

The cumulative risk of developing islet autoantibodies was 9.2% (95% CI, 8.2%-10.1%) (FIG. 3A) and the cumulative risk for developing multiple islet autoantibodies was 5.8% (95% CI, 5.0%-6.6%) by 6 years of age (FIG. 3B).

Example 11: Genetic Scores in TEDDY Children

Figure 4A:
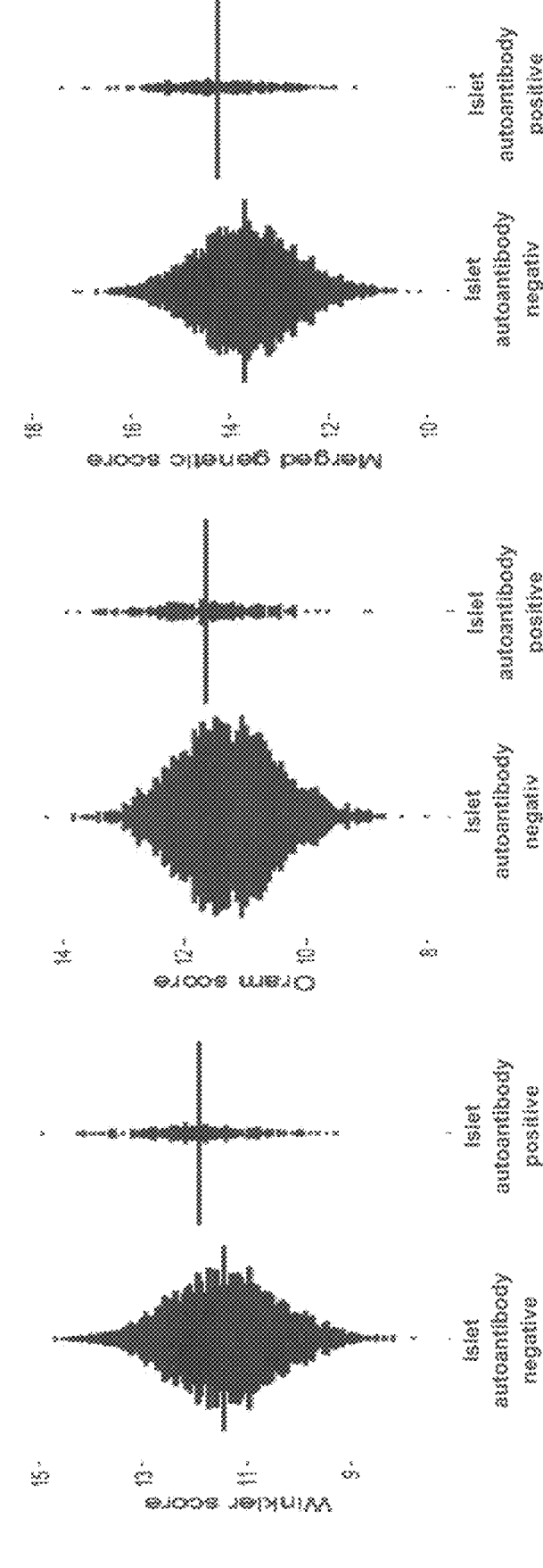

The merged genetic score as well as the Winkler and Oram genetic scores were calculated in 3498 (1471 US children), 3529 (1482 US children), and 3569 children (1500 US), respectively. The median follow-up in children for whom genetic scores could not be calculated was 1.54 years and substantially less than in children with genetic score calculation (7.39 years; P<0.0001). The median merged genetic score was greater in children who developed islet autoantibodies by 6 years of age (n=277; 14.3; IOR 13.6-14.9) than in children who remained islet autoantibody negative (13.7; IQR, 13.1-14.4; P<0.0001) (FIG. 4A). The median merged genetic score was also slightly greater in European children (13.8; IQR, 13.1-14.5) than in US children (13.7; IQR, 13.1-14.4; P=0.003) (FIG. 4B). The frequencies of minor alleles differed between the US and European children for 7/43 SNPs (Bonferroni-corrected P of 0.05/43=0.0012) (Tab. 4). The merged score was not significantly different between boys and girls (P=0.69) (FIG. 4C).

TABLE 4

Frequencies of risk alleles in TEDDY children with the
HLA DR3/DR4-DQ8 or DR4-DQ8/DR4-DQ8 genotype.

| | Frequency (%) | | |
| --- | --- | --- | --- |
| SNP | Europe | USA | P-value |
| rs3087243 | 37.28 | 45.28 | 8.30E−11 |
| rs2476601 | 12.11 | 8.8 | 2.42E−05 |
| rs4788084 | 45.77 | 40.52 | 3.80E−05 |
| rs2069763 | 40 | 35.5 | 7.61E−05 |
| rs3757247 | 41.08 | 45.73 | 0.0003 |
| rs1738074 | 40.59 | 44.98 | 0.0004 |
| rs45450798 | 17.17 | 16.12 | 0.0010 |
| rs9388489 | 44.65 | 48.77 | 0.0012 |
| rs2292239 | 33.19 | 29.45 | 0.0018 |
| rs7804356 | 21.64 | 25.11 | 0.0025 |
| rs3184504 | 45.92 | 42.72 | 0.0058 |
| rs2664170 | 30.28 | 33.62 | 0.0129 |
| rs5753037 | 34.93 | 37.96 | 0.021 |
| rs3788013 | 39.81 | 41.26 | 0.024 |
| rs1990760 | 39.98 | 43.04 | 0.028 |
| rs6897932 | 29.3 | 26.83 | 0.037 |
| rs6920220 | 21.38 | 19.13 | 0.037 |
| rs1465788 | 29.39 | 27.22 | 0.096 |
| rs2816316 | 17.65 | 19.09 | 0.1349 |
| rs229541 | 40.47 | 42.35 | 0.14 |
| rs2395029 | 0.96 | 1.46 | 0.15 |
| rs7020673 | 49.15 | 48.35 | 0.16 |
| rs7202877 | 11.74 | 10.45 | 0.18 |
| rs10509540 | 27.54 | 25.7 | 0.19 |
| rs7221109 | 37.76 | 35.83 | 0.19 |
| rs5979785 | 26.55 | 28.87 | 0.21 |
| rs12722495 | 8.29 | 9.35 | 0.26 |
| rs2290400 | 47.87 | 49.74 | 0.29 |
| rs3024505 | 16.15 | 14.95 | 0.31 |
| rs4763879 | 38.24 | 36.63 | 0.37 |
| rs3825932 | 36.13 | 34.89 | 0.37 |
| rs10517086 | 28.71 | 27.93 | 0.38 |
| rs947474 | 18.5 | 18.12 | 0.40 |
| rs4948088 | 4.51 | 5.15 | 0.45 |
| rs17574546 | 20.23 | 19.34 | 0.60 |
| rs1264813 | 9.51 | 8.98 | 0.63 |
| rs12708716 | 34.85 | 33.96 | 0.65 |
| rs425105 | 16.24 | 15.63 | 0.74 |
| rs1004446 | 37.51 | 37.15 | 0.77 |
| rs2281808 | 33.26 | 33.95 | 0.83 |
| rs763361 | 48.45 | 48.12 | 0.86 |

Example 12: Sensitivity and Risk of Islet
Autoantibodies According to the Genetic Score The cumulative risk of developing (multiple) islet autoantibodies was compared between children in the upper, middle, and lower quartiles of the TEDDY score (FIGS. 5A and 5B) and of the Winkler (FIGS. 6A and 6B) and the Oram score (FIGS. 6C and 6D). Each of the genetic scores could stratify the risks of islet autoantibodies and multiple islet autoantibodies (P<0.0001 for each score). Using the upper quartile of the merged genetic score (>14.4), the risk of islet autoantibodies was 12.1% (95% Cl, 9.8%-14.4%) and 16.0% (95% Cl, 13.3%-18.6%) at 4 and 6 years of age, respectively, compared with a risk of 6.9% (95% Cl 5.9%-8.0%) at 6 years of age in children with a score of ≤14.4 (FIG. 5A). The cumulative risk for developing multiple islet autoantibodies at 6 years of age was 11.0% (95% Cl, 8.8%-13.3%) among children with a merged genetic score of >14.4 compared with 4.1% (95% Cl, 3.3%-4.9%) in children with a score of <14.4 (P<0.0001) (FIG. 5B). Of the 3498 children with HLA DR3-DR4-DQ8 or HLA DR4-DQ8/DR4-DQ8 genotype without a family history of type 1 diabetes included in the SNP genotype analysis, 907 (25%) had a merged genetic score >14.4, corresponding to 0.73% of all the genetically screened newborns in the TEDDY study. Of the 277 children who developed beta cell autoantibodies by age 6 years, 122 (44.0%) had a score >14.4; 82 (47.4%) of 173 children who developed multiple beta cell autoantibodies by age 6 years had a score >14.4.

Figures 7C, 7D:
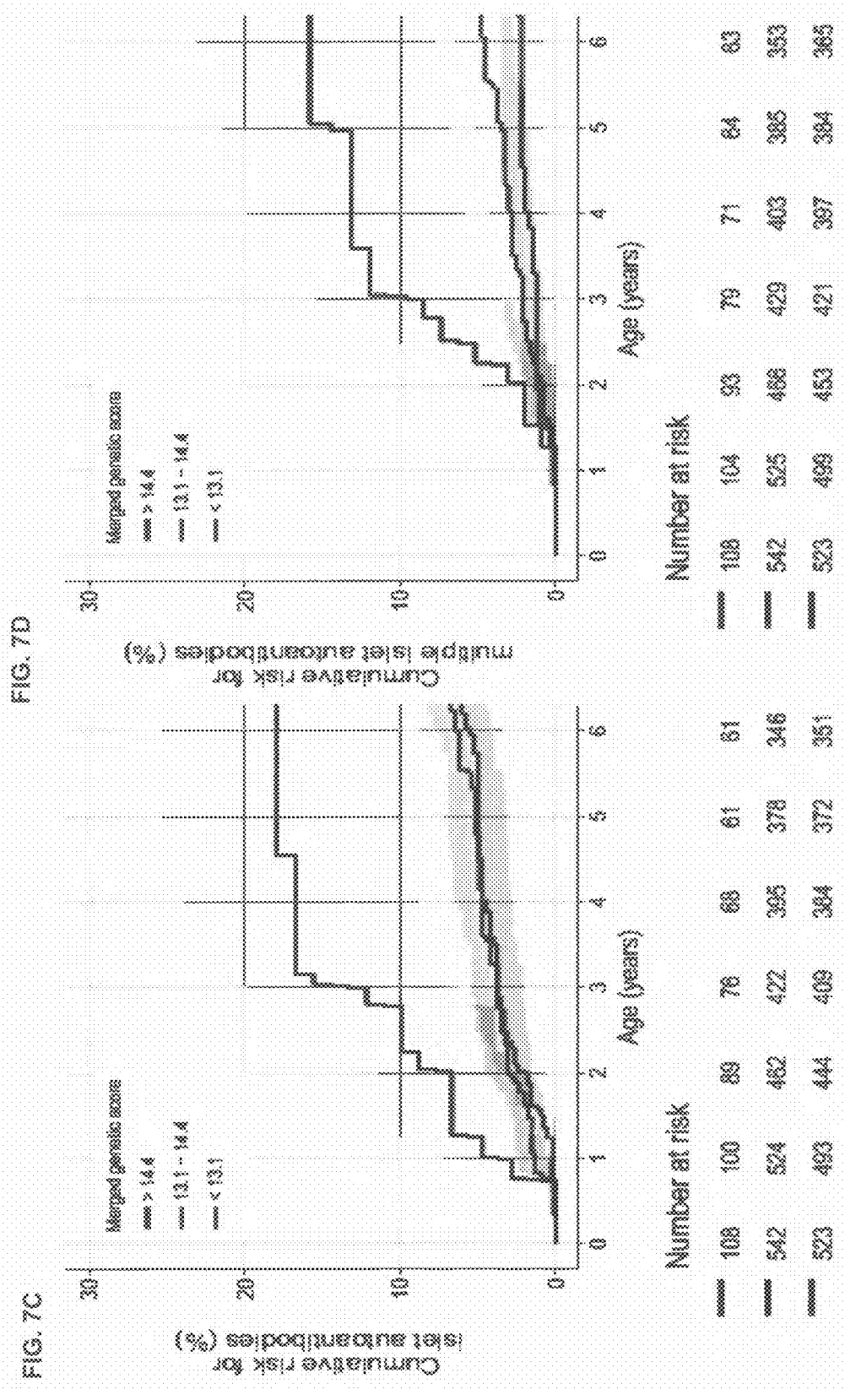
Figures 8A, 8B:
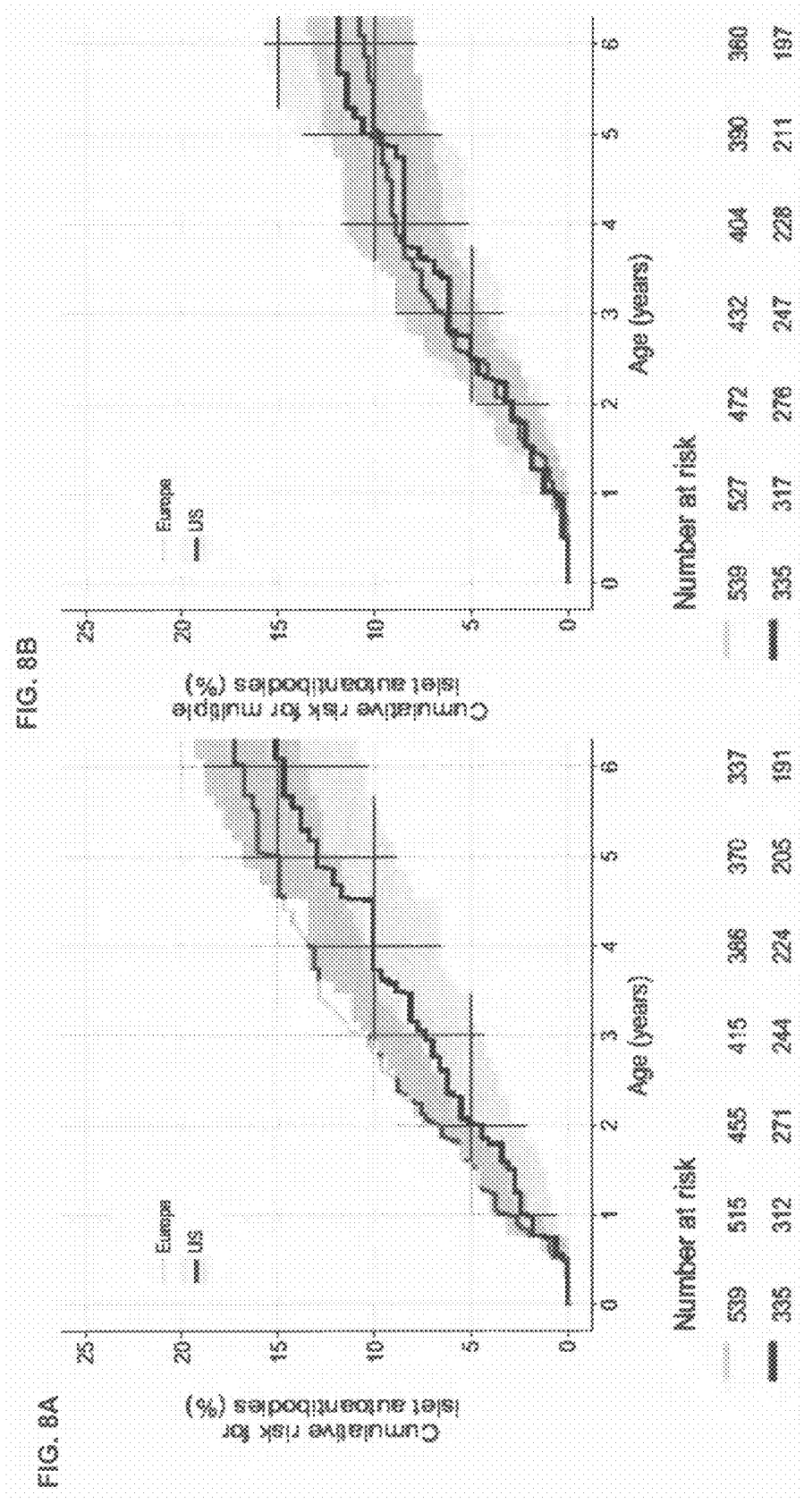

Risk for islet autoantibodies was stratified in both children who had the HLA DR3/DR4-DQ8 genotype (FIGS. 7A and 7B) and in children who had the HLA DR4-DQ8/DR4-DQ8 genotype (FIGS. 7C and 7D). The risks of islet autoantibodies or multiple islet autoantibodies in children with a merged genetic score of >14.4 were not significantly different between US and European children (P=0.16, and P=0.97) (FIGS. 8A and 8B), but these risks were higher in boys than in girls (P=0.001 and P=0.01) (FIGS. 8C and 8D).

Figure 9B:
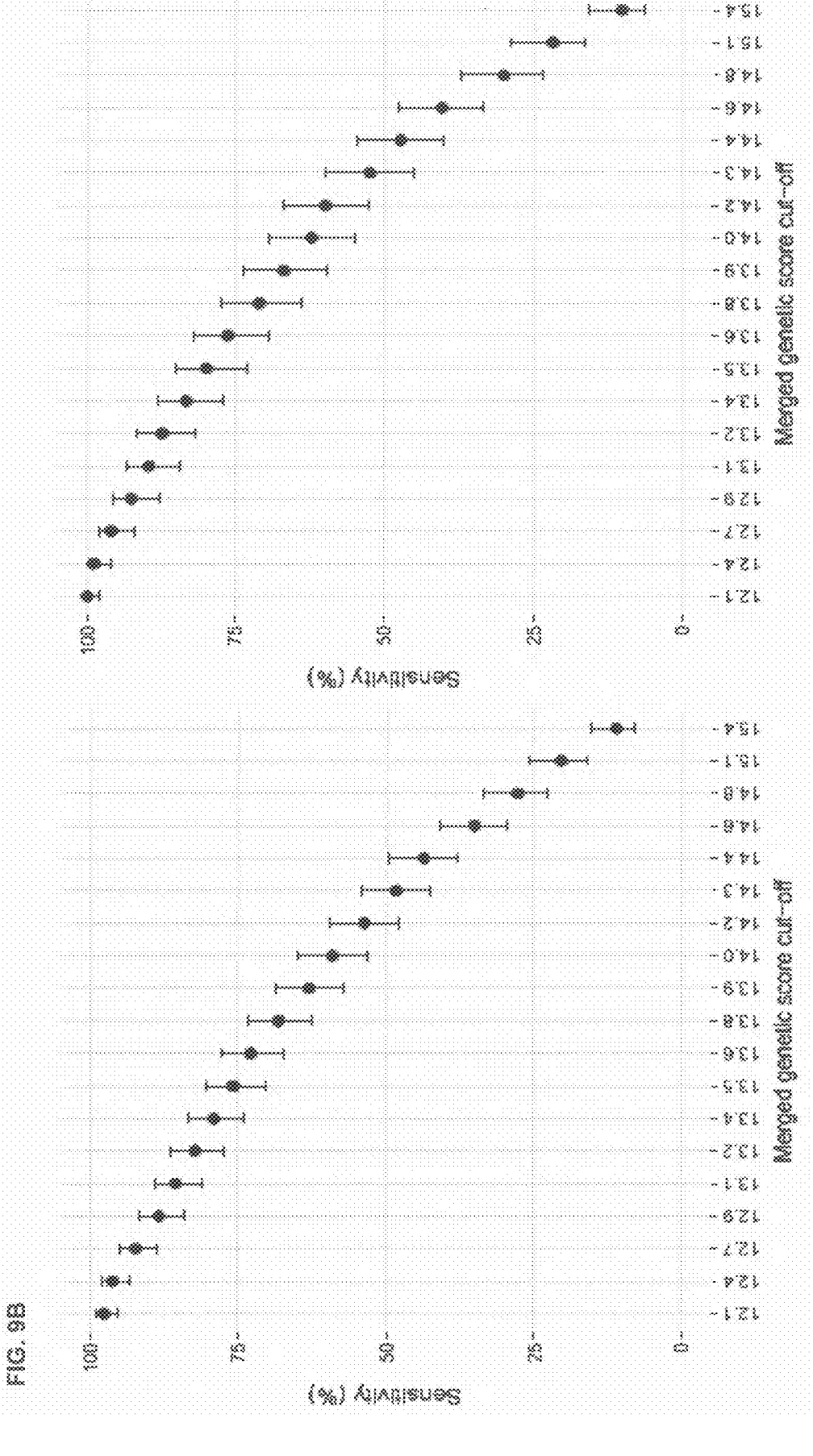
Figures 11A, 11B:
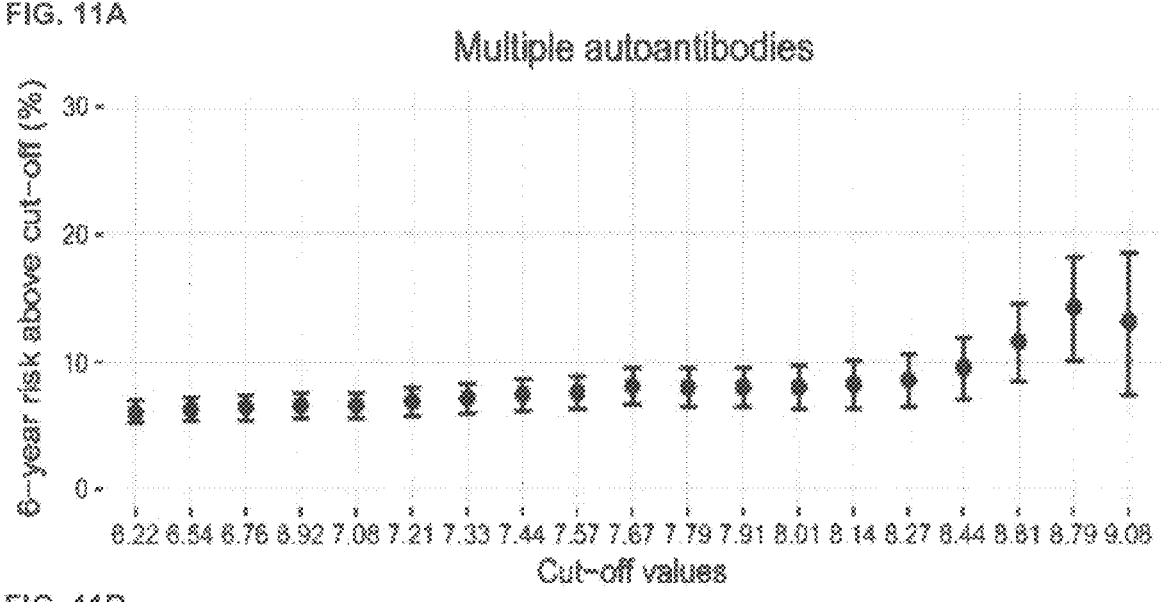
FIGS. 11A-11B: Risk of developing islet autoantibodies (FIG. 11A) and the proportion of cases positive for islet autoantibodies (sensitivity.

The cumulative risk of developing islet autoantibodies or multiple islet autoantibodies by 6 years of age increased (P<0.0001) (FIG. 9A) and the sensitivity decreased (P<0.0001) with each increment in the genetic score threshold by the $5^{th}$ percentile of the cohort using the merged score (FIG. 9B). The cumulative risk of developing multiple islet autoantibodies at 6 years of age and the proportion of cases positive for multiple islet autoantibodies (sensitivity) in TEDDY children was estimated using the validation prospective TEDDY cohort data, to whom said 41 SNPs depicted in Table 1 of the merged score were applied (FIG. 10). Only applying the minimum number of SNPs (15 yellow marked SNPs from Table 3 of the merged score) to said TEDDY cohort data, established the risk score cut-off values indicating the risk of developing multiple islet autoantibodies at 6 years of age as shown in FIGS. 11A-11B and 12.

Figures 13A, 13B:
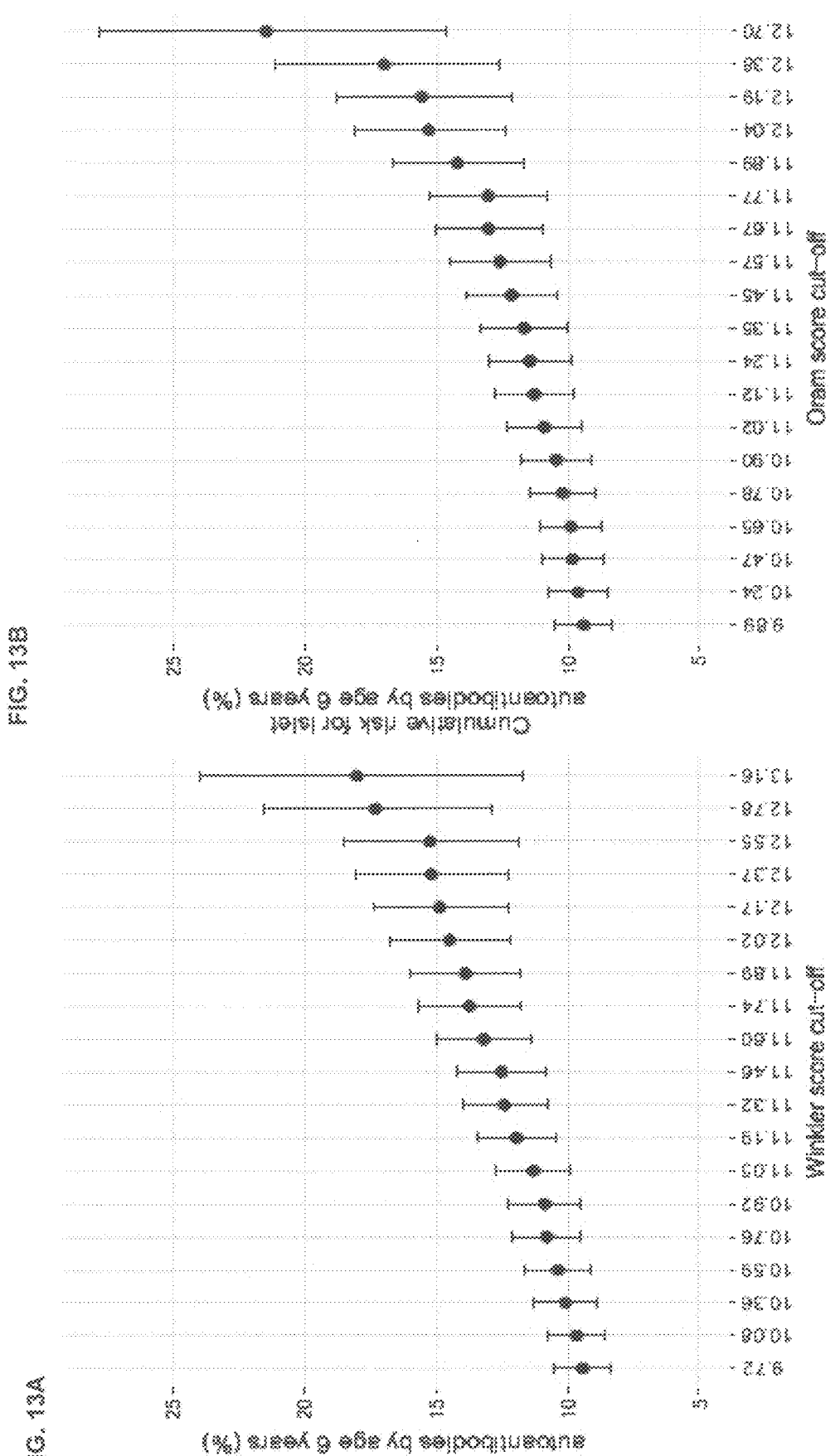
FIGS. 13A-13D: Risk of developing islet autoantibodies (FIG. 13A and FIG. 13B) and the proportion of children positive for islet autoantibodies (Sensitivity.
Figures 13C, 13D:
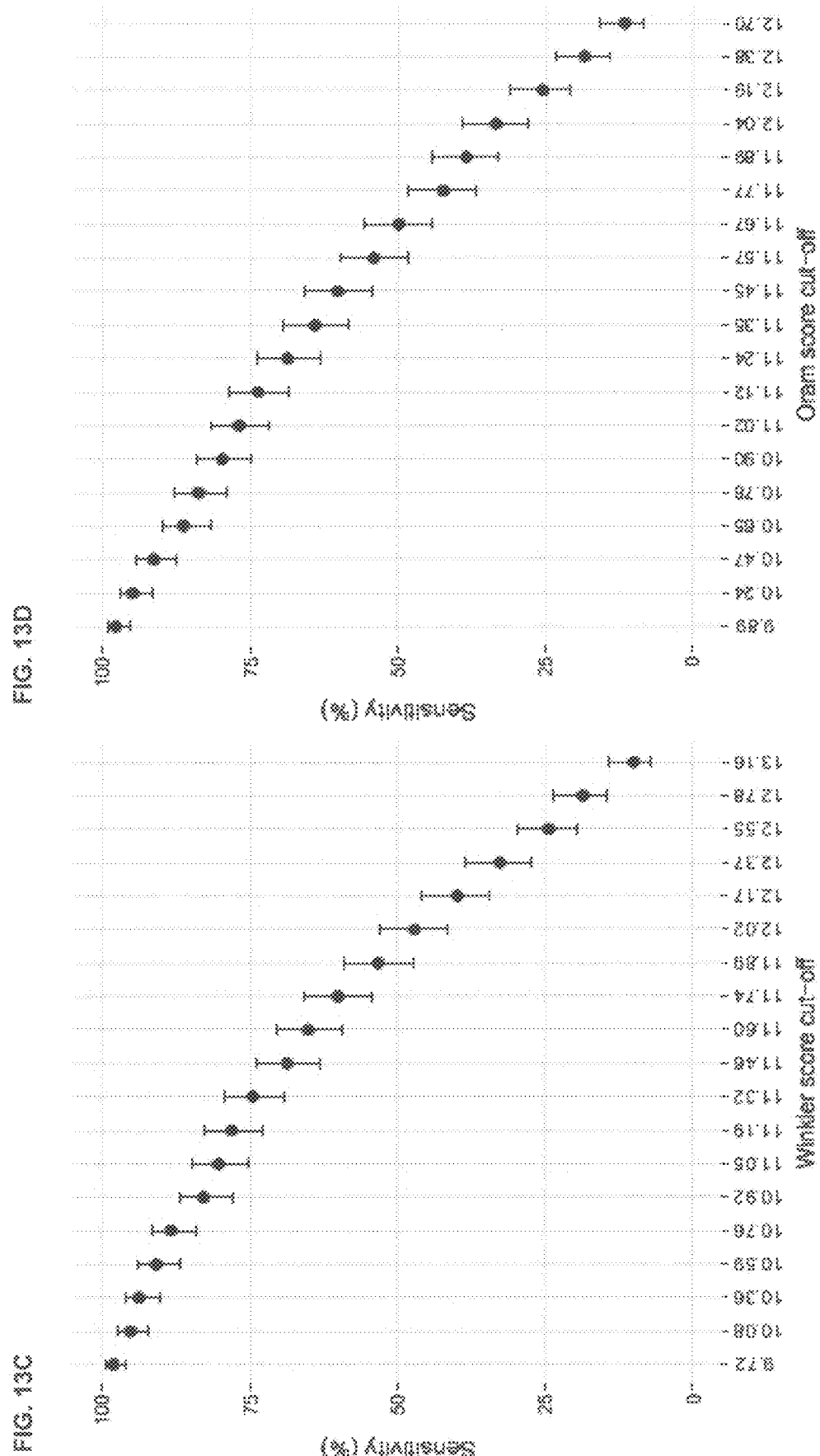
Figures 14A, 14B:
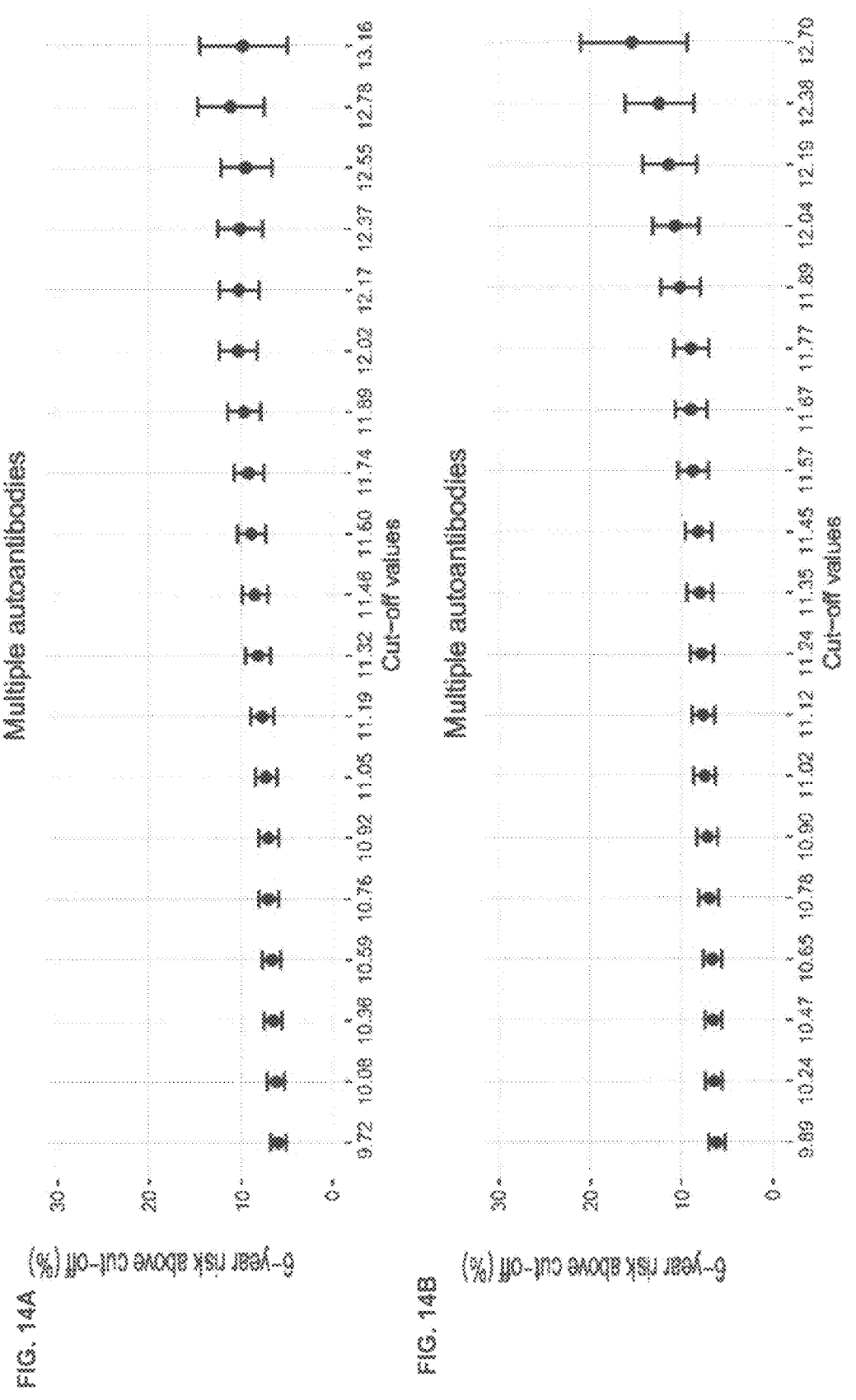
FIGS. 14A-14D: Risk of developing multiple islet autoantibodies (FIG. 14A and FIG. 14B) and the proportion of children positive for multiple islet autoantibodies (Sensitivity.
Figures 14C, 14D:
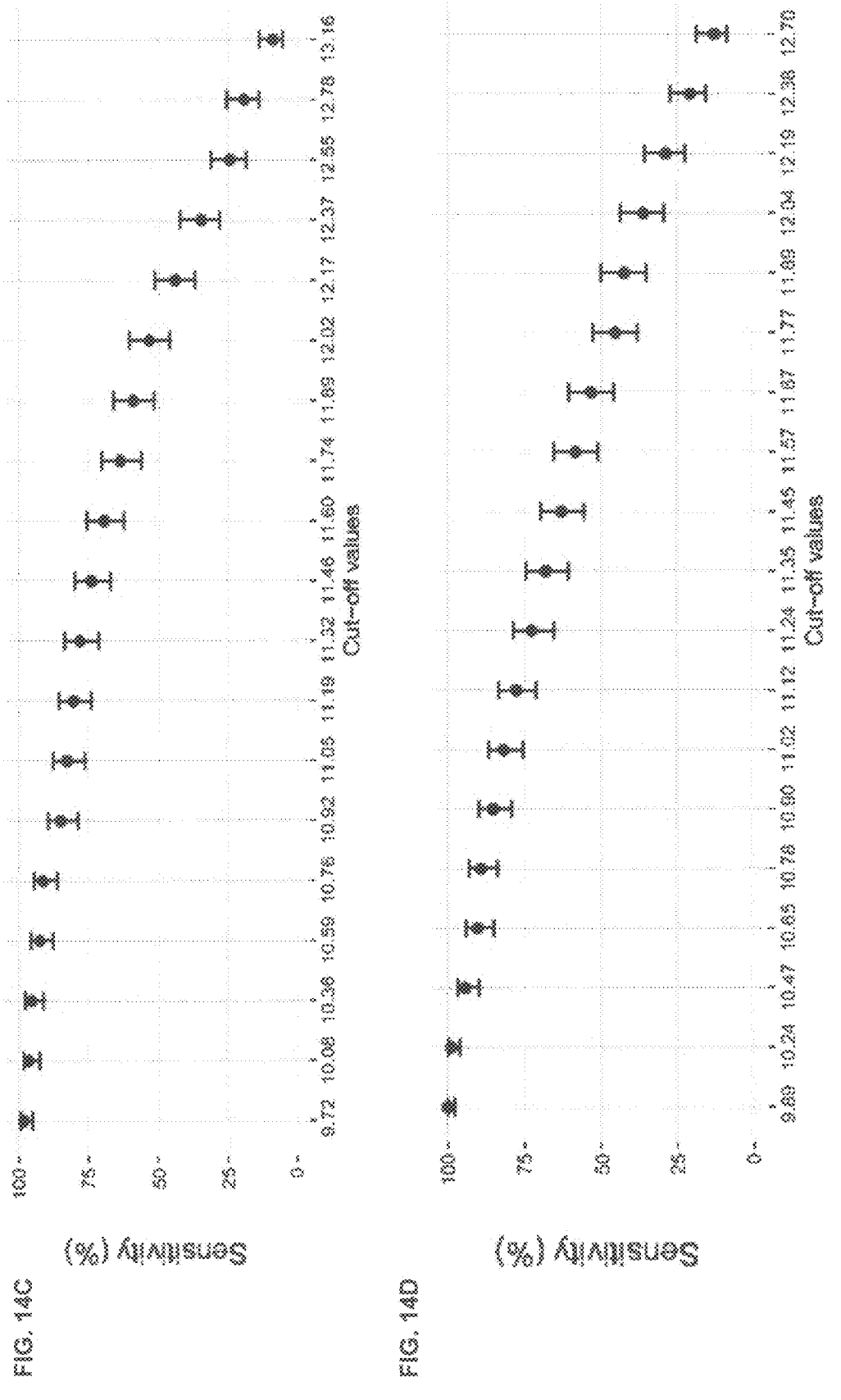

In comparison, the risk of developing (multiple) islet autoantibodies at 6 years of age and the proportion of cases positive for (multiple) islet autoantibodies (sensitivity) in TEDDY children was estimated using the validation prospective TEDDY cohort data, to whom said 38 of the 39 non-HLA class II Winkler SNPs (FIGS. 13A/13C, 14A/14C and 15) and to whom 26 of the 27 non-HLA class II Oram SNPs (FIGS. 13B/13D, 14B/14D and 16) were applied.

Example 13: Time-Dependent Analysis of the
Discrimination Accuracy

Incorporating the actual time information of the development of islet autoimmunity in the TEDDY children, we obtained an integrated time dependent AUC (iAUC) for the Oram risk score iAUC=0.665, the Winkler risk score iAUC=0.667, and the merged iAUC=0.678 (FIG. 17). To estimate the variation of the time dependent accuracy measure and to assess differences of the iAUC, we performed paired bootstrap replicates (FIG. 18). Comparing the Oram risk score to the merged score, we observed a BF=94, Winkler score vs. Oram BF=1.2, and Winkler vs. merged score BF=6.4, indicating a substantial difference between these two scores (FIG. 19).

Example 14: Progression from Islet Autoimmunity to Clinical Type 1 Diabetes Determined by the Genetic Risk Score The 341 children (141 girls, 41.3%) with a HLA DR3/DR4-DQ8 (n=250) or HLA DR4-DQ8/DR4-DQ8 (n=91) genotype who developed islet autoantibodies were followed to a median (interquartile range, IQR) age of 7.9 (6.2, 9.5) years. During this follow-up period, 214 children (62.8%) have developed multiple autoantibodies at a median age of 2.8 (1.8, 5.1) years, and 107 (31.4%) of the children developed clinical type 1 diabetes at a median age of 5.0 (3.0, 7.1) years. The median (IQR) genetic risk score was 14.23 (13.47, 14.88) in all children and was higher in the children who developed clinical type 1 diabetes (14.36 (13.73, 15.03)) as compared to the children who remained single islet autoantibody positive (14.01 (13.15, 14.56), $p=0.007$) at last visit. In the autoantibody positive children with a genetic risk score in the lowest quartile (<13.47), progression from single to multiple islet autoantibodies, single autoantibodies to diabetes, and multiple islet autoantibodies to type 1 diabetes was slower (FIGS. 20A-20C). In a Cox proportional hazards analysis, an increased genetic risk score and an earlier age of islet autoantibody development were associated consistently with a faster progression to subsequent stages of autoimmunity and type 1 diabetes. The HLA DR3/4-DQ8 genotype and country of ascertainment did not influence the rate of progression at any stage after the appearance of islet autoantibodies (FIG. 21).

Discussion

The newly established TEDDY score derived from numerous loci associated with type 1 diabetes susceptibility were able to stratify the risk of pre-symptomatic type 1 diabetes in a prospective cohort of children without family history of type 1 diabetes who had high risk HLA genotypes. The risks of developing islet autoantibodies and multiple islet autoantibodies increased with each increment in the genetic score. A genetic score that identifies <1% of all newborn infants was associated with a risk of developing multiple islet autoantibodies of >10% by 6 years of age. This compares to a background population risk of around 0.4%. These findings provide a paradigm for identifying infants whose risk of developing type 1 diabetes is >20 times greater than that of the general population. Their risk also exceeds the risk in children with a first-degree relative with type 1 diabetes.

The study was performed using a large number of children who were prospectively followed for the development of islet autoantibodies during childhood. The findings were consistent between US and European children and for two independently derived genetic scores. Since the two scores (Winkler and Oram) were not completely overlapping in their SNPs, a score defined by merging the two previously reported genetic scores was also used, which had further a significantly advantage over the already established scores of Winkler and Oram. The current scores were derived from cohorts of mostly European descent (Caucasians), and it is possible that the genetic scores may not be suitable for all races or ethnic groups.

The study was performed to extend the opportunities for identifying individuals at increased risk of disease. Previous primary prevention trials in type 1 diabetes involved HLA selection of infants with a family history of type 1 diabetes. The enrollment of participants into these trials took several years and the proportion of all cases of childhood type 1 diabetes that were represented by the inclusion criteria was less than 5%. HLA typing of the general population can identify individuals with 3% to 5% risk, which may be insufficient for enrollment into primary prevention studies in which infants are exposed to treatment. A risk target of 10% was set, which was achieved in the study when the development of multiple islet autoantibodies as a marker for pre-symptomatic type 1 diabetes was sued. The risk threshold was reached in children with the two highest-risk HLA genotypes, DR3/DR4DQ8 and DR4-DQ8/DR4-DQ8, which can be detected by typing of three SNPs. In a European population, these two genotypes were present in around 40% of all cases of childhood type 1 diabetes. The genetic score threshold identified around 50% of children with these genotypes who developed multiple islet autoantibodies. Therefore, it can be concluded that this threshold identifies 20% of children who develop type 1 diabetes without family history of diabetes. Extending the strategy to individuals with other HLA genotypes is possible, but the other genotypes are less frequent in type 1 diabetes and are associated with a lower risk than that conferred by the DR3/DR4-DQ8 and DR4-DQ8/DR4-DQ8 genotypes. Therefore, the inclusion of other genotypes is unlikely to further improve risk stratification.

In conclusion, the newly established TEDDY score (merged score) based on three SNPs for HLA class II genotyping and 41 SNPs in other genes identified <1% of newborn children who, in the absence of a family history of type 1 diabetes, had a risk of >10% for developing multiple islet autoantibodies by 6 years of age. Further, it was demonstrated that the TEDDY score may be used to stratify the rate of progression to subsequent stages of autoimmunity and type 1 diabetes in prevention trials. This greatly extends the possibilities of enrolling participants into clinical trials aimed at evaluating type 1 diabetes prevention strategies that could be applied in infancy and before the development of autoimmunity.

REFERENCES

1. Du Toit G, Roberts G, Sayre P H et al. Randomized trial of peanut consumption in infants at risk for peanut allergy. The New England Journal of Medicine. 2015; 372:803-813.
2. Krischer J P, Lynch K F, Schatz D A et al. The 6 year incidence of diabetes-associated autoantibodies in genetically at-risk children: the TEDDY study. Diabetologia. 2015; 58:980-987.
3. Knip M, Åkerblom H K, Becker D et al. Hydrolyzed infant formula and early p-cell autoimmunity: a randomized clinical trial. The Journal of the American Medical Association. 2014; 311:2279-2287.
4. Bonifacio E, Ziegler A G, Klingensmith G et al. Effects of high dose oral insulin on immune responses in children at high risk for type 1 diabetes: the Pre-POINT randomized clinical trial. The Journal of the American Medical Association. 2015; 313:1541-1549.
5. Vriezinga S L, Auricchio R, Bravi E et al. Randomized feeding intervention in infants at high risk for celiac disease. N Engl J Med. 2014; 371(14):1304-15.

6. Lionetti E, Castellaneta S, Francavilla R et al. Introduction of gluten, HLA status, and the risk of celiac disease in children. N Engl J Med. 2014; 371(14):1295-303.

7. Liu E, Lee H S, Aronsson C A et al. Risk of pediatric celiac disease according to HLA haplotype and country. N Engl J Med. 2014 Jul. 3; 371(1):42-9.

8. Bonifacio E. Predicting type 1 diabetes using biomarkers. Diabetes Care. 2015; 38(6):989-96.

9. Näntö-Salonen K, Kupila A, Simell S et al. Nasal insulin to prevent type 1 diabetes in children with HLA genotypes and autoantibodies conferring increased risk of disease: a double-blind, randomised controlled trial. Lancet. 2008; 372(9651):1746-55.

10. Rewers M, Bugawan T L, Norris J M et al. Newborn screening for HLA markers associated with IDDM: diabetes autoimmunity study in the young (DAISY). Diabetologia. 1996; 39(7):807-12.

11. Lambert A P, Gillespie K M, Thomson G et al. Absolute risk of childhood-onset type 1 diabetes defined by human leukocyte antigen class II genotype: a population-based study in the United Kingdom. Journal of Clinical Endocrinology and Metabolism. 2004; 89:4037-4043.

12. Barrett J C, Clayton D G, Concannon P et al. Genome-wide association study and meta-analysis find that over 40 loci affect risk of type 1 diabetes. Nat Genet. 2009; 41(6):703-7.

13. Clayton D G. Prediction and interaction in complex disease genetics: experience in type 1 diabetes. PLoS Genet. 2009; 5(7):e1000540.

14. Winkler C, Krumsiek J, Buettner F et al. Feature ranking of type 1 diabetes susceptibility genes improves prediction of type 1 diabetes. Diabetologia. 2014; 57:2521-2529.

15. Oram R A, Patel K, Hill A et al. A type 1 diabetes genetic risk score can aid discrimination between type 1 and type 2 diabetes in young adults. Diabetes Care. 2016; 39(3):337-344.

16. Ziegler et al. Seroconversion to Multiple Islet Autoantibodies and Risk of Progression to Diabetes in Children. JAMA. Vol 309, No. 23, 2013.

17. Ziegler A G, Nepom G T. Prediction and pathogenesis in type 1 diabetes. Immunity 32(4):468-78, 2010.

18. Nolan C, Margoliash E, Peterson J D, Steiner D F. The Structure of Bovine Proinsulin. Journal of Biological Chemistry. 246 (9): 2780-2795., 1971.

19. Groskreutz D. Genetically Engineered Proinsulin Constitutively Processed and Secreted as Mature, Active Insulin. The Journal of Biological Chemistry. 8: 6241-6245, 1993.

20. Sudlow C, Gallacher J, Allen N et al. U K biobank: an open access resource for identifying the causes of a wide range of complex diseases of middle and old age. PLoS Med. 2015; 12(3):e1001779.

21. Wellcome Trust Case Control Consortium. Genome-wide association study of 14,000 cases of seven common diseases and 3,000 shared controls. Nature 2007; 447:661-678.

22. The TEDDY Study Group The environmental determinants of diabetes in the young (TEDDY) study: study design. Pediatric Diabetes. 2007; 8:286-298.

23. Bonifacio E, Yu L, Williams A K et al. Harmonization of glutamic acid decarboxylase and islet antigen-2 autoantibody assays for national institute of diabetes and digestive and kidney diseases consortia. J Clin Endocrinol Metab. 2010; 95(7):3360-7.

24. Törn C, Hadley D, Lee H S et al. Role of Type 1 Diabetes-Associated SNPs on Risk of Autoantibody Positivity in the TEDDY Study. Diabetes. 2015; 64(5): 1818-29.

25. Blanche P, Dartigues J F, Jacqmin-Gadda H (2013) Estimating and comparing time-dependent areas under receiver operating characteristic curves for censored event times with competing risks. Statistics in medicine 32: 5381-5397.

26. Guinney J, Wang T, Laajala T D, et al. (2017) Prediction of overall survival for patients with metastatic castration-resistant prostate cancer: development of a prognostic model through a crowdsourced challenge with open clinical trial data. The Lancet Oncology 18: 132-142.

27. Kass R E, Raftery A E (1995) Bayes factors. Journal of the american statistical association 90: 773-795.

The invention claimed is:

1. A kit for determining a genetic risk score for developing type 1 diabetes, comprising:

an oligonucleotide comprising SEQ ID NO: 1;
an oligonucleotide comprising SEQ ID NO: 2;
an oligonucleotide comprising SEQ ID NO: 3;
an oligonucleotide comprising SEQ ID NO: 4;
an oligonucleotide comprising SEQ ID NO: 5;
an oligonucleotide comprising SEQ ID NO: 6;
an oligonucleotide comprising SEQ ID NO: 7;
an oligonucleotide comprising SEQ ID NO: 8;
an oligonucleotide comprising SEQ ID NO: 9;
an oligonucleotide comprising SEQ ID NO: 10;
an oligonucleotide comprising SEQ ID NO: 11;
an oligonucleotide comprising SEQ ID NO: 12;
an oligonucleotide comprising SEQ ID NO: 13;
an oligonucleotide comprising SEQ ID NO: 14;
an oligonucleotide comprising SEQ ID NO: 15;
an oligonucleotide comprising SEQ ID NO: 16;
an oligonucleotide comprising SEQ ID NO: 17;
an oligonucleotide comprising SEQ ID NO: 18;
an oligonucleotide comprising SEQ ID NO: 19;
an oligonucleotide comprising SEQ ID NO: 20;
an oligonucleotide comprising SEQ ID NO: 21;
an oligonucleotide comprising SEQ ID NO: 22;
an oligonucleotide comprising SEQ ID NO: 23;
an oligonucleotide comprising SEQ ID NO: 24;
an oligonucleotide comprising SEQ ID NO: 25;
an oligonucleotide comprising SEQ ID NO: 26;
an oligonucleotide comprising SEQ ID NO: 27;
an oligonucleotide comprising SEQ ID NO: 28;
an oligonucleotide comprising SEQ ID NO: 29;
an oligonucleotide comprising SEQ ID NO: 30;
an oligonucleotide comprising SEQ ID NO: 31;
an oligonucleotide comprising SEQ ID NO: 32;
an oligonucleotide comprising SEQ ID NO: 33;
an oligonucleotide comprising SEQ ID NO: 34;
an oligonucleotide comprising SEQ ID NO: 35;
an oligonucleotide comprising SEQ ID NO: 36;
an oligonucleotide comprising SEQ ID NO: 37;
an oligonucleotide comprising SEQ ID NO: 38;
an oligonucleotide comprising SEQ ID NO: 39;
an oligonucleotide comprising SEQ ID NO: 40;
an oligonucleotide comprising SEQ ID NO: 41; and
an oligonucleotide comprising SEQ ID NO: 42.

2. A method of immunizing a subject against type 1 diabetes, comprising administering to the subject a type 1 diabetes antigen, wherein the subject is determined to be at risk of developing type 1 diabetes by a method of:

(a) multiplying the corresponding score weight per risk allele of each of the 41 single nucleotide polymorphisms (SNPs), listed in the table below, with the corresponding number of risk alleles determined in a sample from the subject for each of the 41 SNPs,

| SNP | score weight per allele |
| --- | --- |
| rs1264813 | 0.43 |
| rs2395029 | 0.92 |
| rs2476601 | 0.76 |
| rs2816316 | 0.16 |
| rs3024505 | 0.22 |
| rs1990760 | 0.16 |
| rs3087243 | 0.16 |
| rs10517086 | 0.19 |
| rs2069763 | 0.11 |
| rs6897932 | 0.19 |
| rs3757247 | 0.19 |
| rs9388489 | 0.14 |
| rs6920220 | 0.15 |
| rs1738074 | 0.05 |
| rs7804356 | 0.15 |
| rs4948088 | 0.17 |
| rs7020673 | 0.23 |
| rs12722495 | 0.47 |
| rs947474 | 0.15 |
| rs10509540 | 0.25 |
| rs689 or rs1004446 | 0.65 |
| rs4763879 | 0.06 |
| rs2292239 | 0.36 |
| rs3184504 | 0.24 |
| rs1465788 | 0.13 |
| rs17574546 | 0.13 |
| rs3825932 | 0.15 |
| rs12708716 | 0.15 |
| rs4788084 | 0.20 |
| rs7202877 | 0.19 |
| rs2290400 | 0.25 |
| rs7221109 | 0.15 |
| rs45450798 | 0.09 |
| rs763361 | 0.12 |
| rs425105 | 0.21 |
| rs2281808 | 0.07 |
| rs3788013 | 0.16 |
| rs5753037 | 0.15 |
| rs229541 | 0.18 |
| rs5979785 | 0.09 |
| rs2664170 | 0.14 | wherein the number of risk alleles for each SNP is 0 if a risk allele of the SNP is determined to be not present, 1 if a risk allele of the SNP is determined to be present heterozygously, or 2 if a risk allele of the SNP is determined to be present homozygously;

(b) assigning a score number of 3.15 if SNP rs17426593, SNP rs2187668, and SNP rs7454108 are determined in the subject having a HLA DR4-DQ8/DR4-DQ8 genotype and a score number of 3.98 if SNP rs17426593, SNP rs2187668, and SNP rs7454108 are determined in the subject having a HLA DR3/DR4-DQ8 genotype; and (c) summing up multiplication products of step (a) and any corresponding assigned score number of step (b) determined in the subject, thereby obtaining a genetic risk score, wherein the genetic risk score equal to or greater than 13.47 is indicative that the subject is at risk of developing type 1 diabetes, wherein said type 1 diabetes antigen is administered to the subject at a dose of 50 to 100 mg, wherein said type 1 diabetes antigen is administered orally and daily, and wherein said type 1 diabetes antigen is selected from the group consisting of insulin, proinsulin, insulin analog, and peptides thereof, thereby immunizing a subject against type 1 diabetes.

3. The method of claim 2, wherein said type 1 diabetes antigen is administered to the subject for 60 months or less.

4. The method of claim 2, wherein said subject is an infant 2 to 10 months of age at the beginning of the administration.

5. The method of claim 2, wherein said subject is an adult, a non-adult, a newborn or an infant, and wherein said newborn or said infant is not older than 3 months.

6. The method of claim 2, wherein if the genetic risk score is at least 13.9, it is indicative that said newborn or said infant has an at least 10% genetic risk to develop type 1 diabetes by an age of 6 years.

7. The method of claim 2, wherein said sample is a blood sample or saliva sample.

\* \* \* \* \*